US009738885B2

(12) United States Patent
Watanabe et al.

(10) Patent No.: US 9,738,885 B2
(45) Date of Patent: Aug. 22, 2017

(54) NITRILE HYDRATASE

(71) Applicant: Mitsubishi Chemical Corporation, Tokyo (JP)

(72) Inventors: Fumiaki Watanabe, Kanagawa (JP); Ai Hara, Kanagawa (JP); Takanori Ambo, Aichi (JP); Aya Kitahara, Kanagawa (JP)

(73) Assignee: Mitsubishi Chemical Corporation, Tokyo (JP)

(*) Notice: Subject to any disclaimer, the term of this patent is extended or adjusted under 35 U.S.C. 154(b) by 98 days.

(21) Appl. No.: 14/852,979

(22) Filed: Sep. 14, 2015

(65) Prior Publication Data

US 2016/0068833 A1 Mar. 10, 2016

Related U.S. Application Data

(62) Division of application No. 14/124,555, filed as application No. PCT/JP2012/003745 on Jun. 7, 2012, now Pat. No. 9,193,966.

(30) Foreign Application Priority Data

Jun. 7, 2011 (JP) ................................ 2011-127466
Jun. 29, 2011 (JP) ................................ 2011-144378
Jun. 30, 2011 (JP) ................................ 2011-145061

(51) Int. Cl.

| | |
|---|---|
| ***C12P 13/02*** | (2006.01) |
| ***C12N 9/88*** | (2006.01) |
| ***C07K 14/47*** | (2006.01) |

(52) U.S. Cl.

CPC .............. *C12N 9/88* (2013.01); *C07K 14/472* (2013.01); *C12P 13/02* (2013.01); *C12Y 402/01084* (2013.01)

(58) Field of Classification Search

CPC ......................... C12P 13/02; C12Y 402/01084
See application file for complete search history.

(56) References Cited

U.S. PATENT DOCUMENTS

| | | | |
|---|---|---|---|
| 5,731,176 | A | 3/1998 | Yamada et al. |
| 5,807,730 | A | 9/1998 | Ito et al. |
| 5,827,699 | A | 10/1998 | Yanenko et al. |
| 7,595,184 | B2 | 9/2009 | Yamaki et al. |
| 2001/0044141 | A1 | 11/2001 | Akoi et al. |
| 2007/0009985 | A1 | 1/2007 | Yamaki et al. |
| 2007/0231868 | A1 | 10/2007 | Watanabe et al. |
| 2008/0236038 | A1 | 10/2008 | Pierce et al. |
| 2011/0212506 | A1 | 9/2011 | Matsumoto et al. |

FOREIGN PATENT DOCUMENTS

| | | | |
|---|---|---|---|
| EP | 0 445 646 | A2 | 9/1991 |
| EP | 1 842 907 | A1 | 10/2007 |
| EP | 2 716 754 | A1 | 4/2014 |
| JP | 9 248188 | | 9/1997 |
| JP | 9 275978 | | 10/1997 |
| JP | 10 337185 | | 12/1998 |
| JP | 3162091 | | 2/2001 |
| JP | 2001 292772 | | 10/2001 |
| JP | 2004 194588 | | 7/2004 |
| JP | 2005 016403 | | 1/2005 |
| JP | 2007 043910 | | 2/2007 |
| JP | 2007 143409 | | 6/2007 |
| JP | 2008 154552 | | 7/2008 |
| JP | 2008-228628 | A | 10/2008 |
| JP | 2008 253182 | | 10/2008 |
| JP | 2010 172295 | | 8/2010 |
| JP | 2010-187660 | A | 9/2010 |
| JP | 2011-41563 | | 3/2011 |
| WO | 2004 056990 | | 7/2004 |
| WO | 2005/090595 | | 9/2005 |
| WO | 2005 116206 | | 12/2005 |
| WO | WO 2009/009117 | A2 | 1/2009 |
| WO | 2010 055666 | | 5/2010 |
| WO | WO 2012/164933 | A1 | 12/2012 |

OTHER PUBLICATIONS

Australian Office Action issued Dec. 6, 2016 in Patent Application No. 2015203199.

Takarada, H. et al., "Mutational Study of αGln90 of Fe—type Nitrile Hydratase from *Rhodococcus* sp. N771", Biosci. Biotechnol. Biochem., vol. 70, No. 4, pp. 881-889, (2006).

Prasad, S. et al., "Nitrile hydratases (NHases): at the interface of academia and industry", Biotechnology Advances, vol. 28, No. 6, pp. 725-741, (2010).

Veiko, V. P. et al., "Cloning, Nucleotide Sequence of Nitrile Hydratase Gene from *Rhodococcus rhodochrous* M8", Biotckhnologiia , N 5-6, pp. 3-5, (1995) (with partial English translation).

International Search Report Issued Sep. 18, 2012 in PCT/JP12/003745 Filed Jun. 7, 2012.

Extended European Search Report issued Mar. 4, 2014 in Patent Application No. 12796356.9.

Partial European Search Report issued Oct. 27, 2014 in Patent Application No. 14180186.0.

Extended European Search Report issued Dec. 23, 2014, in Patent Application No. 14180186.0.

Examination Report as received in the corresponding Australian Patent Application No. 2015203199 dated May 16, 2017.

*Primary Examiner* — Kagnew H Gebreyesus
(74) *Attorney, Agent, or Firm* — Oblon, McClelland, Maier & Neustadt, L.L.P.

(57) ABSTRACT

Provided is an improved nitrile hydratase with improved catalytic activity. Also provided are DNA for coding the improved nitrile hydratase, a recombinant vector that contains the DNA, a transformant that contains the recombinant vector, nitrile hydratase acquired from a culture of the transformant, and a method for producing the nitrile hydratase. Also provided is a method for producing an amide compound that uses the culture or a processed product of the culture. The improved nitrile hydratase contains an amino acid sequence represented by SEQ ID NO: 50 ($GX_1X_2X_3X_4DX_5X_6R$) in a beta subunit, and is characterized in that $X_4$ is an amino acid selected from a group comprising cysteine, aspartic acid, glutamic acid, histidine, isoleucine, lysine, methionine, asparagine, proline, glutamine, serine and threonine.

9 Claims, 18 Drawing Sheets

Alignment results of β-subunit (1)

FIG.2-2

Alignment results of β-subunit (2)

```
Rhodococcus J1-H                 177:GCQ-IYPESSSAG-LGDDPRPLYTVAFSAQELWGDD-GNGKDVVCVDLWEPYLISA----  229
Rhodococcus M8                   177:GCQ-IYPESSSAG-LGDDPRPLYTVAFSAQELWGDD-GNGKDVVCVDLWEPYLISA----  229
Rhodococcus ruber TH             177:GCQ-IYPESSSAG-LGDDPRPLYTVAFSAQELWGDD-GNGKDVVCVDLWEPYLISA----  229
R.pyridinovorans MW3             177:GCQ-IYPESSSAG-LGDDPRPLYTVAFSAQELWGDD-GNGKDVVCVDLWEPYLISA----  229
R.pyridinovorans S85-2           177:GCQ-IYPESSSAG-LGDDPRPLYTVAFSAQELWGDD-GNGKDVVCVDLWEPYLISA----  229
R.pyridinovorans MS-38           177:GCQ-IYPESSSAG-LGDDPRPLYTVAFSAQELWGDD-GNGKDVVCVDLWEPYLISA----  229
Nocardia sp JBRs                 177:GCQ-IYPESSSAG-LGDDPRPLYTVAFSAQELWGDD-GNGKDVVCVDLWEPYLISA----  229
Nocardia YS-2002                 177:GCQ-IYPESSSAG-LGDDPRPLYTVAFSAQELWGDD-GNGKDVVCVDLWEPYLISA----  229
R.rhodocrous ATCC39384           177:GCQ-IYPESSSAG-LGDDPRPLYTVAFSAQELWGDD-GNGKDVVCVDLWEPYLISA----  229
uncultured bacterium SP1         177:GCQ-IYPESSSAG-LGDDPRP---------------------------------------  195
uncultured bacterium BD2         166:-------------------                                          166
Comamonas testosteroni           165:GVF-VTPDTAAHG-KGEHPQHVYTVSFTSVELWGQDASSPKDTIRVDLWDDYLEPA----  218
G.thermoglucosidasius Q6         174:GNH-VFPDSNAHG-DGEAPQPLYNVRFEARELWGGE-AHEKDSLNLDLWDSYLTHA----  226
P.thermophila JCM3095            174:GAY-IYPDTAGNG-LGECPEHLYTVRFTAQELWGPE-GDPNSSVYYDCWEPYIELVDTKA 230
R.rhodocrous Cr4                 174:GAY-VFPDTNAVG-AGEHPEHLYTVRFSATELWGET-ATSNAVNHIDVFEPYLLPA----  226
                                     ... ......... ...................... ...................

Rhodococcus J1-H                 229:----  (SEQ ID NO: 2)     229
Rhodococcus M8                   229:----  (SEQ ID NO: 5)     229
Rhodococcus ruber TH             229:----  (SEQ ID NO: 6)     229
R.pyridinovorans MW3             229:----  (SEQ ID NO: 7)     229
R.pyridinovorans S85-2           229:----  (SEQ ID NO: 8)     229
R.pyridinovorans MS-38           229:----  (SEQ ID NO: 9)     229
Nocardia sp JBRs                 229:----  (SEQ ID NO: 10)    229
Nocardia YS-2002                 229:----  (SEQ ID NO: 11)    229
R.rhodocrous ATCC39384           229:----  (SEQ ID NO: 12)    229
uncultured bacterium SP1         195:----  (SEQ ID NO: 42)    195
uncultured bacterium BD2         166:----  (SEQ ID NO: 43)    166
Comamonas testosteroni           218:----  (SEQ ID NO: 44)    218
G.thermoglucosidasius Q6         226:----  (SEQ ID NO: 45)    226
P.thermophila JCM3095            231:AAA-  (SEQ ID NO: 46)    233
R.rhodocrous Cr4                 226:----  (SEQ ID NO: 47)    226
```

FIG.3

M D G I H D T G G M T G Y G P V P Y Q K D E P F F H Y E W E G R T
L S I L T W M H L K G $X_1$ $X_2$ $X_3$ $X_4$ D $X_5$ $X_6$ R F F R E S M G N E N
Y V N E I R N S Y Y T H W L S A A E R I L V A D K I I T E E E R K
H R V Q E I L E G R Y T D R K P S R K F D P A Q I E K A I E R L H
E P H S L A L P G A E P S F S L G D K I K V K S M N P L G H T R C
P K Y V R N K I G E I V A Y H G C Q I Y P E S S S A G L G D D P R
P L Y T V A F S A Q E L W G D D G N G K D V V C V D L W E P Y L I
S A (SEQ ID NO: 51)

FIG.6-1

```
Rhodococcus J1-H            1:MIKIHDTGGMTGYGPVPYQKDEPFFHYEWEGRTLSILTWMHLKGISWWDKSRFFRESMGN 60
Rhodococcus M8              1:MDGIHDTGGMTGYGPVPYQKDEPFFHYEWEGRTLSILTWMHLKGMSWWDKSRFFRESMGN 60
Rhodococcus ruber TH        1:MIKIHDTGGMTGYGPVPYQKDEPFFHYEWEGRTLSILTWMHLKGMSWWDKSRFFRESMGN 60
R.pyridinovorans MW3        1:MDGIHGTGGMTGYGPVPYQKDEPFFHYEWEGRTLSILTWMHLKGISWWDKSRFPRESMGN 60
R.pyridinovorans S85-2      1:MDGIHDTGGMTGYGPVPYQKDEPFFHYEWEGRTLSILTWMHLKGISWWDKSRFFRESMGN 60
R.pyridinovorans MS-38      1:MDGIHDTGGMTGYGPVPYQKDEPFFHYEWEGRTLSILTWMHLKGISWWDKSRFPRESMGN 60
Nocardia sp JBRs            1:MDGIHDTGGMTGYGPVPYQKDEPFFHYEWEGRTLSILTWMHLKGISWWDKSRFFRESMGN 60
Nocardia sp.YS-2002         1:MDGIHDTGGMTGYGPVPYQKDEPFFHYEWEGRTLSILTWMHLKGMSWWDKSRFFRESMGN 60
R.rhodocrous ATCC39384      1:MDGIHDTGGMTGYGPVPYQKDEPFFHYEWEGRTLSILTWMHLKGMSWWDKSRFFRESMGN 60
uncultured bacterium SP1    1:MIKIHDTGGMTGYGPVPYQKDEPFFHYEWEGRTLSILTWMHLKGISWWDKRFFRESMGN 60
uncultured bacterium BD2    1:MDGIHDTGGMTGYGPVPYQKDEPFFHYEWEGRTLSILTWMHLKGISWWDKSRFPRESMGN 60
Comamonas testosteroni      1:MNGIHDTGGAHGYGPVYREPNEPVPRYDREKTVMSLFPALPANGNPRLDEPRHGIERMNP 60
G.thermoglucosidasius Q6    1:MNGPHDLGGKRDFGPIIKHDQEPLFHEEWEAKVLAMHFALLGQGVINWDEFRBGIERMGY 60
P.thermophila JCM3095       1:MNGVYDYGCTDGLGPINRPADEPVPRAEWEKVAFAMPPATFRAGFMGLDEPRFGIEQMNP 60
R.rhodocrous Cr4            1:MDGIHDLGGRAGLGPVNPEPGEPVFHSRWERSVLIMFPAMALAGAFNLDQFRGAMFQIPP 60
                                 *  **   **    **   **   **          *   *  *    *

Rhodococcus J1-H           61:ENYVNEIRNSYYTHWLSAAERILVADKIITEEERKHRVQ----EILEGRYTDRKPSRKFDP 117
Rhodococcus M8             61:ENYVNEIRNSYYTHWLSAAERILVADKIITEEERKHRVQ----EILEGRYTDRNPSRKFDP 117
Rhodococcus ruber TH       61:ENYVNEIRNSYYTHWLSAAERILVADKIITEEERKHRVQ----EILEGRYTDRNPSRKFDP 117
R.pyridinovorans MW3       61:ENYVNEIRNSYYTHWLSAAERILVADKIITEEERKHRVQ----EILEGRYTDRKPSRKFDP 117
R.pyridinovorans S85-2     61:ENYVNEIRNSYYTHWLSAAERILVADKIITEEERKHRVQ----EILEGRYTDRKPSRKFDP 117
R.pyridinovorans MS-38     61:ENYVNEIRNSYYTHWLSAAERILVADKIITEEERKHRVQ----EILEGRYTDRKPSRKFDP 117
Nocardia sp JBRs           61:ENYVNEIRNSYYTHWLSAAERILVADKIITEEERKHRVQ----EILEGRYTDRNPSRKFDP 117
Nocardia sp.YS-2002        61:ENYVNEIRNSYYTHWLSAAERILVADKIITEEERKHRVQ----EILEGRYTDRNPSRKFDP 117
R.rhodocrous ATCC39384     61:ENYVNEIRNSYYTHWLSAAERILVADKIITEEERKHRVQ----EILEGRYTDRNPSRKFDP 117
uncultured bacterium SP1   61:ENYVNEIRNSYYTHWLSAAERILVADKIITEEERKHRVQ----EILEGRYTDRKPSRKFDP 117
uncultured bacterium BD2   61:ENYVDEIRNSYYTHWLSAAERILVADKIITEEERKHRVQ----EILEGRYTDRKPSRKFDP 117
Comamonas testosteroni     61:IDY----LKGTYYEHWIHSIEILLVEKKYLTATEL----------ATGRASGKTATPYLTP 107
G.thermoglucosidasius Q6   61:YYY----LTSSYYEHWLASLETYLAEKNIINSEQYRKRIR----EIEYGMSVPVSERPELKE 114
P.thermophila JCM3095      61:AEY----LESPYYWDWIRTYIHHGVRTGKIDLEELLERRIQYYRENPDAPLPEHEQKPLI- 116
R.rhodocrous Cr4           61:HDY----LTSQYYEHWMHAMIHYGIEAGIFDPNELDRRTQYYLEHPGED-PPLRGDPGLY- 115
                                  *          **  **

Rhodococcus J1-H          118:AQIEKAIERLHEPHSLALPGAEPSFSLGDKIKVKSM-NPLGHTRCPKYVRNKIGEIVAYH 176
Rhodococcus M8            118:AEIEKAIERLHEPHSLALPGAEPSFSLGDKVKVKNM-NPLGHTRCPKYVRNKIGEIVTSH 176
Rhodococcus ruber TH      118:AEIEKAIERLHEPHSLALPGAEPSFSLGDKVKVKNM-NPLGHTRCPKYVRNKIGEIVTSH 176
R.pyridinovorans MW3      118:AQIEKAIERLHEPHSLALPGAEPSFSLGDKIKVKSM-NPLGHTRCPKYVRNKIGEIVTYH 176
R.pyridinovorans S85-2    118:AQIEKAIERLHEPHSLALPGAEPSFSLGDKIKVKSM-NPLGHTRCPKYVRNKIGEIVTYH 176
R.pyridinovorans MS-38    118:AQIEKAIERLHEPHSLALPGAEPSFSLGDKIKVKSM-NPLGHTRCPKYVRNKIGEIVTYH 176
Nocardia sp JBRs          118:AEIEKAIERLHEPHSLALPGAEPSFSLGDKVKVKNM-NPLGHTRCPKYVRNKIGEIVTSH 176
Nocardia sp.YS-2002       118:AEIEKAIERLHEPHSLALPGAEPSFSLGDKVKVKNM-NPLGHTRCPKYVRNKIGEIVTSH 176
R.rhodocrous ATCC39384    118:AEIEKAIERLHEPHSLVLPGAEPSFSLGDKVKVKNM-NPLGHTRCPKYVRNKIGEIVTSH 176
uncultured bacterium SP1  118:AQIEKAIERLHEPHSLALPGAEPSFSLGDKIKVKSM-NPLGHTRCPKYVRNKIGEIVAYH 176
uncultured bacterium BD2  118:AQIEKAIERLHEPHSLALPGAEPSFSLGDKNQSEEY-EPAGTHTVPEICA---------- 166
Comamonas testosteroni    108:AIVDGLLSTG---ASAAREEGARARFAVGDKVRVLNK-NPVGHTRMPRYIRGKVGTYYIDH 164
G.thermoglucosidasius Q6  115:SLLSEVIYGIKISSERRESTVSPRFRPGDRRVRVKHF-YTRKHIRCFQYVMGKYGVVELLH 173
P.thermophila JCM3095     117:EPVNQAVYGG---LPASREVDRPPKFKEGD-VVRPSIASPKGHARRARYVRGKTGTYYKIHI 173
R.rhodocrous Cr4          116:ETISQLIMHG---ADYKRPTDAEGVPAVGDKVVVRSDASPNTHTRKACYIRGRTGEIVAAH 173
                                                              *  **
```

FIG.6-2

```
Rhodococcus J1-H            177:GCQ-IYPESSSAG-LGDDPRPLYTVAFSAQELWGDD-GNGKDVVCVDLWEPYLISA------ 229
Rhodococcus M8              177:GCQ-IYPESSSAG-LGDDPKPLYTVAFSAQELWGDD-GNGKDVVCVDLWEPYLISA------ 229
Rhodococcus ruber TH        177:GCQ-IYPESSSAG-LGDDPRPLYTVAFSAQELWGDD-GNGKDVVCVDLWEPYLISA------ 229
R.pyridinovorans MW3        177:GCQ-IYPESSSAG-LGDDPRPLYTVAFSAQELWGDD-GNGKDVVCVDLWEPYLISA------ 229
R.pyridinovorans S85-2      177:GCQ-IYPESSSAG-LGDDPRPLYTVAFSAQELWGDD-GNGKDVVCVDLWEPYLISA------ 229
R.pyridinovorans MS-38      177:GCQ-IYPESSSAG-LGDDPRPLYTVAFSAQELWGDD-GNGKDVVCVDLWEPYLISA------ 229
Nocardia sp JBRs            177:GCQ-IYPESSSAG-LGDDPRPLYTVAFSAQELWGDD-GNGKDVVCVDLWEPYLISA------ 229
Nocardia sp.YS-2002         177:GCQ-IYPESSSAG-LGDDPRPLYTVAFSAQELWGDD-GNGKDVVCVDLWEPYLISA------ 229
R.rhodocrous ATCC39384      177:GCQ-IYPESSSAG-LGDDPKPLYTVAFSAQELWGDD-GNGKDVVCVDLWEPYLISA------ 229
uncultured bacterium SP1    177:GCQ-IYPESSSAG-LGDDPRP------------------------------------------ 195
uncultured bacterium BD2    166:-------------------------------------------------------------- 166
Comamonas testosteroni      166:GVF-VTPDTAAHG-KGEHPQHVYTVSFTSVELWGQDASSPKDTIRVDLWDDYLEPA------ 218
G.thermoglucosidasius Q6    174:GNH-VFPDSNAHG-DGEAPQPLYNVRFEARELWGGE-AHEKDSLNLDLWDSYLTHA------ 226
P.thermophila JCM3095      174:GAY-IYPDTAGNG-LGECPEHLYTVRFTAQELWGPE-GDPNSSVYYDCWEPYIELVDTKA 230
R.rhodocrous Cr4            174:GAY-VFPDTNAVG-AGERPEHLYTVRFSATELWGET-ATSNAVNHIDVFEPYLLPA------ 226
                                ... . ....... ....................... ......... ........

Rhodococcus J1-H            229:------   (SEQ ID NO: 2)                                      229
Rhodococcus M8              229:------   (SEQ ID NO: 19)                                     229
Rhodococcus ruber TH        229:------   (SEQ ID NO: 20)                                     229
R.pyridinovorans MW3        229:------   (SEQ ID NO: 21)                                     229
R.pyridinovorans S85-2      229:------   (SEQ ID NO: 22)                                     229
R.pyridinovorans MS-38      229:------   (SEQ ID NO: 23)                                     229
Nocardia sp JBRs            229:------   (SEQ ID NO: 24)                                     229
Nocardia sp.YS-2002         229:------   (SEQ ID NO: 25)                                     229
R.rhodocrous ATCC39384      229:------   (SEQ ID NO: 26)                                     229
uncultured bacterium SP1    195:------   (SEQ ID NO: 27)                                     195
uncultured bacterium BD2    166:------   (SEQ ID NO: 28)                                     166
Comamonas testosteroni      218:------   (SEQ ID NO: 29)                                     218
G.thermoglucosidasius Q6    226:------   (SEQ ID NO: 30)                                     226
P.thermophila JCM3095      231:AAA-     (SEQ ID NO: 31)                                     233
R.rhodocrous Cr4            226:------   (SEQ ID NO: 32)                                     226
```

FIG.7

MDGIHDTGGMTGYGPVPYQKDEPFFHYEWE$X_1X_2X_3X_4X_5X_6$
$X_7X_8X_9X_{10}X_{11}X_{12}X_{13}X_{14}X_{15}X_{16}X_{17}X_{18}$DKSRFFRESMGNENY
VNEIRNSYYTHWLSAAERILVADKIITEEERKHRVQEIL
EGRYTDRKPSRKFDPAQIEKAIERLHEPHSLALPGAEPS
FSLGDKIKVKSM−NPLGHTRCPKYVRNKIGEIVAYHGCQ
IYPESSSAGLGDDPRPLYTVAFSAQELWGDDGNGKDVVC
VDLWEPYLISA (SEQ ID NO: 82)

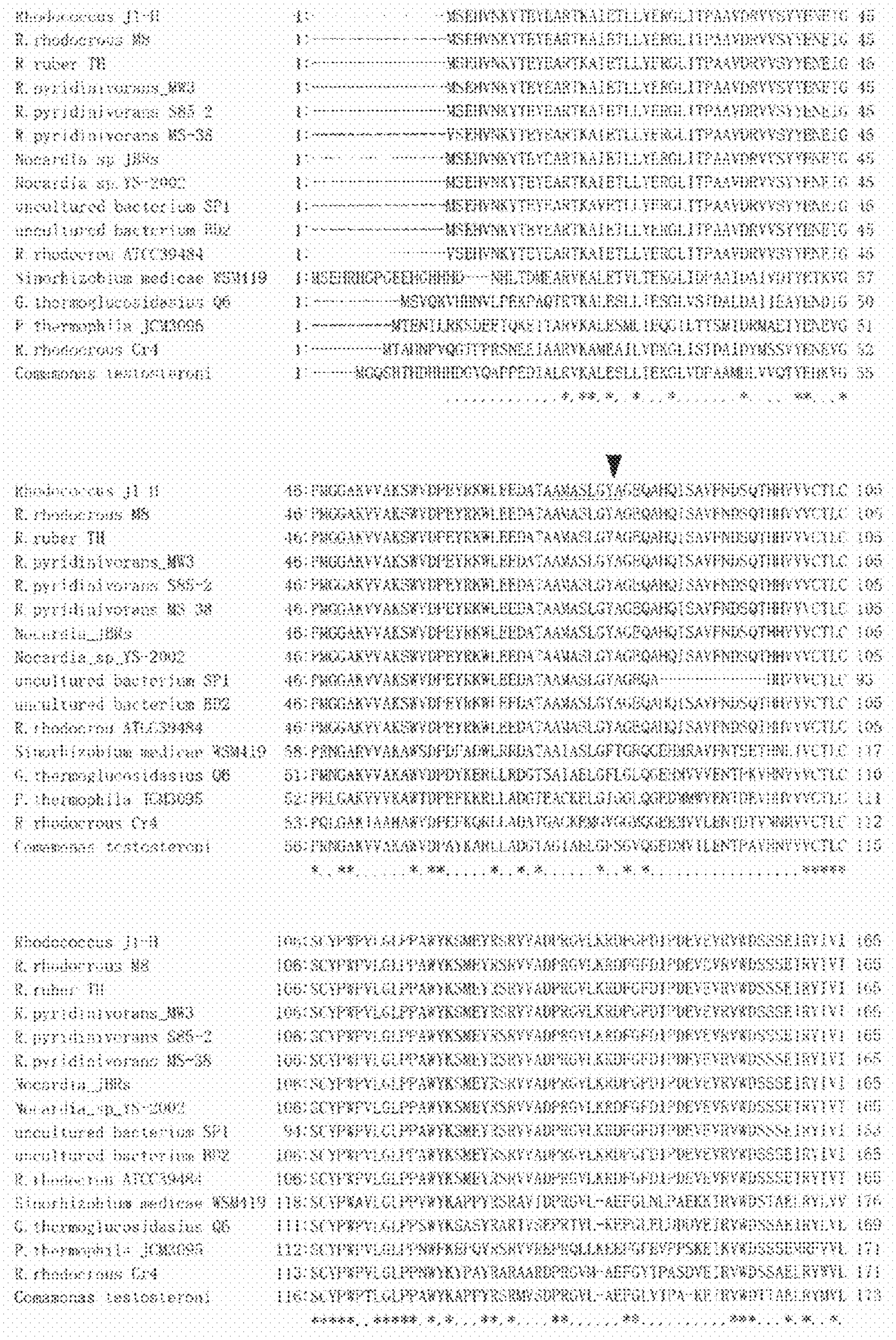

FIG.8-1

```
Rhodococcus j1-H              1:-----------------MSEHVNKYTEYEARTKALETLLYERGLITPAAVDRVVSYYENEIG  45
R. rhodocrous M8              1:-----------------MSEHVNKYTEYEARTKALETLLYERGLITPAAVDRVVSYYENEIG  45
R. ruber TH                   1:-----------------MSEHVNKYTEYEARTKALETLLYERGLITPAAVDRVVSYYENEIG  45
R. pyridinivorans_MW3         1:-----------------MSEHVNKYTEYEARTKALETLLYERGLITPAAVDRVVSYYENEIG  45
R. pyridinivorans S85-2       1:-----------------MSEHVNKYTEYEARTKALETLLYERGLITPAAVDRVVSYYENEIG  45
R. pyridinivorans MS-38       1:------------------VSEHVNKYTEYEARTKALETLLYERGLITPAAVDRVVSYYENEIG  46
Nocardia_sp_JBRs              1:-----------------MSEHVNKYTEYEARTKALETLLYERGLITPAAVDRVVSYYENEIG  45
Nocardia_sp_YS-2002           1:-----------------MSEHVNKYTEYEARTKALETLLYERGLITPAAVDRVVSYYENEIG  45
uncultured bacterium SP1      1:-----------------MSEHVNKYTEYEARTKAVETLLYERGLITPAAVDRVVSYYENEIG  46
uncultured bacterium BD2      1:-----------------MSEHVNKYTEYEARTKALETLLYERGLITPAAVDRVVSYYENEIG  45
R. rhodocrous ATCC39484       1:------------------VSEHVNKYTEYEARTKALETLLYERGLITPAAVDRVVSYYENEIG  46
Sinorhizobium medicae WSM419  1:MSEHRHCPCEEHCHHHD----NHLTDMEARVKALETVLTEKGLIDFAAIDAIVDYYETKVG  37
G. thermoglucosidasius Q6     1:------------MSVQRVHHNVLPEKPAQTRTKALESLLIEKGLVSFDALDAIHAYENDIG  50
P. thermophila JCM3095        1:------------MTENILRKSDEFTQKEITARVKALESMLIEKGLTTSMIDRNAEIYENEVG  51
R. rhodocrous Cr4             1:------------MTAHNPVQGITPSNEEIAARVKAMEAILVEKGLISIPAIPYMSSVYENEVG  52
Comamonas testosteroni        1:---------MKQGSHTHDHHHDCYQAFPEDIALKVKALESLLIEKGLVDFAAMELVVQTYHRKVG  55
                                                     *.**.*.*...*........*..**..*

                                                              ▼
Rhodococcus j1-H             46:PNGGAKVVAKSNYDPEYRKWLEEDATAAMASLGYAGEQAHQISAVFNDSQTHHFVVCTLC 105
R. rhodocrous M8             46:PNGGAKVVAKSNYDPEYRKWLEEDATAAMASLGYAGEQAHQISAVFNDSQTHHFVVCTLC 105
R. ruber TH                  46:PNGGAKVVAKSNYDPEYRKWLEEDATAAMASLGYAGEQAHQISAVFNDSQTHHFVVCTLC 105
R. pyridinivorans_MW3        46:PNGGAKVVAKSNYDPEYRKWLEEDATAAMASLGYAGEQAHQISAVFNDSQTHHFVVCTLC 105
R. pyridinivorans S85-2      46:PNGGAKVVAKSNYDPEYRKWLEEDATAAMASLGYAGEQAHQISAVFNDSQTHHFVVCTLC 105
R. pyridinivorans MS-38      47:PNGGAKVVAKSNYDPEYRKWLEEDATAAMASLGYAGEQAHQISAVFNDSQTHHFVVCTLC 106
Nocardia_JBRs                46:PNGGAKVVAKSNYDPEYRKWLEEDATAAMASLGYAGEQAHQISAVFNDSQTHHFVVCTLC 105
Nocardia_sp_YS-2002          46:PNGGAKVVAKSNYDPEYRKWLEEDATAAMASLGYAGEQAHQISAVFNDSQTHHFVVCTLC 105
uncultured bacterium SP1     47:PNGGAKVVAKSNYDPEYRKWLEEDATAAMASLGYAGEQA------------HHFVVCTLC 93
uncultured bacterium BD2     46:PNGGAKVVAKSNYDPEYRKWLEEDATAAMASLGYAGEQAHQISAVFNDSQTHHFVVCTLC 105
R. rhodocrous ATCC39484      47:PNGGAKVVAKSNYDPEYRKWLEEDATAAMASLGYAGEQAHQISAVFNDSQTHHFVVCTLC 106
Sinorhizobium medicae WSM419 38:PNNGAKVVAKASDPDFADWLRRDATAAIASLGFTGKQEHRRAVFNTSETHNLVVCTLC 117
G. thermoglucosidasius Q6    51:PNNGAKVVAKANYDPDYKRRLLKDGTSAIAELGFLGLQKEHNVVVENTPKVHNYVVCTLC 110
P. thermophila JCM3095       52:PHLGAKVVRKATDPEPRKRLLADGTEACKELGJQGLQKGPDMMYRNTDEVHRVVCTLC 111
R. rhodocrous Cr4            53:PQLGAKIAAMAKVDPEFRQKLLADATGACKRMKVGHGKKEEVYLENTDTVNHRVVCTLC 112
Comamonas testosteroni       56:PNNGAKVVAKAKVDPAYKARLLADDTAHIARLGHSVQREDMVILENTPAVENVVVCTLC 115
                                *.**..........*..*.*..........*.,*.*.............******

Rhodococcus j1-H            106:SCYPNPVLGLPPAWYKSMEYRSRVVAUPKGVLKRUFGFDIPDEVEVRVKDSSSEIRYIVI 165
R. rhodocrous M8            106:SCYPNPVLGLPPAWYKSMEYRSRVVAUPKGVLKRUFGFDIPDEVEVRVKDSSSEIRYIVI 165
R. ruber TH                 106:SCYPNPVLGLPPAWYKSMEYRSRVVAUPKGVLKRUFGFDIPDEVEVRVKDSSSEIRYIVI 165
R. pyridinivorans_MW3       106:SCYPNPVLGLPPAWYKSMEYRSRVVAUPKGVLKRUFGFDIPDEVEVRVKDSSSEIRYIVI 165
R. pyridinivorans S85-2     106:SCYPNPVLGLPPAWYKSMEYRSRVVAUPKGVLKRUFGFDIPDEVEVRVKDSSSEIRYIVI 165
R. pyridinivorans MS-38     107:SCYPNPVLGLPPAWYKSMEYRSRVVAUPKGVLKRUFGFDIPDEVEVRVKDSSSEIRYIVI 166
Nocardia_JBRs               106:SCYPNPVLGLPPAWYKSMEYRSRVVAUPKGVLKRUFGFDIPDEVEVRVKDSSSEIRYIVI 165
Nocardia_sp_YS-2002         106:SCYPNPVLGLPPAWYKSMEYRSRVVAUPKGVLKRUFGFDIPDEVEVRVKDSSSEIRYIVI 165
uncultured bacterium SP1     94:SCYPNPVLGLPPAWYKSMEYRSRVVAUPKGVLKRUFGFDIPDEVEVRVKDSSSEIRYIVI 153
uncultured bacterium BD2    106:SCYPNPVLGLPPAWYKSMEYRSRVVAUPKGVLKRUFGFDIPDEVEVRVKDSSSEIRYIVI 165
R. rhodocrous ATCC39484     107:SCYPNPVLGLPPAWYKSMEYRSRVVAUPKGVLKRUFGFDIPDEVEVRVKDSSSEIRYIVI 166
Sinorhizobium medicae WSM419 118:SCYPNAVLGLPPYWYKAPPYRSRAVIDPRGVL-AEFGLNLPAEKKIRVVDSTAELRYLYV 176
G. thermoglucosidasius Q6   111:SCYPNPVLGLPPSNYKGASYRAKVYSPPRTVL-KEPGLRLIRDQYEIRVKDNSAEIRYLAL 169
P. thermophila JCM3095      112:SCYPNPVLGLITNWFKEPGYKSRVYRPGGLAKERGFEVPPSKEIRVKDSSENRFYVL 171
R. rhodocrous Cr4           113:SCYPNPVLGLPPNNYKPAYRARAARDPRGVN-AEFGYTPASDVEIRVKDSSAELRVVVL 171
Comamonas testosteroni      116:SCYPNPTLGLPPAWYKAPTYRSRMVSDPRGVL-AEFGLYIPA-KEIRVKDPTAELRYMVL 173
                                ******..*****.*.*....**.**.*.......**.........***...*..*.*
```

FIG.8-2

| | | | |
|---|---|---|---|
| Rhodococcus J1-H | 166:PERPAGTDGWSEEELTKLVSRDSMIGVSNALTPQEVIV | (SEQ ID NO: 4) | 203 |
| R. rhodocrous M8 | 166:PERPAGTDGWSEDELAKLVSRDSMIGVSNALTPQEVIV | (SEQ ID NO: 105) | 203 |
| R. ruber TH | 166:PERPAGTDGWSEDELAKLVSRDSMIGVSNALTPQEVIV | (SEQ ID NO: 106) | 203 |
| R. pyridinivorans_MW3 | 166:PERPAGTDGWSEEELTKLVSRDSMIGVSNALTPQEVIV | (SEQ ID NO: 107) | 203 |
| R. pyridinivorans S85-2 | 166:PERPAGTDGWSEEELTKLVSRDSMIGVSNALTPQEVIV | (SEQ ID NO: 108) | 203 |
| R. pyridinivorans MS-38 | 166:PERPAGTDGWSEEELTKLVSRDSMIGVSNALTPQEVIV | (SEQ ID NO: 121) | 203 |
| Nocardia_JBRs | 166:PERPAGTDGWSEDELAKLVSRDSMIGVSNALTPQEVIV | (SEQ ID NO: 109) | 203 |
| Nocardia_sp_YS-2002 | 166:PERPAGTDGWSEDELAKLVSRDSMIGVSNALTPQEVIV | (SEQ ID NO: 110) | 203 |
| uncultured bacterium SP1 | 154:PERPAGTDGWSEEELTKLVSRDSIIGV----------- | (SEQ ID NO: 112) | 180 |
| uncultured bacterium BD2 | 166:PERPAGTDGWSEEELTKLVSRDSMIGVSNALTPQEVIV | (SEQ ID NO: 111) | 203 |
| R. rhodocrou ATCC39484 | 166:PERPAGTDGWSEDELAKLVSRDSMIGVSNALTPQEVIV | (SEQ ID NO: 122) | 203 |
| Sinorhizobium medicae WSM419 | 177:PERPAATDDLGEDALAKLVTRDSMIGTGLALSPEAFR- | (SEQ ID NO: 123) | 213 |
| G. thermoglucosidasius Q6 | 170:PERPAGTEGWSEEELAKLVTRDSMIGVAKIKSPVKK-- | (SEQ ID NO: 124) | 205 |
| P. thermophila JCM3095 | 172:PQRPAGTDGWSEEELATLVTRESMIGVEPAKAVA---- | (SEQ ID NO: 113) | 205 |
| R. rhodocrous Cr4 | 172:PQRPAGTENFTEEQLAALVTRDSLIGVSVPTAPNKA-- | (SEQ ID NO: 114) | 207 |
| Comamonas testosteroni | 174:PERPAGTEAYSEEQLAELVTRDSMIGTGLPIQPTPSH- | (SEQ ID NO: 125) | 210 |
| | *.***.*....*..*..**.*.*.**............ | | |

FIG.9

M S E H V N K Y T E Y E A R T K A I E T L L Y E R G L I T P A A V D R V V S Y
Y E N E I G P M G G A K V V A K S W V D P E Y R K W L E E D A T A <u>A $X_1$ $X_2$ $X_3$ $X_4$ G $X_5$ $X_6$ G $X_7$ $X_8$</u> A H Q I S A V F N D S Q T H H V V V C T L C S C Y P W P V L
G L P P A W Y K S M E Y R S R V V A D P R G V L K R D F G F D I P D E V E V R
V W D S S S E I R Y I V I P E R P A G T D G W S E E E L T K L V S R D S M I G
V S N A L T P Q E V I V (SEQ ID NO: 120)

FIG.10-1

```
Rhodococcus J1-H                1:-----------------MSEHVNKYTEYEARTKAIETLLYERGLITPAAVDRVVSYYENEIG 45
R.rhodocrous M8                 1:-----------------MSEHVNKYTEYEARTKAIETLLYERGLITPAAVDRVVSYYENEIG 45
R.ruber TH                      1:-----------------MSEHVNKYTEYEARTKAIETLLYERGLITPAAVDRVVSYYENEIG 45
R.pyridinivorans_MW3            1:-----------------MSEHVNKYTEYEARTKAIETLLYERGLITPAAVDRVVSYYENEIG 45
R.pyridinivorans S85-2          1:-----------------MSEHVNKYTEYEARTKAIETLLYERGLITPAAVDRVVSYYENEIG 45
R.pyridinivorans MS-38          1:-----------------VSEHVNKYTEYEARTKAIETLLYERGLITPAAVDRVVSYYENEIG 45
Nocardia sp JBRs                1:-----------------MSEHVNKYTEYEARTKAIETLLYERGLITPAAVDRVVSYYENEIG 45
Nocardia YS-2002                1:-----------------MSEHVNKYTEYEARTKAIETLLYERGLITPAAVDRVVSYYENEIG 45
uncultured bacterium SP1        1:-----------------MSEHVNKYTEYEARTKAVETLLYERGLITPAAVDRVVSYYENEIG 45
uncultured bacterium BD2        1:-----------------MSEHVNKYTEYEARTKAIETLLYERGLITPAAVDRVVSYYENEIG 45
R.rhodocrous ATCC39484          1:-----------------VSEHVNKYTEYEARTKAIETLLYERGLITPAAVDRVVSYYENEIG 45
Sinorhizobium medicae WSM419    1:MSEHRHGPGEEHGHHHD-----NHLTDMEARVKALETVLTERGLIDPAAIDAIVDTYETKVG 57
G.thermoglucosidasius Q6        1:-----------MSVQKVHHNVLPEKPAQTRTKALESLLIESGLVSTDALDAIIEAYENDIG 50
P.thermophila JCM3095           1:----------MTENILRKSDEEIQKEITARVKALESMLIEQGILTTSMIDRMAEIYENEVG 51
R.rhodocrous Cr4                1:---------MTAHNPVQGTPPRSNEEIAARVKAMEAILVDKGLISTDAIDYMSSVYENEVG 52
Comamonas testosteroni          1:------MGQSHTHDHHHDGYQAPPEDIALRVKALESLLIEKGLVDPAAMDLVVQTYEHKVG 55
                                                  ..............*.** *..*...*.......*.....**...*

Rhodococcus J1-H               46:PMGGAKVVAKSWVDPEYRKWLEEDATAAMASLGYAGEQAHQISAVFNDSQTHHVVVCTLC 105
R.rhodocrous M8                46:PMGGAKVVAKSWVDPEYRKWLEEDATAAMASLGYAGEQAHQISAVFNDSQTHHVVVCTLC 105
R.ruber TH                     46:PMGGAKVVAKSWVDPEYRKWLEEDATAAMASLGYAGEQAHQISAVFNDSQTHHVVVCTLC 105
R.pyridinivorans_MW3           46:PMGGAKVVAKSWVDPEYRKWLEEDATAAMASLGYAGEQAHQISAVFNDSQTHHVVVCTLC 105
R.pyridinivorans S85-2         46:PMGGAKVVAKSWVDPEYRKWLEEDATAAMASLGYAGEQAHQISAVFNDSQTHHVVVCTLC 105
R.pyridinivorans MS-38         46:PMGGAKVVAKSWVDPEYRKWLEEDATAAMASLGYAGEQAHQISAVFNDSQTHHVVVCTLC 105
Nocardia sp JBRs               46:PMGGAKVVAKSWVDPEYRKWLEEDATAAMASLGYAGEQAHQISAVFNDSQTHHVVVCTLC 105
Nocardia YS-2002               46:PMGGAKVVAKSWVDPEYRKWLEEDATAAMASLGYAGEQAHQISAVFNDSQTHHVVVCTLC 105
uncultured bacterium SP1       46:PMGGAKVVAKSWVDPEYRKWLEEDATAAMASLGYAGEQA------------HHVVVCTLC 93
uncultured bacterium BD2       46:PMGGAKVVAKSWVDPEYRKWLEEDATAAMASLGYAGEQAHQISAVFNDSQTHHVVVCTLC 105
R.rhodocrous ATCC39484         46:PMGGAKVVAKSWVDPEYRKWLEEDATAAMASLGYAGEQAHQISAVFNDSQTHHVVVCTLC 105
Sinorhizobium medicae WSM419   58:PRNGAKVVAKAWSDPDFADWLRRDATAAIASLGFTGRQGEHMRAVFNTSEIHNLIVCTLC 117
G.thermoglucosidasius Q6       51:PMNGAKVVAKAWVDPDYKERLLRDGTSAIAELGFLGLQGEHMVVVENTPKVHNVVVCTLC 110
P.thermophila JCM3095          52:PHLGAKVVVKAWTDPEFKKRLLADGTEACKELGIGGLQGEDMMWVENTDEVHHVVVCTLC 111
R.rhodocrous Cr4               53:PQLGAKIAAHAWVDPEFKQRLLADATGACKEMGVGGMQGEEMVVLENTDTVNNMVVCTLC 112
Comamonas testosteroni         56:PRNGAKVVAKAWVDPAYKARLLADGTAGIAELGFSGVQGEDMVILENTPAVHNVVVCTLC 115
                                   *..**.....*.**....*.*.*.....*..*.*..............*****

Rhodococcus J1-H              106:SCYPWPVLGLPPAWYKSMEYRSRVVADPRGVLKRDFGFDIPDEVEVRVWDSSSEIRYIVI 165
R.rhodocrous M8               106:SCYPWPVLGLPPAWYKSMEYRSRVVADPRGVLKRDFGFDIPDEVEVRVWDSSSEIRYIVI 165
R.ruber TH                    106:SCYPWPVLGLPPAWYKSMEYRSRVVADPRGVLKRDFGFDIPDEVEVRVWDSSSEIRYIVI 165
R.pyridinivorans_MW3          106:SCYPWPVLGLPPAWYKSMEYRSRVVADPRGVLKRDFGFDIPDEVEVRVWDSSSEIRYIVI 165
R.pyridinivorans S85-2        106:SCYPWPVLGLPPAWYKSMEYRSRVVADPRGVLKRDFGFDIPDEVEVRVWDSSSEIRYIVI 165
R.pyridinivorans MS-38        106:SCYPWPVLGLPPAWYKSMEYRSRVVADPRGVLKRDFGFDIPDEVEVRVWDSSSEIRYIVI 165
Nocardia sp JBRs              106:SCYPWPVLGLPPAWYKSMEYRSRVVADPRGVLKRDFGFDIPDEVEVRVWDSSSEIRYIVI 165
Nocardia YS-2002              106:SCYPWPVLGLPPAWYKSMEYRSRVVADPRGVLKRDFGFDIPDEVEVRVWDSSSEIRYIVI 165
uncultured bacterium SP1       94:SCYPWPVLGLPPAWYKSMEYRSRVVADPRGVLKRDFGFDIPDEVEVRVWDSSSEIRYIVI 153
uncultured bacterium BD2      106:SCYPWPVLGLPPAWYKSMEYRSRVVADPRGVLKRDFGFDIPDEVEVRVWDSSSEIRYIVI 165
R.rhodocrous ATCC39484        106:SCYPWPVLGLPPAWYKSMEYRSRVVADPRGVLKRDFGFDIPDEVEVRVWDSSSEIRYIVI 165
Sinorhizobium medicae WSM419  118:SCYPWAVLGLPPVWYKAPPYRSRAVIDPRGVL-AEFGLNLPAEKKIRVWDSTAELRYLVV 176
G.thermoglucosidasius Q6      111:SCYPWPVLGLPPSWYKSASYKARIVSEPRTVL-KEFGLELDDDVEIRVWDSSAEIRYLVL 169
P.thermophila JCM3095         112:SCYPWPVLGLPPNWFKEPQYRSRVVREPRQLLKEEFGFEVPPSKEIKVWDSSSEMRFVVL 171
R.rhodocrous Cr4              113:SCYPWPVLGLPPNWYKYPAYRARAARDPRGVM-AEFGYTPASDVEIRVWDSSAELRYWVL 171
Comamonas testosteroni        116:SCYPWPTLGLPPAWYKAPPYRSRMVSDPRGVL-AEFGLVIPA-KEIRVWDTTAELRYMVL 173
                                   *****..*****.*.*...**.*....**.....**..........***...*.*..*
```

FIG.10-2

| | | | |
|---|---|---|---|
| Rhodococcus J1-H | 166:PERPAGTDGWSEEELTKLVSRDSMIGVSNALTPQEVIV | (SEQ ID NO: 4) | 203 |
| R. rhodocrous M8 | 166:PERPAGTDGWSEDELAKLVSRDSMIGVSNALTPQEVIV | (SEQ ID NO: 105) | 203 |
| R. ruber TH | 166:PERPAGTDGWSEDELAKLVSRDSMIGVSNALTPQEVIV | (SEQ ID NO: 106) | 203 |
| R. pyridinivorans MW3 | 166:PERPAGTDGWSEEELTKLVSRDSMIGVSNALTPQEVIV | (SEQ ID NO: 107) | 203 |
| R. pyridinivorans S85-2 | 166:PERPAGTDGWSEEELTKLVSRDSMIGVSNALTPQEVIV | (SEQ ID NO: 108) | 203 |
| R. pyridinivorans MS-38 | 166:PERPAGTDGWSEEELTKLVSRDSMIGVSNALTPQEVIV | (SEQ ID NO: 121) | 203 |
| Nocardia_JBRs | 166:PERPAGTDGWSEDELAKLVSRDSMIGVSNALTPQEVIV | (SEQ ID NO: 109) | 203 |
| Nocardia_sp_YS-2002 | 166:PERPAGTDGWSEDELAKLVSRDSMIGVSNALTPQEVIV | (SEQ ID NO: 110) | 203 |
| uncultured bacterium SP1 | 154:PERPAGTDGWSEEELTKLVSRDSIIGV----------- | (SEQ ID NO: 112) | 180 |
| uncultured bacterium BD2 | 166:PERPAGTDGWSEEELTKLVSRDSMIGVSNALTPQEVIV | (SEQ ID NO: 111) | 203 |
| R. rhodocrou ATCC39484 | 166:PERPAGTDGWSEDELAKLVSRDSMIGVSNALTPQEVIV | (SEQ ID NO: 122) | 203 |
| Sinorhizobium medicae WSM419 | 177:PERPAATDDLGEDALAKLVTRDSMIGTGLALSPEAFR- | (SEQ ID NO: 123) | 213 |
| G. thermoglucosidasius Q6 | 170:PERPAGTEGWSEEELAKLVTRDSMIGVAKIKSPVKK-- | (SEQ ID NO: 124) | 205 |
| P. thermophila JCM3095 | 172:PQRPAGTDGWSEEELATLVTRESMIGVEPAKAVA---- | (SEQ ID NO: 113) | 205 |
| R. rhodocrous Cr4 | 172:PQRPAGTENFTEEQLAALVTRDSLIGVSVPTAPNKA-- | (SEQ ID NO: 114) | 207 |
| Comamonas testosteroni | 174:PERPAGTEAYSEEQLAELVTRDSMIGTGLPIQPTPSH- | (SEQ ID NO: 125) | 210 |
| | *.***.*....*..*..**.*.*.**............ | | |

FIG.11

M S E H V N K Y T E Y E A R T K A I E T L L Y E R G L I T P A A V D R V V S Y Y E
N E I G P M G G A K V V A K S W V D P E Y R K W L E E D A T A A $\underline{X_1}$ $\underline{X_2}$ $\underline{X_3}$ $\underline{X_4}$ G $\underline{X_5}$
$\underline{X_6}$ G $\underline{X_7}$ Q A H Q I S A V F N D S Q T H H V V V C T L C S C Y P W P V L G L P P A W
Y K S M E Y R S R V V A D P R G V L K R D F G F D I P D E V E V R V W D S S S E I
R Y I V I P E R P A G T D G W S E E E L T K L V S R D S M I G V S N A L T P Q E V
I V (SEQ ID NO: 131)

FIG.12-1

```
Rhodococcus J1-H                 1:---------------MSEHVNKYTEYEARTKAIETLLYERGLITPAAVDRVVSYYENEIG 45
R.rhodocrous M8                  1:---------------MSEHVNKYTEYEARTKAIETLLYERGLITPAAVDRVVSYYENEIG 45
R.ruber TH                       1:---------------MSEHVKKYTEYEARTKAIETLLYERGLITPAAVDRVVSYYENEIG 45
R.pyridinivorans_MW3             1:---------------MSEHVNKYTEYEARTKAIETLLYERGLITPAAVDRVVSYYENEIG 45
R.pyridinivorans S85-2           1:---------------MSEHVNKYTEYEARTKAIETLLYERGLITPAAVDRVVSYYENEIG 45
R.pyridinivorans MS-38           1:---------------YSEHVKKYTEYEARTKAIETLLYERGLITPAAVDRVVSYYENEIG 45
Nocardia sp JBRs                 1:---------------MSEHVNKYTEYEARTKAIETLLYERGLITPAAVDRVVSYYENEIG 45
Nocardia YS-2002                 1:---------------MSEHVNKYTEYEARTKAIETLLYERGLITPAAVDRVVSYYENEIG 45
uncultured bacterium SP1         1:---------------MSEHVNKYTEYEARTKAVETLLYERGLITPAAVDRVVSYYENEIG 45
uncultured bacterium BD2         1:---------------MSEHVNKYTEYEARTKAIETLLYERGLITPAAVDRVVSYYENEIG 45
R.rhodocrous ATCC39484           1:---------------YSEHVNKYTEYEARTKAIETLLYERGLITPAAVDRVVSYYENEIG 45
Sinorhizobium medicae WSM419     1:MSEHRHGPGFEHGHHHD---NHLTDMEARVKALETVLTEKGLIDPAAIDAIVDTYETKVG 57
G.thermoglucosidasius Q6         1:----------MSVQKVHENVLPEKPAQTRTKALESLLIESGLVSTDALDAIIEAYENDIG 50
P.thermophila JCM3095            1:---------MIENILRKSDEEIQKEITARVKALESMLIEQGILTTSMIDRMAEIYENEVG 51
R.rhodocrous Cr4                 1:--------MTAHNPVQGTFPRSNEEIAARVKAMEAILVDKGLISTDAIDYMSSVYENEVG 52
Comamonas testosteroni           1:-----MGQSHTHDHHHDGYQAPPEDIALRVKALESLLIEKGLVDPAAMDLVVQTYEHKVG 55
                                   ..............*.**.*..*...*.......*.....**...*

Rhodococcus J1-H                46:PMGGAKVVAKSWVDPEYRKWLEEDATAAMASLGYAGEQAHQISAVFNDSQTHHVVVCTLC 105
R.rhodocrous M8                 46:PMGGAKVVAKSWVDPEYRKWLEEDATAAMASLGYAGEQAHQISAVFNDSQTHHVVVCTLC 105
R.ruber TH                      46:PMGGAKVVAKSWVDPEYRKWLEEDATAAMASLGYAGEQAHQISAVFNDSQTHHVVVCTLC 105
R.pyridinivorans_MW3            46:PMGGAKVVAKSWVDPEYRKWLEEDATAAMASLGYAGEQAHQISAVFNDSQTHHVVVCTLC 105
R.pyridinivorans S85-2          46:PMGGAKVVAKSWVDPEYRKWLEEDATAAMASLGYAGEQAHQISAVFNDSQTHHVVVCTLC 105
R.pyridinivorans MS-38          46:PMGGAKVVAKSWVDPEYRKWLEEDATAAMASLGYAGEQAHQISAVFNDSQTHHVVVCTLC 105
Nocardia sp JBRs                46:PMGGAKVVAKSWVDPEYRKWLEEDATAAMASLGYAGEQAHQISAVFNDSQTHHVVVCTLC 105
Nocardia YS-2002                46:PMGGAKVVAKSWVDPEYRKWLEEDATAAMASLGYAGEQAHQISAVFNDSQTHHVVVCTLC 105
uncultured bacterium SP1        46:PMGGAKVVAKSWVDPEYRKWLEEDATAAMASLGYAGEQA------------HHVVVCTLC 93
uncultured bacterium BD2        46:PMGGAKVVAKSWVDPEYRKWLEEDATAAMASLGYAGEQAHQISAVFNDSQTHHVVVCTLC 105
R.rhodocrous ATCC39484          46:PMGGAKVVAKSWVDPEYRKWLEEDATAAMASLGYAGEQAHQISAVFNDSQTHHVVVCTLC 105
Sinorhizobium medicae WSM419    58:PRNGARVVAKAWSDPDFADWLKRDATAAIASLGFTGRQGEHNRAVFNTSETHNLIVCTLC 117
G.thermoglucosidasius Q6        51:PMNGAKVVAKAWVDPDYKERLLRDGTSAIAELGFLGLQGEHMVVVENTPKVHNVVVCTLC 110
P.thermophila JCM3095           52:PHLGAKVVVKAWTDPEFKKRLLADGTEACKELGIGGLQGEDMMWVENTDEVHHVVVCTLC 111
R.rhodocrous Cr4                53:PQLGAKIAAHAWVDPEFKQRLLADATGACKEMGVGGMQGEEMVVLENTDTVNNMVVCTLC 112
Comamonas testosteroni          56:PRNGAKVVAKAWVDPAYKARLLADGTAGIAELGFSGVQGEDMVILENTPAVHNVVVCTLC 115
                                   *..**.....*.**....*..*.*......*..*.*.................*****

Rhodococcus J1-H               106:SCYPWPVLGLPPAWYKSMEYRSRVVADPRGVLKRDFGFDIPDEVEVRVWDSSSEIRYIVI 165
R.rhodocrous M8                106:SCYPWPVLGLPPAWYKSMEYRSRVVADPRGVLKRDFGFDIPDEVEVRVWDSSSEIRYIVI 165
R.ruber TH                     106:SCYPWPVLGLPPAWYKSMEYRSRVVADPRGVLKRDFGFDIPDEVEVRVWDSSSEIRYIVI 165
R.pyridinivorans_MW3           106:SCYPWPVLGLPPAWYKSMEYRSRVVADPRGVLKRDFGFDIPDEVEVRVWDSSSEIRYIVI 165
R.pyridinivorans S85-2         106:SCYPWPVLGLPPAWYKSMEYRSRVVADPRGVLKRDFGFDIPDEVEVRVWDSSSEIRYIVI 165
R.pyridinivorans MS-38         106:SCYPWPVLGLPPAWYKSMEYKSRVVADPRGVLKRDFGFDIPDEVEVRVWDSSSEIRYIVI 165
Nocardia sp JBRs               106:SCYPWPVLGLPPAWYKSMEYRSRVVADPRGVLKKDFGFDIPDEVEVRVWDSSSEIRYIVI 165
Nocardia YS-2002               106:SCYPWPVLGLPPAWYKSMEYKSRVVADPRGVLKRDFGFDIPDEVEVRVWDSSSEIRYIVI 165
uncultured bacterium SP1        94:SCYPWPVLGLPPAWYKSMEYRSRVVADPRGVLKRDFGFDIPDEVEVRVWDSSSEIRYIVI 153
uncultured bacterium BD2       106:SCYPWPVLGLPPAWYKSMEYRSRVVADPRGVLKRDFGFDIPDEVEVRVWDSSSEIRYIVI 165
R.rhodocrous ATCC39484         106:SCYPWPVLGLPPAWYKSMEYKSRVVADPRGVLKRDFGFDIPDEVEVRVWDSSSEIRYIVI 165
Sinorhizobium medicae WSM419   118:SCYPWAVLGLPPVWYKAPPYRSRAVIDPRGVL-AEPGLNLPAEKKIRVWDSTAELRYLVV 176
G.thermoglucosidasius Q6       111:SCYPWPVLGLPPSWYKSASYRARIVSEPRTVL-KEPGLELDDDVEIRVWDSSAEIRYLVL 169
P.thermophila JCM3095          112:SCYPWPVLGLPPNWFKEPQYRSRVVREPRQLLKEEFGFEVPPSKEIKVWDSSSEMRFVVL 171
R.rhodocrous Cr4               113:SCYPWPVLGLPPNWYKYPAYRARAARDPRGVM-AEFGYIPASDVEIRVWDSSAELRYWVL 171
Comamonas testosteroni         116:SCYPWPTLGLPPAWYKAPPYRSRMVSDPRGVL-AEPGLVIPA-KEIRVWDTTAELRYMVL 173
                                   *****.*****.*.*...**.*....**......**.........***...*.*..*.
```

FIG.12-2

```
Rhodococcus J1-H            166:PERPAGTDGWSEEELTKLVSRDSMIGVSNALTPQEVIV   (SEQ ID NO: 4)    203
R. rhodocrous M8            166:PERPAGTDGWSEDELAKLVSRDSMIGVSNALTPQEVIV   (SEQ ID NO: 105)  203
R. ruber TH                 166:PERPAGTDGWSEDELAKLVSRDSMIGVSNALTPQEVIV   (SEQ ID NO: 106)  203
R. pyridinivorans_MW3       166:PERPAGTDGWSEEELTKLVSRDSMIGVSNALTPQEVIV   (SEQ ID NO: 107)  203
R. pyridinivorans S85-2     166:PERPAGTDGWSEEELTKLVSRDSMIGVSNALTPQEVIV   (SEQ ID NO: 108)  203
R. pyridinivorans MS-38     166:PERPAGTDGWSEEELTKLVSRDSMIGVSNALTPQEVIV   (SEQ ID NO: 121)  203
Nocardia_JBRs               166:PERPAGTDGWSEDELAKLVSRDSMIGVSNALTPQEVIV   (SEQ ID NO: 109)  203
Nocardia_sp_YS-2002         166:PERPAGTDGWSEDELAKLVSRDSMIGVSNALTPQEVIV   (SEQ ID NO: 110)  203
uncultured bacterium SP1    154:PERPAGTDGWSEEELTKLVSRDSIIGV------------  (SEQ ID NO: 112)  180
uncultured bacterium BD2    166:PERPAGTDGWSEEELTKLVSRDSMIGVSNALTPQEVIV   (SEQ ID NO: 111)  203
R. rhodocrou ATCC39484      166:PERPAGTDGWSEDELAKLVSRDSMIGVSNALTPQEVIV   (SEQ ID NO: 122)  203
Sinorhizobium medicae WSM419 177:PERPAATDDLGEDALAKLVTRDSMIGTGLAISPEAFR-  (SEQ ID NO: 123)  213
G. thermoglucosidasius Q6   170:PERPAGTEGWSEEELAKLVTRDSMIGVAKIKSPVKK--   (SEQ ID NO: 124)  206
P. thermophila JCM3095      172:PQRPAGTDGWSEEELATLVTRESMIGVEPAKAVA----   (SEQ ID NO: 113)  205
R. rhodocrous Cr4           172:PQRPAGTENFTEEQLAALVTRDSLIGVSVPTAPNKA--   (SEQ ID NO: 114)  207
Comamonas testosteroni      174:PERPAGTEAYSEEQLAELVTRDSMIGTGLPIQPTPSH-   (SEQ ID NO: 125)  210
                                *.***.*....*..*..**.*.*.**..........
```

FIG.13

M S E H V N K Y T E Y E A R T K A I E T L L Y E R G L I T P A A V D R V V S Y Y E
N E I G P M G G A K V V A K S W V D P E Y R K W L E E D A T A A $\underline{X_1}$ $\underline{X_2}$ $\underline{X_3}$ $\underline{X_4}$ G $\underline{X_5}$
$\underline{X_6}$ G $\underline{X_7}$ Q $\underline{X_8}$ $\underline{X_9}$ Q I S A V F N D S Q T H H V V V C T L C S C Y P W P V L G L P P A
W Y K S M E Y R S R V V A D P R G V L K R D F G F D I P D E V E V R V W D S S S E
I R Y I V I P E R P A G T D G W S E E E L T K L V S R D S M I G V S N A L T P Q E
V I V (SEQ ID NO: 135)

SEQUENCE LISTING

```
<160> NUMBER OF SEQ ID NOS: 136

<210> SEQ ID NO 1
<211> LENGTH: 690
<212> TYPE: DNA
<213> ORGANISM: Rhodococcus rhodochrous J1

<400> SEQUENCE: 1

atggatggta tccacgacac aggcggcatg accggatacg gaccggtccc ctatcagaag      60

gacgagccct tcttccacta cgagtgggag ggtcggaccc tgtcaattct gacttggatg     120

catctcaagg gcatatcgtg gtgggacaag tcgcggttct tccgggagtc gatggggaac     180

gaaaactacg tcaacgagat tcgcaactcg tactacaccc actggctgag tgcggcagaa     240
```

```
cgtatcctcg tcgccgacaa gatcatcacc gaagaagagc gaaagcaccg tgtgcaagag    300

atccttgagg gtcggtacac ggacaggaag ccgtcgcgga agttcgatcc ggcccagatc    360

gagaaggcga tcgaacggct tcacgagccc cactccctag cgcttccagg agcggagccg    420

agtttctctc tcggtgacaa gatcaaagtg aagagtatga acccgctggg acacacacgg    480

tgcccgaaat atgtgcggaa caagatcggg gaaatcgtcg cctaccacgg ctgccagatc    540

tatcccgaga gcagctccgc cggcctcggc gacgatcctc gcccgctcta cacggtcgcg    600

ttttccgccc aggaactgtg gggcgacgac ggaaacggga aagacgtagt gtgcgtcgat    660

ctctgggaac cgtacctgat ctctgcgtga                                     690


<210> SEQ ID NO 2
<211> LENGTH: 229
<212> TYPE: PRT
<213> ORGANISM: Rhodococcus rhodochrous J1

<400> SEQUENCE: 2

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225


<210> SEQ ID NO 3
<211> LENGTH: 612
<212> TYPE: DNA
<213> ORGANISM: Rhodococcus rhodochrous J1

<400> SEQUENCE: 3

gtgagcgagc acgtcaataa gtacacggag tacgaggcac gtaccaaggc gatcgaaacc     60
```

```
ttgctgtacg agcgagggct catcacgccc gccgcggtcg accgagtcgt ttcgtactac    120

gagaacgaga tcggcccgat gggcggtgcc aaggtcgtgg ccaagtcctg ggtggaccct    180

gagtaccgca agtggctcga agaggacgcg acggccgcga tggcgtcatt gggctatgcc    240

ggtgagcagg cacaccaaat ttcggcggtc ttcaacgact cccaaacgca tcacgtggtg    300

gtgtgcactc tgtgttcgtg ctatccgtgg ccggtgcttg gtctcccgcc cgcctggtac    360

aagagcatgg agtaccggtc ccgagtggta gcggaccctc gtggagtgct caagcgcgat    420

ttcggtttcg acatccccga tgaggtggag gtcagggttt gggacagcag ctccgaaatc    480

cgctacatcg tcatcccgga acggccggcc ggcaccgacg gttggtccga ggaggagctg    540

acgaagctgg tgagccggga ctcgatgatc ggtgtcagta atgcgctcac accgcaggaa    600

gtgatcgtat ga                                                        612


<210> SEQ ID NO 4
<211> LENGTH: 203
<212> TYPE: PRT
<213> ORGANISM: Rhodococcus rhodochrous J1

<400> SEQUENCE: 4

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200


<210> SEQ ID NO 5
<211> LENGTH: 229
<212> TYPE: PRT
<213> ORGANISM: Rhodococcus rhodochrous M8

<400> SEQUENCE: 5

Met Asp Gly Ile His Asp Thr Gly Gly Met Thr Gly Tyr Gly Pro Val
1               5                   10                  15
```

-continued

```
Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Met Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Asn Pro Ser
            100                 105                 110

Arg Lys Phe Asp Pro Ala Glu Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Val Lys Val Lys Asn Met Asn Pro Leu Gly His Thr Arg
145                 150                 155                 160

Cys Pro Lys Tyr Val Arg Asn Lys Ile Gly Glu Ile Val Thr Ser His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225


<210> SEQ ID NO 6
<211> LENGTH: 229
<212> TYPE: PRT
<213> ORGANISM: Rhodococcus ruber TH

<400> SEQUENCE: 6

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Met Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Asn Pro Ser
            100                 105                 110

Arg Lys Phe Asp Pro Ala Glu Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Val Lys Val Lys Asn Met Asn Pro Leu Gly His Thr Arg
145                 150                 155                 160
```

```
Cys Pro Lys Tyr Val Arg Ser Lys Ile Gly Glu Ile Val Thr Ser His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Ala Asp Leu Trp Glu Pro
    210                 215                 220

Tyr Leu Ile Ser Ala
225


<210> SEQ ID NO 7
<211> LENGTH: 229
<212> TYPE: PRT
<213> ORGANISM: Rhodococcus pyridinovorans MW33

<400> SEQUENCE: 7

Met Asp Gly Ile His Gly Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Glu His Thr Arg
145                 150                 155                 160

Cys Pro Lys Tyr Val Arg Asn Lys Ile Gly Glu Ile Val Thr Tyr His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225


<210> SEQ ID NO 8
<211> LENGTH: 229
<212> TYPE: PRT
<213> ORGANISM: Rhodococcus pyridinivorans S85-2

<400> SEQUENCE: 8

Met Asp Gly Ile His Gly Thr Gly Gly Met Thr Gly Tyr Gly Pro Val
1               5                   10                  15
```

-continued

```
Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Glu His Thr Arg
145                 150                 155                 160

Cys Pro Lys Tyr Val Arg Asn Lys Ile Gly Glu Ile Val Thr Tyr His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225
```

<210> SEQ ID NO 9
<211> LENGTH: 229
<212> TYPE: PRT
<213> ORGANISM: Rhodococcus pyridinivorans MS-38

<400> SEQUENCE: 9

```
Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Gly His Thr Arg
```

145 150 155 160

Cys Pro Lys Tyr Val Arg Asn Lys Ile Gly Glu Ile Val Thr Tyr His
165 170 175

Gly Cys Gln Ile Tyr Pro Glu Ser Ser Ser Ala Gly Leu Gly Asp Asp
180 185 190

Pro Arg Pro Leu Tyr Thr Val Ala Phe Ser Ala Gln Glu Leu Trp Gly
195 200 205

Asp Asp Gly Asn Gly Lys Asp Val Val Cys Val Asp Leu Trp Glu Pro
210 215 220

Tyr Leu Ile Ser Ala
225

<210> SEQ ID NO 10
<211> LENGTH: 229
<212> TYPE: PRT
<213> ORGANISM: Nocardia sp. JBRs

<400> SEQUENCE: 10

Met Asp Gly Ile His Asp Thr Gly Gly Met Thr Gly Tyr Gly Pro Val
1 5 10 15

Pro Tyr Gln Lys Asp Glu Pro Phe Phe His Tyr Glu Trp Glu Gly Arg
20 25 30

Thr Leu Ser Ile Leu Thr Trp Met His Leu Lys Gly Ile Ser Trp Trp
35 40 45

Asp Lys Ser Arg Phe Phe Arg Glu Ser Met Gly Asn Glu Asn Tyr Val
50 55 60

Asn Glu Ile Arg Asn Ser Tyr Tyr Thr His Trp Leu Ser Ala Ala Glu
65 70 75 80

Arg Ile Leu Val Ala Asp Lys Ile Ile Thr Glu Glu Glu Arg Lys His
85 90 95

Arg Val Gln Glu Ile Leu Glu Gly Arg Tyr Thr Asp Arg Asn Pro Ser
100 105 110

Arg Lys Phe Asp Pro Ala Glu Ile Glu Lys Ala Ile Glu Arg Leu His
115 120 125

Glu Pro His Ser Leu Ala Leu Pro Gly Ala Glu Pro Ser Phe Ser Leu
130 135 140

Gly Asp Lys Val Lys Val Lys Asn Met Asn Pro Leu Gly His Thr Arg
145 150 155 160

Cys Pro Lys Tyr Val Arg Asn Lys Ile Gly Glu Ile Val Thr Ser His
165 170 175

Gly Cys Gln Ile Tyr Pro Glu Ser Ser Ser Ala Gly Leu Gly Asp Asp
180 185 190

Pro Arg Pro Leu Tyr Thr Val Ala Phe Ser Ala Gln Glu Leu Trp Gly
195 200 205

Asp Asp Gly Asn Gly Lys Asp Val Val Cys Val Asp Leu Trp Glu Pro
210 215 220

Tyr Leu Ile Ser Ala
225

<210> SEQ ID NO 11
<211> LENGTH: 229
<212> TYPE: PRT
<213> ORGANISM: Nocardia sp. YS-2002

<400> SEQUENCE: 11

Met Asp Gly Ile His Asp Thr Gly Gly Met Thr Gly Tyr Gly Pro Val

-continued

```
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Met Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Asn Pro Ser
            100                 105                 110

Arg Lys Phe Asp Pro Ala Glu Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Val Lys Val Lys Asn Met Asn Pro Leu Gly His Thr Arg
145                 150                 155                 160

Cys Pro Lys Tyr Val Arg Asn Lys Ile Gly Glu Ile Val Thr Ser His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225


<210> SEQ ID NO 12
<211> LENGTH: 229
<212> TYPE: PRT
<213> ORGANISM: Rhodococcus rhodochrous ATCC39384

<400> SEQUENCE: 12

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Met Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Asn Pro Ser
            100                 105                 110

Arg Lys Phe Asp Pro Ala Glu Ile Glu Lys Ala Ile Glu Arg Leu His
        115                 120                 125

Glu Pro His Ser Leu Val Leu Pro Gly Ala Glu Pro Ser Phe Ser Leu
    130                 135                 140
```

-continued

Gly Asp Lys Val Lys Val Lys Asn Met Asn Pro Leu Gly His Thr Arg
145 150 155 160

Cys Pro Lys Tyr Val Arg Asn Arg Ile Gly Glu Ile Val Thr Ser His
165 170 175

Gly Cys Gln Ile Tyr Pro Glu Ser Ser Ser Ala Gly Leu Gly Asp Asp
180 185 190

Pro Arg Pro Leu Tyr Thr Val Ala Phe Ser Ala Gln Glu Leu Trp Gly
195 200 205

Asp Asp Gly Asn Gly Lys Asp Val Val Cys Val Asp Leu Trp Glu Pro
210 215 220

Tyr Leu Ile Ser Ala
225

<210> SEQ ID NO 13
<211> LENGTH: 27
<212> TYPE: DNA
<213> ORGANISM: Artificial Sequence
<220> FEATURE:
<223> OTHER INFORMATION: B48C-F primer

<400> SEQUENCE: 13
tcgtggtgcg acaagtcgcg gttcttc 27

<210> SEQ ID NO 14
<211> LENGTH: 27
<212> TYPE: DNA
<213> ORGANISM: Artificial Sequence
<220> FEATURE:
<223> OTHER INFORMATION: B48C-R primer

<400> SEQUENCE: 14
cttgtcgcac cacgatatgc ccttgag 27

<210> SEQ ID NO 15
<211> LENGTH: 27
<212> TYPE: DNA
<213> ORGANISM: Artificial Sequence
<220> FEATURE:
<223> OTHER INFORMATION: B48D-F primer

<400> SEQUENCE: 15
tcgtgggacg acaagtcgcg gttcttc 27

<210> SEQ ID NO 16
<211> LENGTH: 27
<212> TYPE: DNA
<213> ORGANISM: Artificial Sequence
<220> FEATURE:
<223> OTHER INFORMATION: B48D-R primer

<400> SEQUENCE: 16
cttgtcgtcc cacgatatgc ccttgag 27

<210> SEQ ID NO 17
<211> LENGTH: 27
<212> TYPE: DNA
<213> ORGANISM: Artificial Sequence
<220> FEATURE:
<223> OTHER INFORMATION: B48E-F primer

<400> SEQUENCE: 17
tcgtgggagg acaagtcgcg gttcttc 27

<210> SEQ ID NO 18
<211> LENGTH: 27
<212> TYPE: DNA
<213> ORGANISM: Artificial Sequence
<220> FEATURE:
<223> OTHER INFORMATION: B48E-R primer

<400> SEQUENCE: 18
cttgtcctcc cacgatatgc ccttgag 27

<210> SEQ ID NO 19
<211> LENGTH: 27
<212> TYPE: DNA
<213> ORGANISM: Artificial Sequence
<220> FEATURE:
<223> OTHER INFORMATION: B48H-F primer

<400> SEQUENCE: 19
tcgtggcacg acaagtcgcg gttcttc 27

<210> SEQ ID NO 20
<211> LENGTH: 27
<212> TYPE: DNA
<213> ORGANISM: Artificial Sequence
<220> FEATURE:
<223> OTHER INFORMATION: B48H-R primer

<400> SEQUENCE: 20
cttgtcgtgc cacgatatgc ccttgag 27

<210> SEQ ID NO 21
<211> LENGTH: 27
<212> TYPE: DNA
<213> ORGANISM: Artificial Sequence
<220> FEATURE:
<223> OTHER INFORMATION: B48I-F primer

<400> SEQUENCE: 21
tcgtggatcg acaagtcgcg gttcttc 27

<210> SEQ ID NO 22
<211> LENGTH: 27
<212> TYPE: DNA
<213> ORGANISM: Artificial Sequence
<220> FEATURE:
<223> OTHER INFORMATION: B48I-R primer

<400> SEQUENCE: 22
cttgtcgatc cacgatatgc ccttgag 27

<210> SEQ ID NO 23
<211> LENGTH: 27
<212> TYPE: DNA
<213> ORGANISM: Artificial Sequence
<220> FEATURE:
<223> OTHER INFORMATION: B48K-F primer

<400> SEQUENCE: 23
tcgtggaagg acaagtcgcg gttcttc 27

<210> SEQ ID NO 24
<211> LENGTH: 27
<212> TYPE: DNA
<213> ORGANISM: Artificial Sequence
<220> FEATURE:
<223> OTHER INFORMATION: B48K-R primer

```
<400> SEQUENCE: 24

cttgtccttc cacgatatgc ccttgag                                    27


<210> SEQ ID NO 25
<211> LENGTH: 27
<212> TYPE: DNA
<213> ORGANISM: Artificial Sequence
<220> FEATURE:
<223> OTHER INFORMATION: B48M-F primer

<400> SEQUENCE: 25

tcgtggatgg acaagtcgcg gttcttc                                    27


<210> SEQ ID NO 26
<211> LENGTH: 27
<212> TYPE: DNA
<213> ORGANISM: Artificial Sequence
<220> FEATURE:
<223> OTHER INFORMATION: B48M-R primer

<400> SEQUENCE: 26

cttgtccatc cacgatatgc ccttgag                                    27


<210> SEQ ID NO 27
<211> LENGTH: 27
<212> TYPE: DNA
<213> ORGANISM: Artificial Sequence
<220> FEATURE:
<223> OTHER INFORMATION: B48N-F primer

<400> SEQUENCE: 27

tcgtggaacg acaagtcgcg gttcttc                                    27


<210> SEQ ID NO 28
<211> LENGTH: 27
<212> TYPE: DNA
<213> ORGANISM: Artificial Sequence
<220> FEATURE:
<223> OTHER INFORMATION: B48N-R primer

<400> SEQUENCE: 28

cttgtcgttc cacgatatgc ccttgag                                    27


<210> SEQ ID NO 29
<211> LENGTH: 27
<212> TYPE: DNA
<213> ORGANISM: Artificial Sequence
<220> FEATURE:
<223> OTHER INFORMATION: B48P-F primer

<400> SEQUENCE: 29

tcgtggccgg acaagtcgcg gttcttc                                    27


<210> SEQ ID NO 30
<211> LENGTH: 27
<212> TYPE: DNA
<213> ORGANISM: Artificial Sequence
<220> FEATURE:
<223> OTHER INFORMATION: B48P-R primer

<400> SEQUENCE: 30

cttgtccggc cacgatatgc ccttgag                                    27


<210> SEQ ID NO 31
<211> LENGTH: 27
```

<212> TYPE: DNA
<213> ORGANISM: Artificial Sequence
<220> FEATURE:
<223> OTHER INFORMATION: B48Q-F primer

<400> SEQUENCE: 31
tcgtggcagg acaagtcgcg gttcttc 27

<210> SEQ ID NO 32
<211> LENGTH: 27
<212> TYPE: DNA
<213> ORGANISM: Artificial Sequence
<220> FEATURE:
<223> OTHER INFORMATION: B48Q-R primer

<400> SEQUENCE: 32
cttgtcctgc cacgatatgc ccttgag 27

<210> SEQ ID NO 33
<211> LENGTH: 27
<212> TYPE: DNA
<213> ORGANISM: Artificial Sequence
<220> FEATURE:
<223> OTHER INFORMATION: B48S-F primer

<400> SEQUENCE: 33
tcgtggtccg acaagtcgcg gttcttc 27

<210> SEQ ID NO 34
<211> LENGTH: 27
<212> TYPE: DNA
<213> ORGANISM: Artificial Sequence
<220> FEATURE:
<223> OTHER INFORMATION: B48S-R primer

<400> SEQUENCE: 34
cttgtcggac cacgatatgc ccttgag 27

<210> SEQ ID NO 35
<211> LENGTH: 27
<212> TYPE: DNA
<213> ORGANISM: Artificial Sequence
<220> FEATURE:
<223> OTHER INFORMATION: B48T-F primer

<400> SEQUENCE: 35
tcgtggaccg acaagtcgcg gttcttc 27

<210> SEQ ID NO 36
<211> LENGTH: 27
<212> TYPE: DNA
<213> ORGANISM: Artificial Sequence
<220> FEATURE:
<223> OTHER INFORMATION: B48T-R primer

<400> SEQUENCE: 36
cttgtcggtc cacgatatgc ccttgag 27

<210> SEQ ID NO 37
<211> LENGTH: 229
<212> TYPE: PRT
<213> ORGANISM: Rhodococcus M8

<400> SEQUENCE: 37

Met Asp Gly Ile His Asp Thr Gly Gly Met Thr Gly Tyr Gly Pro Val
1 5 10 15

```
Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Met Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Asn Pro Ser
            100                 105                 110

Arg Lys Phe Asp Pro Ala Glu Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Val Lys Val Lys Asn Met Asn Pro Leu Gly His Thr Arg
145                 150                 155                 160

Cys Pro Lys Tyr Val Arg Asn Lys Ile Gly Glu Ile Val Thr Ser His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225


<210> SEQ ID NO 38
<211> LENGTH: 203
<212> TYPE: PRT
<213> ORGANISM: Rhodococcus M8

<400> SEQUENCE: 38

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
```

-continued 145 150 155 160

Arg Tyr Ile Val Ile Pro Glu Arg Pro Ala Gly Thr Asp Gly Trp Ser
165 170 175

Glu Asp Glu Leu Ala Lys Leu Val Ser Arg Asp Ser Met Ile Gly Val
180 185 190

Ser Asn Ala Leu Thr Pro Gln Glu Val Ile Val
195 200

<210> SEQ ID NO 39
<211> LENGTH: 104
<212> TYPE: PRT
<213> ORGANISM: Rhodococcus M8

<400> SEQUENCE: 39

Met Ser Glu Asp Thr Leu Thr Asp Arg Leu Pro Ala Thr Gly Thr Ala
1 5 10 15

Ala Pro Pro Arg Asp Asn Gly Glu Leu Val Phe Thr Glu Pro Trp Glu
20 25 30

Ala Thr Ala Phe Gly Val Ala Ile Ala Leu Ser Asp Gln Lys Ser Tyr
35 40 45

Glu Trp Glu Phe Phe Arg Gln Arg Leu Ile His Ser Ile Ala Glu Ala
50 55 60

Asn Gly Cys Glu Ala Tyr Tyr Glu Ser Trp Thr Lys Ala Leu Glu Ala
65 70 75 80

Ser Val Val Asp Ser Gly Leu Ile Ser Glu Asp Glu Ile Arg Glu Arg
85 90 95

Met Glu Ser Met Ala Ile Ile Asp
100

<210> SEQ ID NO 40
<211> LENGTH: 32
<212> TYPE: DNA
<213> ORGANISM: Artificial Sequence
<220> FEATURE:
<223> OTHER INFORMATION: M8-1 primer

<400> SEQUENCE: 40
ggtctagaat ggatggtatc cacgacacag gc 32

<210> SEQ ID NO 41
<211> LENGTH: 34
<212> TYPE: DNA
<213> ORGANISM: Artificial Sequence
<220> FEATURE:
<223> OTHER INFORMATION: M8-2 primer

<400> SEQUENCE: 41
cccctgcagg tcagtcgatg atggccatcg attc 34

<210> SEQ ID NO 42
<211> LENGTH: 195
<212> TYPE: PRT
<213> ORGANISM: Unknown
<220> FEATURE:
<223> OTHER INFORMATION: uncultured bacterium SP1

<400> SEQUENCE: 42

Met Asp Gly Ile His Asp Thr Gly Gly Met Thr Gly Tyr Gly Pro Val
1 5 10 15

Pro Tyr Gln Lys Asp Glu Pro Phe Phe His Tyr Glu Trp Glu Gly Arg
20 25 30

```
Thr Leu Ser Ile Leu Thr Trp Met His Leu Lys Gly Ile Ser Trp Trp
        35                  40                  45

Asp Lys Pro Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ser Ala Gly Leu Gly Asp Asp
            180                 185                 190

Pro Arg Pro
        195


<210> SEQ ID NO 43
<211> LENGTH: 166
<212> TYPE: PRT
<213> ORGANISM: Unknown
<220> FEATURE:
<223> OTHER INFORMATION: uncultured bacterium BD2

<400> SEQUENCE: 43

Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
    50                  55                  60

Asp Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Asn Gln Ser Glu Glu Tyr Glu Pro Ala Gly Thr His Thr
145                 150                 155                 160

Val Pro Glu Ile Cys Ala
                165


<210> SEQ ID NO 44
```

```
<211> LENGTH: 218
<212> TYPE: PRT
<213> ORGANISM: Comamonas testosteroni

<400> SEQUENCE: 44

Met Asn Gly Ile His Asp Thr Gly Gly Ala His Gly Tyr Gly Pro Val
1               5                   10                  15

Tyr Arg Glu Pro Asn Glu Pro Val Phe Arg Tyr Asp Trp Glu Lys Thr
            20                  25                  30

Val Met Ser Leu Phe Pro Ala Leu Phe Ala Asn Gly Asn Phe Asn Leu
        35                  40                  45

Asp Glu Phe Arg His Gly Ile Glu Arg Met Asn Pro Ile Asp Tyr Leu
    50                  55                  60

Lys Gly Thr Tyr Tyr Glu His Trp Ile His Ser Ile Glu Thr Leu Leu
65                  70                  75                  80

Val Glu Lys Gly Val Leu Thr Ala Thr Glu Leu Ala Thr Gly Lys Ala
                85                  90                  95

Ser Gly Lys Thr Ala Thr Pro Val Leu Thr Pro Ala Ile Val Asp Gly
            100                 105                 110

Leu Leu Ser Thr Gly Ala Ser Ala Ala Arg Glu Glu Gly Ala Arg Ala
        115                 120                 125

Arg Phe Ala Val Gly Asp Lys Val Arg Val Leu Asn Lys Asn Pro Val
    130                 135                 140

Gly His Thr Arg Met Pro Arg Tyr Thr Arg Gly Lys Val Gly Thr Val
145                 150                 155                 160

Val Ile Asp His Gly Val Phe Val Thr Pro Asp Thr Ala Ala His Gly
                165                 170                 175

Lys Gly Glu His Pro Gln His Val Tyr Thr Val Ser Phe Thr Ser Val
            180                 185                 190

Glu Leu Trp Gly Gln Asp Ala Ser Ser Pro Lys Asp Thr Ile Arg Val
        195                 200                 205

Asp Leu Trp Asp Asp Tyr Leu Glu Pro Ala
    210                 215


<210> SEQ ID NO 45
<211> LENGTH: 226
<212> TYPE: PRT
<213> ORGANISM: Geobacillus thermoglucosidasius Q6

<400> SEQUENCE: 45

Met Asn Gly Pro His Asp Leu Gly Gly Lys Arg Asp Phe Gly Pro Ile
1               5                   10                  15

Ile Lys His Asp Gln Glu Pro Leu Phe His Glu Glu Trp Glu Ala Lys
            20                  25                  30

Val Leu Ala Met His Phe Ala Leu Leu Gly Gln Gly Val Ile Asn Trp
        35                  40                  45

Asp Glu Phe Arg His Gly Ile Glu Arg Met Gly Tyr Val Tyr Tyr Leu
    50                  55                  60

Thr Ser Ser Tyr Tyr Glu His Trp Leu Ala Ser Leu Glu Thr Val Leu
65                  70                  75                  80

Ala Glu Lys Asn Ile Ile Asn Ser Glu Gln Tyr Arg Lys Arg Ile Arg
                85                  90                  95

Glu Ile Glu Tyr Gly Met Ser Val Pro Val Ser Glu Lys Pro Glu Leu
            100                 105                 110

Lys Glu Ser Leu Leu Ser Glu Val Ile Tyr Gly Thr Lys Ile Ser Ser
        115                 120                 125
```

-continued

```
Glu Arg Arg Glu Ser Thr Val Ser Pro Arg Phe Arg Pro Gly Asp Arg
    130                 135                 140

Val Arg Val Lys His Phe Tyr Thr Asn Lys His Thr Arg Cys Pro Gln
145                 150                 155                 160

Tyr Val Met Gly Lys Val Gly Val Val Glu Leu Leu His Gly Asn His
                165                 170                 175

Val Phe Pro Asp Ser Asn Ala His Gly Asp Gly Glu Ala Pro Gln Pro
            180                 185                 190

Leu Tyr Asn Val Arg Phe Glu Ala Arg Glu Leu Trp Gly Gly Glu Ala
        195                 200                 205

His Glu Lys Asp Ser Leu Asn Leu Asp Leu Trp Asp Ser Tyr Leu Thr
    210                 215                 220

His Ala
225
```

<210> SEQ ID NO 46
<211> LENGTH: 230
<212> TYPE: PRT
<213> ORGANISM: Pseudonocardia thermophila JCM3095

<400> SEQUENCE: 46

```
Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala
225                 230
```

<210> SEQ ID NO 47
<211> LENGTH: 226
<212> TYPE: PRT

<213> ORGANISM: Rhodococcus rhodochrous Cr4

<400> SEQUENCE: 47

```
Met Asp Gly Ile His Asp Leu Gly Gly Arg Ala Gly Leu Gly Pro Val
1               5                   10                  15

Asn Pro Glu Pro Gly Glu Pro Val Phe His Ser Arg Trp Glu Arg Ser
            20                  25                  30

Val Leu Thr Met Phe Pro Ala Met Ala Leu Ala Gly Ala Phe Asn Leu
        35                  40                  45

Asp Gln Phe Arg Gly Ala Met Glu Gln Ile Pro Pro His Asp Tyr Leu
    50                  55                  60

Thr Ser Gln Tyr Tyr Glu His Trp Met His Ala Met Ile His Tyr Gly
65                  70                  75                  80

Ile Glu Ala Gly Ile Phe Asp Pro Asn Glu Leu Asp Arg Arg Thr Gln
                85                  90                  95

Tyr Tyr Leu Glu His Pro Asp Glu Asp Pro Pro Leu Arg Gln Asp Pro
            100                 105                 110

Gln Leu Val Glu Thr Ile Ser Gln Leu Ile Met His Gly Ala Asp Tyr
        115                 120                 125

Arg Arg Pro Thr Asp Ala Glu Gly Val Phe Ala Val Gly Asp Lys Val
    130                 135                 140

Val Val Arg Ser Asp Ala Ser Pro Asn Thr His Thr Arg Arg Ala Gly
145                 150                 155                 160

Tyr Ile Arg Gly Arg Thr Gly Glu Ile Val Ala Ala His Gly Ala Tyr
                165                 170                 175

Val Phe Pro Asp Thr Asn Ala Val Gly Ala Gly Glu His Pro Glu His
            180                 185                 190

Leu Tyr Thr Val Arg Phe Ser Ala Thr Glu Leu Trp Gly Glu Thr Ala
        195                 200                 205

Thr Ser Asn Ala Val Asn His Ile Asp Val Phe Glu Pro Tyr Leu Leu
    210                 215                 220

Pro Ala
225
```

<210> SEQ ID NO 48
<211> LENGTH: 6
<212> TYPE: PRT
<213> ORGANISM: Rhodococcus N-771

<400> SEQUENCE: 48

```
Cys Ser Leu Cys Ser Cys
1               5
```

<210> SEQ ID NO 49
<211> LENGTH: 6
<212> TYPE: PRT
<213> ORGANISM: Rhodococcus rhodochrous J1

<400> SEQUENCE: 49

```
Cys Thr Leu Cys Ser Cys
1               5
```

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide
<220> FEATURE:

<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is Cys, Asp, Glu, His, Ile, Lys, Met, Asn, Pro, Gln, Ser or Thr
<220> FEATURE:
<221> NAME/KEY: misc_feature
<222> LOCATION: (7)..(8)
<223> OTHER INFORMATION: Xaa can be any naturally occurring amino acid

<400> SEQUENCE: 50

```
Gly Xaa Xaa Xaa Xaa Asp Xaa Xaa Arg
1               5
```

<210> SEQ ID NO 51
<211> LENGTH: 229
<212> TYPE: PRT
<213> ORGANISM: Rhodococcus rhodochrous J1
<220> FEATURE:
<221> NAME/KEY: misc_feature
<222> LOCATION: (45)..(48)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid

<400> SEQUENCE: 51

```
Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Xaa Xaa Xaa Xaa
        35                  40                  45

Asp Xaa Xaa Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225
```

<210> SEQ ID NO 52
<211> LENGTH: 229
<212> TYPE: PRT
<213> ORGANISM: Rhodococcus ruber RH

<400> SEQUENCE: 52

```
Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Met Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Asn Pro Ser
            100                 105                 110

Arg Lys Phe Asp Pro Ala Glu Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Val Lys Val Lys Asn Met Asn Pro Leu Gly His Thr Arg
145                 150                 155                 160

Cys Pro Lys Tyr Val Arg Ser Lys Ile Gly Glu Ile Val Thr Ser His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Ala Asp Leu Trp Glu Pro
    210                 215                 220

Tyr Leu Ile Ser Ala
225
```

<210> SEQ ID NO 53
<211> LENGTH: 690
<212> TYPE: DNA
<213> ORGANISM: Rhodococcus rhodochrous J1D

<400> SEQUENCE: 53

```
atggatggta tccacgacac aggcggcatg accggatacg gaccggtccc ctatcagaag      60

gacgagccct tcttccacta cgagtgggag ggtcggaccc tgtcaattct gacttggatg     120

catctcaagg gcatatcgtg gtgggacaag tcgcggttct tccgggagtc gatggggaac     180

gaaaactacg tcaacgagat tcgcaactcg tactacaccc actggctgag tgcggcagaa     240

cgtatcctcg tcgccgacaa gatcatcacc gaagaagagc gaaagcaccg tgtgcaagag     300

atccttgagg gtcggtacac ggacaggaag ccgtcgcgga agttcgatcc ggcccagatc     360

gagaaggcga tcgaacggct tcacgagccc cactccctag cgcttccagg agcggagccg     420

agtttctctc tcggtgacaa gatcaaagtg aagagtatga acccgctggg acacacacgg     480

tgcccgaaat atgtgcggag caagatcggg gaaatcgtcg cctaccacgg ctgccagatc     540
```

```
tatcccgaga gcagctccgc cggcctcggc gacgatcctc gcccgctcta cacggtcgcg    600

ttttccgccc aggaactgtg gggcgacgac ggaaacggga aagacgtagt gtgcgccgat    660

ctctgggaac cgtacctgat ctctgcgtga                                     690


<210> SEQ ID NO 54
<211> LENGTH: 690
<212> TYPE: DNA
<213> ORGANISM: Rhodococcus rhodochrous 204

<400> SEQUENCE: 54

atggatggta tccacgacac aggcggcatg accggatacg gaccggtccc ctatcagaag     60

gacgagccct tcttccacta cgagtgggag ggtcggaccc tgtcaattct gacttggatg    120

catctcaagg gcatatcgtg gtgggacaag tcgcggttct tccgggagaa gatggggaac    180

gaaaactacg tcaacgagat tcgcaactcg tactacaccc actggctgag tgcggcagaa    240

cgtatcctcg tcgccgacaa gatcatcacc gaagaagagc gaaagcaccg tgtgcaagag    300

atccttgagg gtcggtacac ggacaggaag ccgtcgcgga agttcgatcc ggcccagatc    360

gagaaggcga tcgaacggct tcacgagccc cactccctag cgcttccagg agcggagccg    420

agtttctctc tcggtgacaa gatcaaagtg aagagtatga acccgctggg acacacacgg    480

tgcccgaaat atgtgcggag caagatcggg gaaatcgtcg cctaccacgg ctgccagatc    540

tatcccgaga gcagctccgc cggcctcggc gacgatcctc gcccgctcta cacggtcgcg    600

ttttccgccc aggaactgtg gggcgacgac ggaaacggga aagacgtagt gtgcgccgat    660

ctctgggaac cgtacctgat ctctgcgtga                                     690


<210> SEQ ID NO 55
<211> LENGTH: 690
<212> TYPE: DNA
<213> ORGANISM: Rhodococcus rhodochrous 414

<400> SEQUENCE: 55

atggatggta tccacgacac aggcggcatg accggatacg gaccggtccc ctatcagaag     60

gacgagccct tcttccacta cgagtgggag ggtcggaccc tgtcaattct gacttggatg    120

catctcaagg gcatatcgtg gtgggacaag tcgcggttct tccgggagaa gatggggaac    180

gaaaactacg tcaacgagat tcgcaactcg tactacaccc actggctgag tgcggcagaa    240

cgtatcctcg tcgccgacaa gatcatcacc gaagaagagc gaaagcaccg tgtgcaagag    300

atccttgagg gtcggtacac ggacaggaag ccgtcgcgga agttcgatcc ggcccagatc    360

gagaaggcga tcgaacggct tcacgagccc cactccctag cgcttccagg agcggagccg    420

agtttctctc tcggtgacaa gatcaaagtg aagagtatga acccgctggg acacacacgg    480

tgcccgaaat atgtgcggag ccggatcggg gaaatcgtcg cctaccacgg ctgccagatc    540

tatcccgaga gcagctccgc cggcctcggc gacgatcctc gcccgctcta cacggtcgcg    600

ttttccgccc aggaactgtg gggcgacgac ggaaacggga aagacgtagt gtgcgccgat    660

ctctgggaac cgtacctgat ctctgcgtga                                     690


<210> SEQ ID NO 56
<211> LENGTH: 690
<212> TYPE: DNA
<213> ORGANISM: Rhodococcus rhodochrous 855

<400> SEQUENCE: 56

atggatggta tccacgacac aggcggcatg accggatacg gaccggtccc ctatcagaag     60
```

gacgagccct tcttccacta cgagtgggag ggtcggaccc tgtcaattct gacttggatg 120
catctcaagg gcatatcgtg gtgggacaag tcgcggttct tccgggagaa gatggggaac 180
gaaaactacg tcaacgagat tcgcaactcg tactacaccc actggctgag tgcggcagaa 240
cgtatcctcg tcgccgacaa gatcatcacc gaagaagagc gaaagcaccg tgtgcaagag 300
atccttgagg gtcggtacaa ggacaggaag ccgtcgcggt acttcgatcc ggcccagatc 360
gagaaggcga tcgaacggct tcacgagccc cactccctag cgcttccagg agcggagccg 420
agtttctctc tcggtgacaa gatcaaagtg aagagtatga acccgctggg acacacacgg 480
tgcccgaaat atgtgcggag caagatcggg gaaatcgtcg cctaccacgg ctgccagatc 540
tatcccgaga gcagctccgc cggcctcggc gacgatcctc gcccgctcta cacggtcgcg 600
ttttccgccc aggaactgtg ggcgacgac ggaaacggga aagacgtagt gtgcgccgat 660
ctctgggaac cgtacctgat ctctgcgtga 690

<210> SEQ ID NO 57
<211> LENGTH: 612
<212> TYPE: DNA
<213> ORGANISM: Rhodococcus rhodochrous D2

<400> SEQUENCE: 57
gtgagcgagc acgtcaataa gtacacggag tacgaggcac gtaccaaggc gatcgaaacc 60
ttgctgtacg agcgagggct catcacgccc gccgcggtcg accgagtcgt ttcgtactac 120
gaggacgaga tcggcccgat gggcggtgcc aaggtcgtgg ccaagtcctg ggtggaccct 180
gagtaccgca agtggctcga agaggacgcg acggccgcga tggcgtcatt gggctatgcc 240
ggtgagcagg cacaccaaat ttcggcggtc ttcaacgact cccaaacgca tcacgtggtg 300
gtgtgcactc tgtgttcgtg ctatccgtgg ccggtgcttg gtctcccgcc cgcctggtac 360
aagagcatgg ggtaccggtc ccgagtggta gcggaccctc gtggagtgct caagcgcgat 420
ttcggtttcg acatccccga tgaggtggag gtcagggttt gggacagcag ctccgaaatc 480
cgctacatcg tcatcccgga acggccggcc ggcaccgacg gttggtccga ggaggagctg 540
acgaagctgg tgagccggga ctcgatgatc ggtgtcagta atgcgctcac accgcaggaa 600
gtgatcgtat ga 612

<210> SEQ ID NO 58
<211> LENGTH: 690
<212> TYPE: DNA
<213> ORGANISM: Rhodococcus rhodochrous 005

<400> SEQUENCE: 58
atggatggta tccacgacac aggcggcatg accggatacg gaccggtcgg gtatcagaag 60
gacgagccct tcttccacta cgagtgggag ggtcggaccc tgtcaattct gacttggatg 120
catctcaagg gcatatcgtg gtgggacaag tcgcggttct tccgggagat gatggggaac 180
gaaaactacg tcaacgagat tcgcaactcg tactacaccc actggctgag tgcggcagaa 240
cgtatcctcg tcgccgacaa gatcatcacc gaagaagagc gaaagcaccg tgtgcaagag 300
atccttgagg gtcggtacaa ggacaggaag ccgtcgcggt acttcgatcc ggcccagatc 360
gagaaggcga tcgaacggct tcacgagccc cactccctag cgcttccagg agcggagccg 420
agtttctctc tcggtgacaa gatcaaagtg aagagtatga acccgctggg acacacacgg 480
tgcccgaaat atgtgcggag caagatcggg gaaatcgtcg cctaccacgg ctgccagatc 540
tatcccgaga gcagctccgc cggcctcggc gacgatcctc gcccgctcta cacggtcgcg 600
ttttccgccc aggaactgtg gggcgacgac ggaaacggga aagacgtagt gtgcgccgat 660
ctctgggaac cgtacctgat ctctgcgtga 690

<210> SEQ ID NO 59
<211> LENGTH: 690
<212> TYPE: DNA
<213> ORGANISM: Rhodococcus rhodochrous 108A

<400> SEQUENCE: 59
atggatggta tccacgacac aggcggcatg accggatacg gaccggtcgg gtatcagaag 60
gacgagccct tcttccacta cgagtgggag ggtcggaccc tgtcaattct gacttggatg 120
catctcaagg gcatatcgtg gtgggacaag tcgcggttct tccgggagat gatggggaac 180
gaaaactacg tcaacgagat tcgcaactcg tactacaccc actggctgag tgcggcagaa 240
cgtatcctcg tcgccgacaa gatcatcacc gaagaagagc gaaagcaccg tgtgcaagag 300
atccttgagg gtcggtacaa ggacaggaag ccgtcgcggt acttcgatcc ggcccagatc 360
gagaaggcga tcgaacggct tcacgagccc cactccctag cgcttccagg agcggagccg 420
agtttctcta gcggtgacaa gatcaaagtg aagagtatga acccgctggg acacacacgg 480
tgcccgaaat atgtgcggag caagatcggg gaaatcgtcg cctaccacgg ctgccagatc 540
tatcccgaga gcagctccgc cggcctcggc gacgatcctc gcccgctcta cacggtcgcg 600
ttttccgccc aggaactgtg gggcgacgac ggaaacggga aagacgtagt gtgcgccgat 660
ctctgggaac cgtacctgat ctctgcgtga 690

<210> SEQ ID NO 60
<211> LENGTH: 690
<212> TYPE: DNA
<213> ORGANISM: Rhodococcus rhodochrous 211

<400> SEQUENCE: 60
atggatggta tccacgacac aggcggcatg accggatacg gaccggtcgg gtatcagaag 60
gacgagccct tcttccacta cgagtgggag ggtcggaccc tgtcaattct gacttggatg 120
catctcaagg gcatatcgtg gtgggacaag tcgcggttct tccgggagat gatggggaac 180
gaaaactacg tcaacgagat tcgcaactcg tactacaccc actggctgag tgcggcagaa 240
cgtatcctcg tcgccgacaa gatcatcacc gaagaagagc gaaagcaccg tgtgcaagag 300
atccttgagg gtcggtacaa ggacaggaag ccgtcgcggt acttcgatcc ggcccagatc 360
gagaaggcga tcgaacggct tcacgagccc cactccctag cgcttccagg agcggagccg 420
agtttctcta gcggtgacaa gatcaaagtg aagagtatga acccgctggg acacacacgg 480
tgcccgaaat atgtgcggag caagatcggg gaaatcgtcg cctaccacgg ctgccagatc 540
tatcccgaga gcagctccgc cggcctcggc gacgatcctc gcccgctcta cacggtcgcg 600
ttttccgccc aggaactgtg gggcgacgac ggaaacggga aagacgtagt gcacgccgat 660
ctctgggaac cgtacctgat ctctgcgtga 690

<210> SEQ ID NO 61
<211> LENGTH: 690
<212> TYPE: DNA
<213> ORGANISM: Rhodococcus rhodochrous 306A

<400> SEQUENCE: 61
atggatggta tccacgacac aggcggcatg accggatacg gaccggtcgg gtatcagaag 60

```
gacgagccct tcttccacta cgagtgggag ggtcggaccc tgtcaattct gacttggatg    120
catctcaagg gcatatcgtg gtgggacaag tcgcggttct tccgggagat gatggggaac    180
gaaaactacg tcaacgagat tcgcaactcg tactacaccc actggctgag tgcggcagaa    240
cgtatcctcg tcgccgacaa gatcatcacc gaagaagagc gaaagcaccg tgtgcaagag    300
atccttgagg gtcggtacaa ggacaggaag ccgtcgcggt acttcgatcc ggcccagatc    360
gagaaggcga tcgaacggct tcacgagccc cactccctag cgcttccagg agcggagccg    420
agtttctctc tcggtgacaa gatcaaagtg aagagtatga acccgctggg acacacacgg    480
tgcccgaaat atgtgcggag caagatcggg gaaatcgtcg cctaccacgg ctgccagatc    540
tatcccgaga gcagctccgc cggcctcggc gacgatcctc gcccgctcta cacggtcgcg    600
ttttccgccc aggaactgtg ggcgacgac ggaaacggga aagacgtagt gcacgccgat    660
ctctgggaac cgtacctgat ctctgcgtga                                     690
```

<210> SEQ ID NO 62
<211> LENGTH: 1644
<212> TYPE: DNA
<213> ORGANISM: Rhodococcus rhodochrous M8

<400> SEQUENCE: 62

```
ggtctagaat ggatggtatc cacgacacag gcggcatgac cggatacgga ccggtcccct     60
atcagaagga cgagcccttc ttccactacg agtgggaggg tcggaccctg tcgattctga    120
cctggatgca tctcaagggc atgtcgtggt gggacaagtc gcggttcttc cgggagtcga    180
tggggaacga aaactacgtc aacgagattc gcaactcgta ctacacccac tggctgagtg    240
cggcagaacg tatcctcgtc gccgacaaga tcatcaccga agaagagcga aagcaccgtg    300
tgcaggagat cctcgagggt cggtacacgg acaggaaccc gtcgcggaag ttcgatccgg    360
ccgagatcga gaaggcgatc gaacggcttc acgagcccca ctccctagca cttccaggag    420
cggagccgag tttctccctc ggtgacaagg tcaaagtgaa gaatatgaac ccgctgggac    480
acacacggtg cccgaaatat gtgcggaaca agatcgggga aatcgtcacc tcccacggct    540
gccagatcta tcccgagagc agctccgccg gcctcggcga cgatccccgc ccgctctaca    600
cggtcgcgtt ttccgcccag gaactgtggg gcgacgacgg aaacgggaaa gacgtagtgt    660
gcgtcgatct ctgggaaccg tacctgatct ctgcgtgaaa ggaatacgat agtgagcgag    720
cacgtcaata agtacacgga gtacgaggca cgtaccaagg caatcgaaac tttgctgtac    780
gagcgagggc tcatcacgcc cgccgcggtc gaccgagtcg tttcgtacta cgagaacgag    840
atcggcccga tgggcggtgc caaggtcgtg gcgaagtcct gggtggaccc tgagtaccgc    900
aagtggctcg aagaggacgc gacggccgcg atggcgtcat tgggctatgc cggtgagcag    960
gcacaccaaa tttcggcggt cttcaacgac tcccaaacgc atcacgtggt ggtgtgcact   1020
ctgtgttcgt gctatccgtg gccggtgctt ggtctcccgc ccgcctggta caagagcatg   1080
gagtaccggt cccgagtggt agcagaccct cgtggagtgc tcaagcgcga tttcggtttc   1140
gacatccccg atgaggtgga ggtcagggtt tgggacagca gctccgaaat ccgctacatc   1200
gtcatcccgg aacggccggc cggcaccgac ggttggtccg aggacgagct ggcgaagctg   1260
gtgagtcggg actcgatgat cggtgtcagt aatgcgctca caccccagga agtgatcgta   1320
tgagtgaaga cacactcact gatcggctcc cggcgactgg gaccgccgca ccgccccgcg   1380
acaatggcga gcttgtattc accgagcctt gggaagcaac ggcattcggg gtcgccatcg   1440
```

-continued

```
cgctttcgga tcagaagtcg tacgaatggg agttcttccg acagcgtctc attcactcca   1500

tcgctgaggc caacggttgc gaggcatact acgagagctg gacaaaggcg ctcgaggcca   1560

gcgtggtcga ctcggggctg atcagcgaag atgagatccg cgagcgcatg gaatcgatgg   1620

ccatcatcga ctgacctgca gggg                                          1644


<210> SEQ ID NO 63
<211> LENGTH: 33
<212> TYPE: DNA
<213> ORGANISM: Artificial Sequence
<220> FEATURE:
<223> OTHER INFORMATION: B17RM-F primer
<220> FEATURE:
<221> NAME/KEY: misc_feature
<222> LOCATION: (16)..(17)
<223> OTHER INFORMATION: n is a, c, g, or t

<400> SEQUENCE: 63

ggatacggac cggtcnnsta tcagaaggac gag                                  33


<210> SEQ ID NO 64
<211> LENGTH: 33
<212> TYPE: DNA
<213> ORGANISM: Artificial Sequence
<220> FEATURE:
<223> OTHER INFORMATION: B17RM-R primer
<220> FEATURE:
<221> NAME/KEY: misc_feature
<222> LOCATION: (17)..(18)
<223> OTHER INFORMATION: n is a, c, g, or t

<400> SEQUENCE: 64

ctcgtccttc tgatasnnga ccggtccgta tcc                                  33


<210> SEQ ID NO 65
<211> LENGTH: 29
<212> TYPE: DNA
<213> ORGANISM: Artificial Sequence
<220> FEATURE:
<223> OTHER INFORMATION: NH19 primer

<400> SEQUENCE: 65

gcctctagat atcgccattc cgttgccgg                                       29


<210> SEQ ID NO 66
<211> LENGTH: 31
<212> TYPE: DNA
<213> ORGANISM: Artificial Sequence
<220> FEATURE:
<223> OTHER INFORMATION: NH20 primer

<400> SEQUENCE: 66

accctgcagg ctcggcgcac cggatgccca c                                    31


<210> SEQ ID NO 67
<211> LENGTH: 28
<212> TYPE: DNA
<213> ORGANISM: Artificial Sequence
<220> FEATURE:
<223> OTHER INFORMATION: B37A-F primer

<400> SEQUENCE: 67

gtcaattgcg acttggatgc atctcaag                                        28


<210> SEQ ID NO 68
<211> LENGTH: 27
```

<212> TYPE: DNA
<213> ORGANISM: Artificial Sequence
<220> FEATURE:
<223> OTHER INFORMATION: B37A-R primer

<400> SEQUENCE: 68
ccaagtcgca attgacaggg tccgacc 27

<210> SEQ ID NO 69
<211> LENGTH: 28
<212> TYPE: DNA
<213> ORGANISM: Artificial Sequence
<220> FEATURE:
<223> OTHER INFORMATION: B37D-F primer

<400> SEQUENCE: 69
gtcaattgac acttggatgc atctcaag 28

<210> SEQ ID NO 70
<211> LENGTH: 27
<212> TYPE: DNA
<213> ORGANISM: Artificial Sequence
<220> FEATURE:
<223> OTHER INFORMATION: B37D-R primer

<400> SEQUENCE: 70
ccaagtgtca attgacaggg tccgacc 27

<210> SEQ ID NO 71
<211> LENGTH: 28
<212> TYPE: DNA
<213> ORGANISM: Artificial Sequence
<220> FEATURE:
<223> OTHER INFORMATION: B37F-F primer

<400> SEQUENCE: 71
gtcaattttc acttggatgc atctcaag 28

<210> SEQ ID NO 72
<211> LENGTH: 27
<212> TYPE: DNA
<213> ORGANISM: Artificial Sequence
<220> FEATURE:
<223> OTHER INFORMATION: B37F-R primer

<400> SEQUENCE: 72
ccaagtgaaa attgacaggg tccgacc 27

<210> SEQ ID NO 73
<211> LENGTH: 28
<212> TYPE: DNA
<213> ORGANISM: Artificial Sequence
<220> FEATURE:
<223> OTHER INFORMATION: B37I-F primer

<400> SEQUENCE: 73
gtcaattatc acttggatgc atctcaag 28

<210> SEQ ID NO 74
<211> LENGTH: 27
<212> TYPE: DNA
<213> ORGANISM: Artificial Sequence
<220> FEATURE:
<223> OTHER INFORMATION: B37I-R primer

<400> SEQUENCE: 74

-continued ccaagtgata attgacaggg tccgacc 27

<210> SEQ ID NO 75
<211> LENGTH: 28
<212> TYPE: DNA
<213> ORGANISM: Artificial Sequence
<220> FEATURE:
<223> OTHER INFORMATION: B37M-F primer

<400> SEQUENCE: 75
gtcaattatg acttggatgc atctcaag 28

<210> SEQ ID NO 76
<211> LENGTH: 27
<212> TYPE: DNA
<213> ORGANISM: Artificial Sequence
<220> FEATURE:
<223> OTHER INFORMATION: B37M-R primer

<400> SEQUENCE: 76
ccaagtcata attgacaggg tccgacc 27

<210> SEQ ID NO 77
<211> LENGTH: 28
<212> TYPE: DNA
<213> ORGANISM: Artificial Sequence
<220> FEATURE:
<223> OTHER INFORMATION: B37T-F primer

<400> SEQUENCE: 77
gtcaattacc acttggatgc atctcaag 28

<210> SEQ ID NO 78
<211> LENGTH: 27
<212> TYPE: DNA
<213> ORGANISM: Artificial Sequence
<220> FEATURE:
<223> OTHER INFORMATION: B37T-R primer

<400> SEQUENCE: 78
ccaagtggta attgacaggg tccgacc 27

<210> SEQ ID NO 79
<211> LENGTH: 28
<212> TYPE: DNA
<213> ORGANISM: Artificial Sequence
<220> FEATURE:
<223> OTHER INFORMATION: B37V-F primer

<400> SEQUENCE: 79
gtcaattgtc acttggatgc atctcaag 28

<210> SEQ ID NO 80
<211> LENGTH: 27
<212> TYPE: DNA
<213> ORGANISM: Artificial Sequence
<220> FEATURE:
<223> OTHER INFORMATION: B37V-R primer

<400> SEQUENCE: 80
ccaagtgaca attgacaggg tccgacc 27

<210> SEQ ID NO 81
<211> LENGTH: 21
<212> TYPE: PRT
<213> ORGANISM: Artificial Sequence
<220> FEATURE:
<223> OTHER INFORMATION: Specific amino acid residue
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa is Ala, Val, Asp, Thr, Phe, Ile or Met
<220> FEATURE:
<221> NAME/KEY: misc_feature
<222> LOCATION: (10)..(20)
<223> OTHER INFORMATION: Xaa can be any naturally occurring amino acid

<400> SEQUENCE: 81

```
Trp Glu Xaa Xaa Xaa Xaa Xaa Xaa Xaa Xaa Xaa Xaa Xaa Xaa Xaa Xaa
1               5                   10                  15

Xaa Xaa Xaa Xaa Asp
            20
```

<210> SEQ ID NO 82
<211> LENGTH: 229
<212> TYPE: PRT
<213> ORGANISM: Rhodococcus rhodochrous J1
<220> FEATURE:
<221> NAME/KEY: misc_feature
<222> LOCATION: (31)..(36)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa is Ala, Val, Asp, Thr, Phe, Ile or Met
<220> FEATURE:
<221> NAME/KEY: misc_feature
<222> LOCATION: (38)..(48)
<223> OTHER INFORMATION: Xaa can be any naturally occurring amino acid

<400> SEQUENCE: 82

```
Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ser Ala Gly Leu Gly Asp Asp
            180                 185                 190
```

-continued

```
Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225
```

<210> SEQ ID NO 83
<211> LENGTH: 27
<212> TYPE: DNA
<213> ORGANISM: Artificial Sequence
<220> FEATURE:
<223> OTHER INFORMATION: A83A-F primer

<400> SEQUENCE: 83
ggtgaggcgg cacaccaaat ttcggcg 27

<210> SEQ ID NO 84
<211> LENGTH: 25
<212> TYPE: DNA
<213> ORGANISM: Artificial Sequence
<220> FEATURE:
<223> OTHER INFORMATION: A83A-R primer

<400> SEQUENCE: 84
gtgtgccgcc tcaccggcat agccc 25

<210> SEQ ID NO 85
<211> LENGTH: 27
<212> TYPE: DNA
<213> ORGANISM: Artificial Sequence
<220> FEATURE:
<223> OTHER INFORMATION: A83C-F primer

<400> SEQUENCE: 85
ggtgagtgcg cacaccaaat ttcggcg 27

<210> SEQ ID NO 86
<211> LENGTH: 25
<212> TYPE: DNA
<213> ORGANISM: Artificial Sequence
<220> FEATURE:
<223> OTHER INFORMATION: A83C-R primer

<400> SEQUENCE: 86
gtgtgcgcac tcaccggcat agccc 25

<210> SEQ ID NO 87
<211> LENGTH: 27
<212> TYPE: DNA
<213> ORGANISM: Artificial Sequence
<220> FEATURE:
<223> OTHER INFORMATION: A83D-F primer

<400> SEQUENCE: 87
ggtgaggacg cacaccaaat ttcggcg 27

<210> SEQ ID NO 88
<211> LENGTH: 25
<212> TYPE: DNA
<213> ORGANISM: Artificial Sequence
<220> FEATURE:
<223> OTHER INFORMATION: A83D-R primer

<400> SEQUENCE: 88
gtgtgcgtcc tcaccggcat agccc 25

<210> SEQ ID NO 89
<211> LENGTH: 27
<212> TYPE: DNA
<213> ORGANISM: Artificial Sequence
<220> FEATURE:
<223> OTHER INFORMATION: A83E-F primer

<400> SEQUENCE: 89
ggtgaggagg cacaccaaat ttcggcg 27

<210> SEQ ID NO 90
<211> LENGTH: 25
<212> TYPE: DNA
<213> ORGANISM: Artificial Sequence
<220> FEATURE:
<223> OTHER INFORMATION: A83E-R primer

<400> SEQUENCE: 90
gtgtgcctcc tcaccggcat agccc 25

<210> SEQ ID NO 91
<211> LENGTH: 27
<212> TYPE: DNA
<213> ORGANISM: Artificial Sequence
<220> FEATURE:
<223> OTHER INFORMATION: A83F-F primer

<400> SEQUENCE: 91
ggtgagttcg cacaccaaat ttcggcg 27

<210> SEQ ID NO 92
<211> LENGTH: 25
<212> TYPE: DNA
<213> ORGANISM: Artificial Sequence
<220> FEATURE:
<223> OTHER INFORMATION: A83F-R primer

<400> SEQUENCE: 92
gtgtgcgaac tcaccggcat agccc 25

<210> SEQ ID NO 93
<211> LENGTH: 27
<212> TYPE: DNA
<213> ORGANISM: Artificial Sequence
<220> FEATURE:
<223> OTHER INFORMATION: A83G-F primer

<400> SEQUENCE: 93
ggtgagggcg cacaccaaat ttcggcg 27

<210> SEQ ID NO 94
<211> LENGTH: 25
<212> TYPE: DNA
<213> ORGANISM: Artificial Sequence
<220> FEATURE:
<223> OTHER INFORMATION: A83G-R primer

<400> SEQUENCE: 94
gtgtgcgccc tcaccggcat agccc 25

<210> SEQ ID NO 95
<211> LENGTH: 27
<212> TYPE: DNA
<213> ORGANISM: Artificial Sequence
<220> FEATURE:
<223> OTHER INFORMATION: A83H-F primer

<400> SEQUENCE: 95
ggtgagcacg cacaccaaat ttcggcg 27

<210> SEQ ID NO 96
<211> LENGTH: 25
<212> TYPE: DNA
<213> ORGANISM: Artificial Sequence
<220> FEATURE:
<223> OTHER INFORMATION: A83H-R primer

<400> SEQUENCE: 96
gtgtgcgtgc tcaccggcat agccc 25

<210> SEQ ID NO 97
<211> LENGTH: 27
<212> TYPE: DNA
<213> ORGANISM: Artificial Sequence
<220> FEATURE:
<223> OTHER INFORMATION: A83M-F primer

<400> SEQUENCE: 97
ggtgagatgg cacaccaaat ttcggcg 27

<210> SEQ ID NO 98
<211> LENGTH: 25
<212> TYPE: DNA
<213> ORGANISM: Artificial Sequence
<220> FEATURE:
<223> OTHER INFORMATION: A83M-R primer

<400> SEQUENCE: 98
gtgtgccatc tcaccggcat agccc 25

<210> SEQ ID NO 99
<211> LENGTH: 27
<212> TYPE: DNA
<213> ORGANISM: Artificial Sequence
<220> FEATURE:
<223> OTHER INFORMATION: A83P-F primer

<400> SEQUENCE: 99
ggtgagccgg cacaccaaat ttcggcg 27

<210> SEQ ID NO 100
<211> LENGTH: 25
<212> TYPE: DNA
<213> ORGANISM: Artificial Sequence
<220> FEATURE:
<223> OTHER INFORMATION: A83P-R primer

<400> SEQUENCE: 100
gtgtgccggc tcaccggcat agccc 25

<210> SEQ ID NO 101
<211> LENGTH: 27
<212> TYPE: DNA
<213> ORGANISM: Artificial Sequence
<220> FEATURE:
<223> OTHER INFORMATION: A83S-F primer

<400> SEQUENCE: 101
ggtgagtccg cacaccaaat ttcggcg 27

<210> SEQ ID NO 102
<211> LENGTH: 25
<212> TYPE: DNA
<213> ORGANISM: Artificial Sequence
<220> FEATURE:
<223> OTHER INFORMATION: A83S-R primer

<400> SEQUENCE: 102
gtgtgcggac tcaccggcat agccc 25

<210> SEQ ID NO 103
<211> LENGTH: 27
<212> TYPE: DNA
<213> ORGANISM: Artificial Sequence
<220> FEATURE:
<223> OTHER INFORMATION: A83T-F primer

<400> SEQUENCE: 103
ggtgagaccg cacaccaaat ttcggcg 27

<210> SEQ ID NO 104
<211> LENGTH: 25
<212> TYPE: DNA
<213> ORGANISM: Artificial Sequence
<220> FEATURE:
<223> OTHER INFORMATION: A83T-R primer

<400> SEQUENCE: 104
gtgtgcggtc tcaccggcat agccc 25

<210> SEQ ID NO 105
<211> LENGTH: 203
<212> TYPE: PRT
<213> ORGANISM: Rhodococcus rhodochrous M8

<400> SEQUENCE: 105

```
Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190
```

```
Ser Asn Ala Leu Thr Pro Gln Glu Val Ile Val
        195                 200


<210> SEQ ID NO 106
<211> LENGTH: 203
<212> TYPE: PRT
<213> ORGANISM: Rhodococcus ruber TH

<400> SEQUENCE: 106

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
        195                 200


<210> SEQ ID NO 107
<211> LENGTH: 203
<212> TYPE: PRT
<213> ORGANISM: Rhodococcus pyridinivorans MW33

<400> SEQUENCE: 107

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110
```

-continued

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200

<210> SEQ ID NO 108
<211> LENGTH: 203
<212> TYPE: PRT
<213> ORGANISM: Rhodococcus pyridinivorans S85-2

<400> SEQUENCE: 108

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200

<210> SEQ ID NO 109
<211> LENGTH: 203
<212> TYPE: PRT
<213> ORGANISM: Nocardia sp. JBRs

<400> SEQUENCE: 109

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

-continued

```
Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
        195                 200


<210> SEQ ID NO 110
<211> LENGTH: 203
<212> TYPE: PRT
<213> ORGANISM: Nocardia sp. YS-2002

<400> SEQUENCE: 110

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
```

195 200

<210> SEQ ID NO 111
<211> LENGTH: 203
<212> TYPE: PRT
<213> ORGANISM: uncultured bacterium BD2

<400> SEQUENCE: 111

Met Ser Glu His Val Asn Lys Tyr Thr Glu Tyr Glu Ala Arg Thr Lys
1 5 10 15

Ala Ile Glu Thr Leu Leu Tyr Glu Arg Gly Leu Ile Thr Pro Ala Ala
20 25 30

Val Asp Arg Val Val Ser Tyr Tyr Glu Asn Glu Ile Gly Pro Met Gly
35 40 45

Gly Ala Lys Val Val Ala Lys Ser Trp Val Asp Pro Glu Tyr Arg Lys
50 55 60

Trp Leu Glu Glu Asp Ala Thr Ala Ala Met Ala Ser Leu Gly Tyr Ala
65 70 75 80

Gly Glu Gln Ala His Gln Ile Ser Ala Val Phe Asn Asp Ser Gln Thr
85 90 95

His His Val Val Val Cys Thr Leu Cys Ser Cys Tyr Pro Trp Pro Val
100 105 110

Leu Gly Leu Pro Pro Ala Trp Tyr Lys Ser Met Glu Tyr Arg Ser Arg
115 120 125

Val Val Ala Asp Pro Arg Gly Val Leu Lys Arg Asp Phe Gly Phe Asp
130 135 140

Ile Pro Asp Glu Val Glu Val Arg Val Trp Asp Ser Ser Ser Glu Ile
145 150 155 160

Arg Tyr Ile Val Ile Pro Glu Arg Pro Ala Gly Thr Asp Gly Trp Ser
165 170 175

Glu Glu Glu Leu Thr Lys Leu Val Ser Arg Asp Ser Met Ile Gly Val
180 185 190

Ser Asn Ala Leu Thr Pro Gln Glu Val Ile Val
195 200

<210> SEQ ID NO 112
<211> LENGTH: 180
<212> TYPE: PRT
<213> ORGANISM: uncultured bacterium SP1

<400> SEQUENCE: 112

Met Ser Glu His Val Asn Lys Tyr Thr Glu Tyr Glu Ala Arg Thr Lys
1 5 10 15

Ala Val Glu Thr Leu Leu Tyr Glu Arg Gly Leu Ile Thr Pro Ala Ala
20 25 30

Val Asp Arg Val Val Ser Tyr Tyr Glu Asn Glu Ile Gly Pro Met Gly
35 40 45

Gly Ala Lys Val Val Ala Lys Ser Trp Val Asp Pro Glu Tyr Arg Lys
50 55 60

Trp Leu Glu Glu Asp Ala Thr Ala Ala Met Ala Ser Leu Gly Tyr Ala
65 70 75 80

Gly Glu Gln Ala His His Val Val Val Cys Thr Leu Cys Ser Cys Tyr
85 90 95

Pro Trp Pro Val Leu Gly Leu Pro Pro Ala Trp Tyr Lys Ser Met Glu
100 105 110

Tyr Arg Ser Arg Val Val Ala Asp Pro Arg Gly Val Leu Lys Arg Asp

```
        115                 120                 125

Phe Gly Phe Asp Ile Pro Asp Glu Val Glu Val Arg Val Trp Asp Ser
    130                 135                 140

Ser Ser Glu Ile Arg Tyr Ile Val Ile Pro Glu Arg Pro Ala Gly Thr
145                 150                 155                 160

Asp Gly Trp Ser Glu Glu Glu Leu Thr Lys Leu Val Ser Arg Asp Ser
                165                 170                 175

Ile Ile Gly Val
            180


<210> SEQ ID NO 113
<211> LENGTH: 205
<212> TYPE: PRT
<213> ORGANISM: Pseudonocardia thermophila JCM3095

<400> SEQUENCE: 113

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Asn
        35                  40                  45

Glu Val Gly Pro His Leu Gly Ala Lys Val Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
                85                  90                  95

Glu Asn Thr Asp Glu Val His His Val Val Val Cys Thr Leu Cys Ser
            100                 105                 110

Cys Tyr Pro Trp Pro Val Leu Gly Leu Pro Pro Asn Trp Phe Lys Glu
        115                 120                 125

Pro Gln Tyr Arg Ser Arg Val Val Arg Glu Pro Arg Gln Leu Leu Lys
    130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Glu Leu Ala Thr Leu Val Thr Arg
            180                 185                 190

Glu Ser Met Ile Gly Val Glu Pro Ala Lys Ala Val Ala
        195                 200                 205


<210> SEQ ID NO 114
<211> LENGTH: 207
<212> TYPE: PRT
<213> ORGANISM: Rhodococcus rhodochrous Cr4

<400> SEQUENCE: 114

Met Thr Ala His Asn Pro Val Gln Gly Thr Phe Pro Arg Ser Asn Glu
1               5                   10                  15

Glu Ile Ala Ala Arg Val Lys Ala Met Glu Ala Ile Leu Val Asp Lys
            20                  25                  30

Gly Leu Ile Ser Thr Asp Ala Ile Asp Tyr Met Ser Ser Val Tyr Glu
        35                  40                  45

Asn Glu Val Gly Pro Gln Leu Gly Ala Lys Ile Ala Ala His Ala Trp
```

```
    50                  55                  60

Val Asp Pro Glu Phe Lys Gln Arg Leu Leu Ala Asp Ala Thr Gly Ala
65                  70                  75                  80

Cys Lys Glu Met Gly Val Gly Gly Met Gln Gly Glu Glu Met Val Val
                85                  90                  95

Leu Glu Asn Thr Asp Thr Val Asn Asn Met Val Val Cys Thr Leu Cys
            100                 105                 110

Ser Cys Tyr Pro Trp Pro Val Leu Gly Leu Pro Pro Asn Trp Tyr Lys
        115                 120                 125

Tyr Pro Ala Tyr Arg Ala Arg Ala Ala Arg Asp Pro Arg Gly Val Met
    130                 135                 140

Ala Glu Phe Gly Tyr Thr Pro Ala Ser Asp Val Glu Ile Arg Val Trp
145                 150                 155                 160

Asp Ser Ser Ala Glu Leu Arg Tyr Trp Val Leu Pro Gln Arg Pro Ala
                165                 170                 175

Gly Thr Glu Asn Phe Thr Glu Glu Gln Leu Ala Ala Leu Val Thr Arg
            180                 185                 190

Asp Ser Leu Ile Gly Val Ser Val Pro Thr Ala Pro Asn Lys Ala
        195                 200                 205


<210> SEQ ID NO 115
<211> LENGTH: 32
<212> TYPE: DNA
<213> ORGANISM: Artificial Sequence
<220> FEATURE:
<223> OTHER INFORMATION: M8-1 primer

<400> SEQUENCE: 115

ggtctagaat ggatggtatc cacgacacag gc                                   32


<210> SEQ ID NO 116
<211> LENGTH: 34
<212> TYPE: DNA
<213> ORGANISM: Artificial Sequence
<220> FEATURE:
<223> OTHER INFORMATION: M8-2 primer

<400> SEQUENCE: 116

cccctgcagg tcagtcgatg atggccatcg attc                                 34


<210> SEQ ID NO 117
<211> LENGTH: 6
<212> TYPE: PRT
<213> ORGANISM: Rhodococcus N-771

<400> SEQUENCE: 117

Cys Ser Leu Cys Ser Cys
1               5


<210> SEQ ID NO 118
<211> LENGTH: 6
<212> TYPE: PRT
<213> ORGANISM: Rhodococcus rhodochrous J1

<400> SEQUENCE: 118

Cys Thr Leu Cys Ser Cys
1               5


<210> SEQ ID NO 119
<211> LENGTH: 11
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa is Ala, Leu, Met, Asn, Cys, Asp, Glu, Phe,
      Gly, His, Lys, Pro, Arg, Ser, Thr or Trp

<400> SEQUENCE: 119

Ala Xaa Xaa Xaa Xaa Gly Xaa Xaa Gly Xaa Xaa
1               5                   10


<210> SEQ ID NO 120
<211> LENGTH: 203
<212> TYPE: PRT
<213> ORGANISM: Rhodococcus rhodochrous J1
<220> FEATURE:
<221> NAME/KEY: misc_feature
<222> LOCATION: (74)..(77)
<223> OTHER INFORMATION: Xaa can be any naturally occurring amino acid
<220> FEATURE:
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa is Ala, Leu, Met, Asn, Cys, Asp, Glu, Phe,
      Gly, His, Lys, Pro, Arg, Ser, Thr or Trp

<400> SEQUENCE: 120

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Xaa Xaa Xaa Xaa Gly Xaa Xaa
65                  70                  75                  80

Gly Xaa Xaa Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
```

```
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200


<210> SEQ ID NO 121
<211> LENGTH: 203
<212> TYPE: PRT
<213> ORGANISM: Rhodococcus pyridinivorans MS-38

<400> SEQUENCE: 121

Val Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200


<210> SEQ ID NO 122
<211> LENGTH: 203
<212> TYPE: PRT
<213> ORGANISM: Rhodococcus rhodochrous ATCC39384

<400> SEQUENCE: 122

Val Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
```

```
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
        195                 200


<210> SEQ ID NO 123
<211> LENGTH: 213
<212> TYPE: PRT
<213> ORGANISM: Sinorhizobium medicae WSM419

<400> SEQUENCE: 123

Met Ser Glu His Arg His Gly Pro Gly Glu Glu His Gly His His His
1               5                   10                  15

Asp Asn His Leu Thr Asp Met Glu Ala Arg Val Lys Ala Leu Glu Thr
            20                  25                  30

Val Leu Thr Glu Lys Gly Leu Ile Asp Pro Ala Ala Ile Asp Ala Ile
        35                  40                  45

Val Asp Thr Tyr Glu Thr Lys Val Gly Pro Arg Asn Gly Ala Arg Val
    50                  55                  60

Val Ala Lys Ala Trp Ser Asp Pro Asp Phe Ala Asp Trp Leu Arg Arg
65                  70                  75                  80

Asp Ala Thr Ala Ala Ile Ala Ser Leu Gly Phe Thr Gly Arg Gln Gly
                85                  90                  95

Glu His Met Arg Ala Val Phe Asn Thr Ser Glu Thr His Asn Leu Ile
            100                 105                 110

Val Cys Thr Leu Cys Ser Cys Tyr Pro Trp Ala Val Leu Gly Leu Pro
        115                 120                 125

Pro Val Trp Tyr Lys Ala Pro Pro Tyr Arg Ser Arg Ala Val Ile Asp
    130                 135                 140

Pro Arg Gly Val Leu Ala Glu Phe Gly Leu Asn Leu Pro Ala Glu Lys
145                 150                 155                 160

Lys Ile Arg Val Trp Asp Ser Thr Ala Glu Leu Arg Tyr Leu Val Val
                165                 170                 175

Pro Glu Arg Pro Ala Ala Thr Asp Asp Leu Gly Glu Asp Ala Leu Ala
            180                 185                 190

Lys Leu Val Thr Arg Asp Ser Met Ile Gly Thr Gly Leu Ala Leu Ser
        195                 200                 205

Pro Glu Ala Phe Arg
    210


<210> SEQ ID NO 124
<211> LENGTH: 205
```

```
<212> TYPE: PRT
<213> ORGANISM: Geobacillus thermoglucosidasius Q6

<400> SEQUENCE: 124

Met Ser Val Gln Lys Val His His Asn Val Leu Pro Glu Lys Pro Ala
1               5                   10                  15

Gln Thr Arg Thr Lys Ala Leu Glu Ser Leu Leu Ile Glu Ser Gly Leu
            20                  25                  30

Val Ser Thr Asp Ala Leu Asp Ala Ile Ile Glu Ala Tyr Glu Asn Asp
        35                  40                  45

Ile Gly Pro Met Asn Gly Ala Lys Val Val Ala Lys Ala Trp Val Asp
    50                  55                  60

Pro Asp Tyr Lys Glu Arg Leu Leu Arg Asp Gly Thr Ser Ala Ile Ala
65                  70                  75                  80

Glu Leu Gly Phe Leu Gly Leu Gln Gly Glu His Met Val Val Val Glu
                85                  90                  95

Asn Thr Pro Lys Val His Asn Val Val Val Cys Thr Leu Cys Ser Cys
            100                 105                 110

Tyr Pro Trp Pro Val Leu Gly Leu Pro Pro Ser Trp Tyr Lys Ser Ala
        115                 120                 125

Ser Tyr Arg Ala Arg Ile Val Ser Glu Pro Arg Thr Val Leu Lys Glu
    130                 135                 140

Phe Gly Leu Glu Leu Asp Asp Asp Val Glu Ile Arg Val Trp Asp Ser
145                 150                 155                 160

Ser Ala Glu Ile Arg Tyr Leu Val Leu Pro Glu Arg Pro Ala Gly Thr
                165                 170                 175

Glu Gly Trp Ser Glu Glu Glu Leu Ala Lys Leu Val Thr Arg Asp Ser
            180                 185                 190

Met Ile Gly Val Ala Lys Ile Lys Ser Pro Val Lys Lys
        195                 200                 205


<210> SEQ ID NO 125
<211> LENGTH: 210
<212> TYPE: PRT
<213> ORGANISM: Comamonas testosteroni

<400> SEQUENCE: 125

Met Gly Gln Ser His Thr His Asp His His His Asp Gly Tyr Gln Ala
1               5                   10                  15

Pro Pro Glu Asp Ile Ala Leu Arg Val Lys Ala Leu Glu Ser Leu Leu
            20                  25                  30

Ile Glu Lys Gly Leu Val Asp Pro Ala Ala Met Asp Leu Val Val Gln
        35                  40                  45

Thr Tyr Glu His Lys Val Gly Pro Arg Asn Gly Ala Lys Val Val Ala
    50                  55                  60

Lys Ala Trp Val Asp Pro Ala Tyr Lys Ala Arg Leu Leu Ala Asp Gly
65                  70                  75                  80

Thr Ala Gly Ile Ala Glu Leu Gly Phe Ser Gly Val Gln Gly Glu Asp
                85                  90                  95

Met Val Ile Leu Glu Asn Thr Pro Ala Val His Asn Val Val Val Cys
            100                 105                 110

Thr Leu Cys Ser Cys Tyr Pro Trp Pro Thr Leu Gly Leu Pro Pro Ala
        115                 120                 125

Trp Tyr Lys Ala Pro Pro Tyr Arg Ser Arg Met Val Ser Asp Pro Arg
    130                 135                 140
```

-continued

```
Gly Val Leu Ala Glu Phe Gly Leu Val Ile Pro Ala Lys Glu Ile Arg
145                 150                 155                 160

Val Trp Asp Thr Thr Ala Glu Leu Arg Tyr Met Val Leu Pro Glu Arg
                165                 170                 175

Pro Ala Gly Thr Glu Ala Tyr Ser Glu Glu Gln Leu Ala Glu Leu Val
            180                 185                 190

Thr Arg Asp Ser Met Ile Gly Thr Gly Leu Pro Ile Gln Pro Thr Pro
        195                 200                 205

Ser His
    210


<210> SEQ ID NO 126
<211> LENGTH: 203
<212> TYPE: PRT
<213> ORGANISM: Rhodococcus ruber RH

<400> SEQUENCE: 126

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
        195                 200


<210> SEQ ID NO 127
<211> LENGTH: 27
<212> TYPE: DNA
<213> ORGANISM: Artificial Sequence
<220> FEATURE:
<223> OTHER INFORMATION: A83N-F primer

<400> SEQUENCE: 127

ggtgagaacg cacaccaaat ttcggcg                                          27


<210> SEQ ID NO 128
<211> LENGTH: 25
<212> TYPE: DNA
<213> ORGANISM: Artificial Sequence
```

<220> FEATURE:
<223> OTHER INFORMATION: A83N-R primer

<400> SEQUENCE: 128
gtgtgcgttc tcaccggcat agccc 25

<210> SEQ ID NO 129
<211> LENGTH: 27
<212> TYPE: DNA
<213> ORGANISM: Artificial Sequence
<220> FEATURE:
<223> OTHER INFORMATION: A82RM-F primer
<220> FEATURE:
<221> NAME/KEY: misc_feature
<222> LOCATION: (9)..(10)
<223> OTHER INFORMATION: n is a, c, g, or t

<400> SEQUENCE: 129
atgccggtnn scaggcacac caaattt 27

<210> SEQ ID NO 130
<211> LENGTH: 27
<212> TYPE: DNA
<213> ORGANISM: Artificial Sequence
<220> FEATURE:
<223> OTHER INFORMATION: A82RM-R primer
<220> FEATURE:
<221> NAME/KEY: misc_feature
<222> LOCATION: (10)..(11)
<223> OTHER INFORMATION: n is a, c, g, or t

<400> SEQUENCE: 130
tgtgcctgsn naccggcata gcccaat 27

<210> SEQ ID NO 131
<211> LENGTH: 203
<212> TYPE: PRT
<213> ORGANISM: Rhodococcus rhodochrous J1
<220> FEATURE:
<221> NAME/KEY: misc_feature
<222> LOCATION: (74)..(77)
<223> OTHER INFORMATION: Xaa can be any naturally occurring amino acid
<220> FEATURE:
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa is not wild type amino acid

<400> SEQUENCE: 131

```
Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Xaa Xaa Xaa Xaa Gly Xaa Xaa
65                  70                  75                  80

Gly Xaa Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110
```

```
Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200
```

<210> SEQ ID NO 132
<211> LENGTH: 11
<212> TYPE: PRT
<213> ORGANISM: Artificial Sequence
<220> FEATURE:
<223> OTHER INFORMATION: Specific amino acid residue
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa is not wild type amino acid

<400> SEQUENCE: 132

```
Ala Xaa Xaa Xaa Xaa Gly Xaa Xaa Gly Xaa Gln
1               5                   10
```

<210> SEQ ID NO 133
<211> LENGTH: 27
<212> TYPE: DNA
<213> ORGANISM: Artificial Sequence
<220> FEATURE:
<223> OTHER INFORMATION: A85RM-F primer
<220> FEATURE:
<221> NAME/KEY: misc_feature
<222> LOCATION: (7)..(8)
<223> OTHER INFORMATION: n is a, c, g, or t

<400> SEQUENCE: 133
caggcannsc aaatttcggc ggtcttc 27

<210> SEQ ID NO 134
<211> LENGTH: 27
<212> TYPE: DNA
<213> ORGANISM: Artificial Sequence
<220> FEATURE:
<223> OTHER INFORMATION: A85RM-R primer
<220> FEATURE:
<221> NAME/KEY: misc_feature
<222> LOCATION: (8)..(9)
<223> OTHER INFORMATION: n is a, c, g, or t

<400> SEQUENCE: 134
aatttgsnnt gcctgctcac cggcata 27

<210> SEQ ID NO 135
<211> LENGTH: 203

-continued

```
<212> TYPE: PRT
<213> ORGANISM: Rhodococcus rhodochrous J1
<220> FEATURE:
<221> NAME/KEY: misc_feature
<222> LOCATION: (74)..(77)
<223> OTHER INFORMATION: Xaa can be any naturally occurring amino acid
<220> FEATURE:
<221> NAME/KEY: misc_feature
<222> LOCATION: (79)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa is not wild type amino acid

<400> SEQUENCE: 135

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Xaa Xaa Xaa Xaa Gly Xaa Xaa
65                  70                  75                  80

Gly Xaa Gln Xaa Xaa Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200


<210> SEQ ID NO 136
<211> LENGTH: 13
<212> TYPE: PRT
<213> ORGANISM: Artificial Sequence
<220> FEATURE:
<223> OTHER INFORMATION: Specific amino acid residue
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid
```

-continued

<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa is not wild type amino acid

<400> SEQUENCE: 136

```
Ala Xaa Xaa Xaa Xaa Gly Xaa Xaa Gly Xaa Gln Xaa Xaa
1               5                   10
```

NITRILE HYDRATASE

This application is a continuation of U.S. application Ser. No. 14/124,555 filed Dec. 6, 2013, allowed, which is a National Stage of PCT/JP12/003745 filed Jun. 7, 2012 and claims the benefit of JP 2011-127466 filed Jun. 7, 2011, JP 2011-144378 filed Jun. 29, 2011 and JP 2011-145061 filed Jun. 30, 2011.

TECHNICAL FIELD

The present invention relates to improving a nitrile hydratase (mutation) and its production method. Moreover, the present invention relates to genomic DNA that encodes the enzyme, a recombinant vector containing the genomic DNA, a transformant containing the recombinant vector, and a method for producing an amide compound.

DESCRIPTION OF BACKGROUND ART

In recent years, a nitrile hydratase was found, which is an enzyme having nitrile hydrolysis activity that catalyses the hydration of a nitrile group to its corresponding amide group. Also, methods are disclosed to produce corresponding amide compounds from nitrile compounds using the enzyme or a microbial cell or the like containing the enzyme. Compared with conventional chemical synthetic methods, such methods are known by a high conversion or selectivity rate from a nitrile compound to a corresponding amide compound.

Examples of microorganisms that produce a nitrile hydratase are the genus *Corynebacterium*, genus *Pseudomonas*, genus *Rhodococcus*, genus *Rhizobium*, genus *Klebsiella*, genus *Pseudonocardia* and the like. Among those, *Rhodococcus rhodochrous* strain J1 has been used for industrial production of acrylamides, and its usefulness has been verified. Furthermore, a gene encoding a nitrile hydratase produced by strain J1 has been identified (see patent publication 1).

Meanwhile, introducing a mutation into a nitrile hydratase has been attempted not only to use a nitrile hydratase isolated from a naturally existing microorganism or its gene, but also to change its activity, substrate specificity, Vmax, Km, heat stability, stability in a substrate, stability in a subsequent product and the like of a nitrile hydratase. Regarding the nitrile hydratase in *Pseudonocardia thermophila* JCM 3095, from its conformational data, sites relating to the substrate specificity or thermal stability are anticipated, and mutant enzymes with modified substrate specificity were obtained (see patent publications 2~4). Also, nitrile hydratase genes with improved heat resistance and amide-compound resistance have been produced by the inventors of the present invention (see patent publications 5~9).

To produce acrylamide for industrial applications using enzyme production methods, it is useful to develop a nitrile hydratase with improved catalytic activity when production costs such as catalyst costs are considered. Developing enzymes with improved activity is especially desired so as to achieve a reduction in the enzyme amount for reactions and in production costs or the like.

PRIOR ART PUBLICATION

Patent Publication

Patent publication 1: Japanese patent publication 3162091

Patent publication 2: International publication pamphlet WO2004/056990

Patent publication 3: Japanese laid-open patent publication 2004-194588

Patent publication 4: Japanese laid-open patent publication 2005-16403

Patent publication 5: International publication pamphlet WO2005/116206

Patent publication 6: Japanese laid-open patent publication 2007-143409

Patent publication 7: Japanese laid-open patent publication 2007-43910

Patent publication 8: Japanese laid-open patent publication 2008-253182

Patent publication 9: Japanese laid-open patent publication 2010-172295

SUMMARY OF THE INVENTION

Problems to be Solved by the Invention

The objective of the present invention is to improve a nitrile hydratase so as to provide an improved nitrile hydratase with enhanced catalytic activity. Another objective of the present invention is to provide a nitrile hydratatse collected from DNA encoding such an improved nitrile hydratase, a recombinant vector containing the DNA, a transformant containing the recombinant vector, and a culture of the transformant, as well as a method for producing such a nitrile hydratase. Yet another objective of the present invention is to provide a method for producing an amide compound using the culture or the processed product of the culture.

Solutions to the Problems

The inventors of the present invention have conducted extensive studies to solve the above problems. As a result, in the amino acid sequence of a nitrile hydatase, the inventors have found that a protein in which a specific amino-acid residue is substituted with another amino-acid residue has nitrile hydratase activity and exhibits enhanced catalytic activity. Accordingly, the present invention is completed.

Namely, the present invention is described as follows.

(1) An improved nitrile hydratase characterized by at least one of the following (a)~(e):

(a) in the β subunit, a nitrile hydratase contains an amino-acid sequence as shown in SEQ ID NO: 50 below $GX_1X_2X_3X_4DX_5X_6R$ (SEQ ID NO: 50)

(G is glycine, D is aspartic acid, R is arginine, and $X_1$, $X_2$, $X_3$, $X_5$ and $X_6$ each independently indicate any amino-acid residue), in which $X_4$ is an amino acid selected from among cysteine, aspartic acid, glutamic acid, histidine, isoleucine, lysine, methionine, asparagine, proline, glutamine, serine and threonine;

(b) in the β subunit, a nitrile hydratase contains an amino-acid sequence as shown in SEQ ID NO: 81 below $WEX_1X_2X_3X_4X_5X_6X_7X_8X_9X_{10}X_{11}X_{12}X_{13}X_{14}X_{15}X_{16}X_{17}X_{18}D$ (SEQ ID NO: 81)

(W is tryptophan, E is glutamic acid, D is aspartic acid, and $X_1$~$X_6$, and $X_8$~$X_{18}$ each independently indicate any amino-acid residue), in which $X_7$ is an amino acid selected from among alanine, valine, aspartic acid, threonine, phenylalanine, isoleucine and methionine;

(c) in the α subunit, a nitrile hydratase contains an amino-acid sequence as shown in SEQ ID NO: 119 below $AX_1X_2X_3X_4GX_5X_6GX_7X_8$ (SEQ ID NO: 119)

(A is alanine, G is glycine, and $X_1$~$X_7$ independently indicate any amino-acid residue), in which $X_8$ is an amino acid selected from among alanine, leucine, methionine, asparagine, cysteine, aspartic acid, glutamic acid, phenylalanine, glycine, histidine, lysine, proline, arginine, serine, threonine and tryptophan;

(d) in the α subunit, a nitrile hydratase has the amino-acid sequence as shown in SEQ ID NO: 132 below, $AX_1X_2X_3X_4GX_5X_6GX_7Q$ (SEQ ID NO: 132)

(A is alanine, G is glycine, Q is glutamine, and $X_1$~$X_6$ each independently indicate any amino-acid residue), in which $X_7$ is substituted with an amino acid different from that in a wild type;

(e) in the α subunit, a nitrile hydratase has the amino-acid sequence as shown in SEQ ID NO: 136 below $AX_1X_2X_3X_4GX_5X_6GX_7QX_8X_9$ (SEQ ID NO: 136)

(A is alanine, G is glycine, Q is glutamine, and $X_1$~$X_8$ each independently indicate any amino-acid residue), in which $X_9$ is substituted with an amino acid different from that in a wild type.

(2) The improved nitrile hydratase described in (1), characterized in that $X_2$ in SEQ ID NO: 50 is S (serine).

(3) The improved nitrile hydratase described in (1), characterized in that $X_1$ is I (isoleucine), $X_2$ is S (serine), $X_3$ is W (tryptophan), $X_5$ is K (lysine), and $X_6$ is S (serine) in SEQ ID NO: 50.

(4) The improved nitrile hydratase described in any of (1)~(3), having an amino-acid sequence as shown in SEQ ID NO: 51 that includes the amino-acid sequence as shown in SEQ ID NO: 50.

(5) The improved nitrile hydratase described in (1), characterized in that $X_{14}$ in SEQ ID NO: 81 is G (glycine).

(6) The improved nitrile hydratase described in (1), characterized in that $X_1$ is G (glycine), $X_2$ is R (arginine), $X_3$ is T (threonine), $X_4$ is L (leucine), $X_5$ is S (serine), $X_6$ is I (isoleucine), $X_8$ is T (threonine), $X_9$ is W (tryptophan), $X_{10}$ is M (methionine), $X_{11}$ is H (histidine), $X_{12}$ is L (leucine), $X_{13}$ is K (lysine), and $X_{14}$ is G (glycine) in SEQ ID NO: 81.

(7) The improved nitrile hydratase described in any of (1), (5) and (6), having an amino-acid sequence as shown in SEQ ID NO: 82 that includes the amino-acid sequence as shown in SEQ ID NO: 81.

(8) The improved nitrile hydratase described in (1), characterized in that $X_1$ is M (methionine), $X_2$ is A (alanine), $X_3$ is S (serine), $X_4$ is L (leucine), $X_5$ is Y (tyrosine), $X_6$ is A (alanine) and $X_7$ is E (glutamic acid) in SEQ ID NO: 119.

(9) The improved nitrile hydratase described in (1) or (8), having an amino-acid sequence as shown in SEQ ID NO: 120 that includes the amino-acid sequence as shown in SEQ ID NO: 119.

(10) The improved nitrile hydratase described in (1), characterized by containing the amino-acid sequence of the α subunit as shown in SEQ ID NO: 132, in which $X_7$ is an amino acid selected from among cysteine, phenylalanine, histidine, isoleucine, lysine, methionine, glutamine, arginine, threonine and tyrosine.

(11) The improved nitrile hydratase described in (1) or (10), characterized in that $X_1$ is M (methionine), $X_2$ is A (alanine), $X_3$ is S (serine), $X_4$ is L (leucine), $X_5$ is Y (tyrosine), and $X_6$ is A (alanine) in SEQ ID NO: 132.

(12) The improved nitrile hydratase described in (1), (10) or (11), having an amino-acid sequence as shown in SEQ ID NO: 131 that includes the amino-acid sequence as shown in SEQ ID NO: 132.

(13) The improved nitrile hydratase described in (1), characterized by containing an amino-acid sequence of the α subunit as shown in SEQ ID NO: 136, in which $X_9$ is an amino acid selected from among cysteine, glutamic acid, phenylalanine, isoleucine, asparagine, glutamine, serine and tyrosine.

(14) The improved nitrile hydratase described in (1) or (13), characterized in that $X_1$ is M (methionine), $X_2$ is A (alanine), $X_3$ is S (serine), $X_4$ is L (leucine), $X_5$ is Y (tyrosine), $X_6$ is A (alanine), $X_7$ is E (glutamic acid), and $X_8$ is A (alanine) in SEQ ID NO: 136.

(15) The improved nitrile hydratase described in (1), (13) or (14), having an amino-acid sequence as shown in SEQ ID NO: 135 that includes the amino-acid sequence as shown in SEQ ID NO: 136.

(16) The improved nitrile hydratase described in any one of (1) to (15) is a nitrile hydratase derived from *Rhodococcus* bacterium or *Nocardia* bacterium.

(17) DNA encoding the improved nitrile hydratase described in any one of (1) to (16).

(18) DNA hybridized with the DNA described in (17) under stringent conditions.

(19) A recombinant vector containing the DNA described in (17) or (18).

(20) A transformant containing the recombinant vector described in (19).

(21) A nitrile hydratase collected from a culture obtained by incubating the transformant described in (20).

(22) A method for producing a nitrile hydratase, such a method characterized by incubating the transformant described in (20) and by collecting the nitrile hydratase from the obtained culture.

(23) A method for producing an amide compound, such a method characterized by bringing a nitrile compound into contact with a culture, or a processed product of the culture, obtained by incubating the improved nitrile hydratase described in any of (1)~(16) or the transformant described in (20).

Effects of the Invention

According to the present invention, a novel improved (mutant) nitrile hydratase is obtained to have enhanced catalytic activity. The improved nitrile hydratase with enhanced catalytic activity is very useful to produce amide compounds at a high yield.

According to the present invention, an improved nitrile hydratase and its production method are provided; such a nitrile hydratase is obtained from genomic DNA encoding the improved nitrile hydratase, a recombinant vector containing the genomic DNA, a transformant containing the recombinant vector and a culture of the transformant. Also provided by the present invention is a method for producing an amide compound using the protein (improved nitrile hydratase) and the culture or a processed product of the culture.

BRIEF DESCRIPTION OF THE DRAWINGS

FIG. 2-1 is a list showing the alignment results in β subunits of known nitrile hydratases;

FIG. 2-2 is a list showing the alignment results in β subunits of known nitrile hydratases;

FIG. 3 shows the amino-acid sequence of the β subunit identified as SEQ ID NO: 51 related to the present invention;

FIG. 6-1 is a list showing amino-acid sequences (part of N-terminal side) of β subunits in wild-type nitrile hydratases derived from various microorganisms;

FIG. 6-2 is a list showing amino-acid sequences (part of C-terminal side) subsequent to the amino-acid sequences in FIG. 6-1;

FIG. 7 shows the amino-acid sequence in the β subunit identified as SEQ ID NO: 82 related to the present invention;

FIG. 8-1 is a list showing amino-acid sequences (part of N-terminal side) in α subunits of nitrile hydratases derived from various microorganisms;

FIG. 8-2 is a list showing amino-acid sequences subsequent to the amino-acid sequences in FIG. 8-1;

FIG. 9 shows the amino-acid sequence in the α subunit identified as SEQ ID NO: 121 related to the present invention;

FIG. 10-1 is a list showing amino-acid sequences (part of N-terminal side) in α subunits of nitrile hydratases derived from various microorganisms;

FIG. 10-2 is a list showing amino-acid sequences the same as in FIG. 2-1, and shows the sequences subsequent to the amino-acid sequences in FIG. 10-1;

FIG. 11 shows the amino-acid sequence in the α subunit identified as SEQ ID NO: 131 related the present invention;

FIG. 12-1 is a list showing amino-acid sequences (part of N-terminal side) in α subunits of nitrile hydratases derived from various microorganisms;

FIG. 12-2 is a list showing amino-acid sequences subsequent to the amino-acid sequences in FIG. 12-1; and FIG. 13 shows the amino-acid sequence in the α subunit identified as SEQ ID NO: 135 related to the present invention.

MODE TO CARRY OUT THE INVENTION

Figure 1:
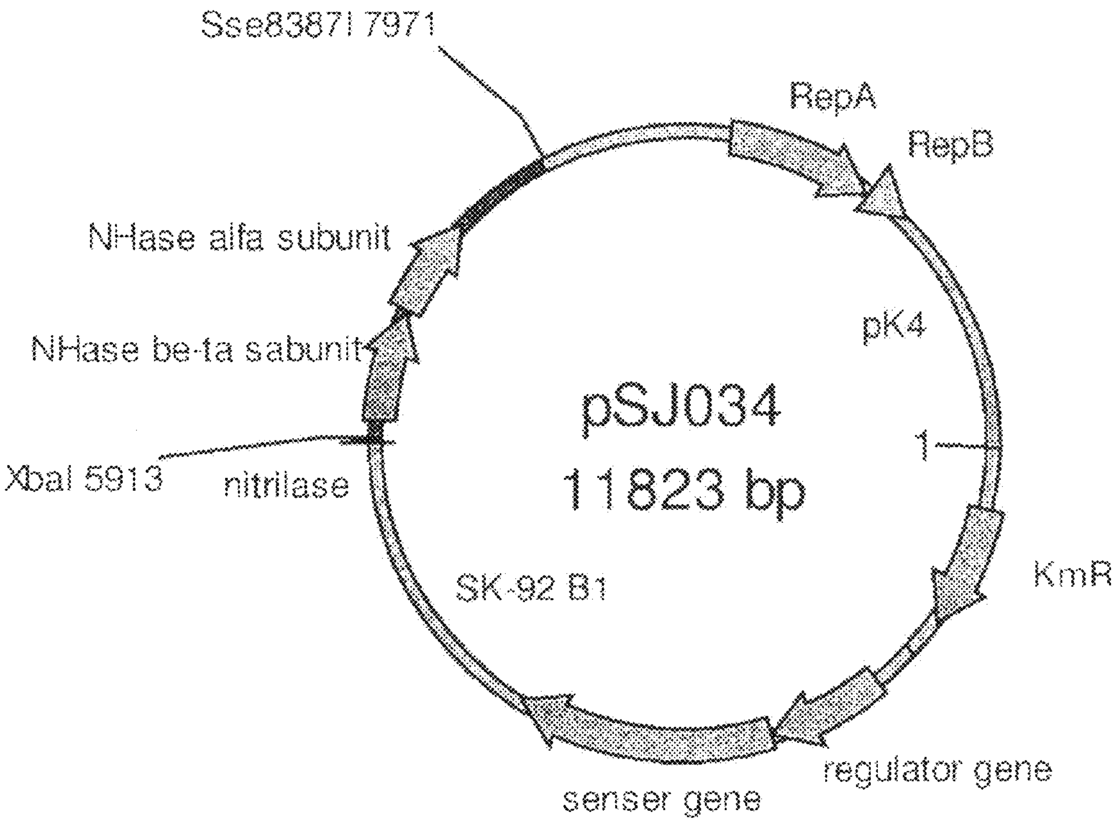
FIG. 1 is a view showing the structure of plasmid pSJ034.

In the following, the present invention is described in detail.

1. Nitrile Hydratase (a) Known Nitrile Hydratase

The improved nitrile hydratase of the present invention is obtained by modifying a known nitrile hydratase and is not limited to being derived from any specific type. For example, those registered as nitrile hydratases in the GenBank database provided by the U.S. National Center for Biotechnology Information (NCBI), or those described as nitrile hydratases in publications, may be referred to for a use. Examples of such nitrile hydratases are those described in patent publications 5~9 (which are incorporated by reference in the present application). Nitrile hydratases in patent publications 5~9 have heat resistance and acrylamide resistance, and by employing amino-acid substitutions according to the present invention, enhanced catalytic activity is further added to their properties. In particular, nitrile hydratases having amino-acid sequences shown in SEQ ID NOs: 53~57 are listed as reference.

Furthermore, by introducing a mutation from the gene encoding the amino-acid sequences described above using a well-known method, and by evaluating and screening mutant enzymes which have desired properties, improved enzymes with further enhanced activity are achieved. In particular, nitrile hydratases with amino-acid sequences shown in SEQ ID NOs: 58~61 are listed.

A "nitrile hydratase" has a conformation formed with α and β subunit domains, and contains a non-heme iron atom or a non-corrin cobalt atom as a prosthetic molecule. Such a nitrile hydratase is identified and referred to as an iron-containing nitrile hydratase or a cobalt-containing nitrile hydratase.

An example of an iron-containing nitrile hydratase is such derived from *Rhodococcus* N-771 strain. The tertiary structure of such an iron-containing nitrile hydratase has been identified by X-ray crystal structural analysis. The enzyme is bonded with non-heme iron via four amino-acid residues in a cysteine cluster (Cys-Ser-Leu-Cys-Ser-Cys) (SEQ ID NO: 48) forming the active site of the α subunit.

As for a cobalt-containing nitrile hydratase, examples are those derived from *Rhodococcus rhodochrous* J1 strain (hereinafter may be referred to as "J1 strain") or derived from *Pseudonocardia thermophila.*

A cobalt-containing nitrile hydratase derived from the J1 strain is bound with a cobalt atom via a site identified as a cysteine cluster (Cys-Thr-Leu-Cys-Ser-Cys) (SEQ ID NO: 49) that forms the active site of the α subunit. In the cysteine cluster of a cobalt-containing nitrile hydratase derived from *Pseudonocardia thermophila*, cysteine (Cys) at position 4 from the upstream side (N-terminal side) of the cysteine cluster derived from the J1 strain is cysteine sulfinic acid (Csi), and cysteine (Cys) at position 6 from the furthermost downstream side (C-terminal side) of the cysteine cluster derived from the J1 strain is cysteine sulfenic acid (Cse).

As described above, a prosthetic molecule is bonded with a site identified as cysteine clusters "C(S/T)LCSC" (SEQ ID NO: 48, 49) in the α subunit. Examples of a nitrile hydratase containing a binding site with such a prosthetic molecule are those that have amino-acid sequences and are encoded by gene sequences derived from the following: *Rhodococcus rhodochrous* J1 (FERM BP-1478), *Rhodococcus rhodochrous* M8 (SU 1731814), *Rhodococcus rhodochrous* M33 (VKM Ac-1515D), *Rhodococcus rhodochrous* ATCC 39484 (JP 2001-292772), *Bacillus smithii* (JP H9-248188), *Pseudonocardia thermophila* (JP H9-275978), or *Geobacillus thermoglucosidasius.*

On the other hand, the β-subunit is thought to be attributed to structural stability.

For example, in the α subunit derived from *Rhodococcus rhodochrous* J1 strain (FERM BP-1478), its amino-acid sequence is shown as SEQ ID NO: 4, and its base sequence is shown as SEQ ID NO: 3. Also, in the β subunit, its amino-acid sequence is shown as SEQ ID NO: 2, its base sequence is shown as SEQ ID NO: 1 and its accession number is "P21220." In addition, in *Rhodococcus rhodochrous* M8 (SU 1731814), the accession number of the α subunit is "ATT 79340" and the accession number of the β subunit is "AAT 79339."

The accession number of the nitrile hydratase gene derived from *Rhodococcus pyridinivorans* MW3 is "AJ582605," and the accession number of the nitrile hydratase gene derived from *Rhodococcus pyridinivorans* S85-2 is "AJ582605." The nitrile hydratase gene of *Rhodococcus ruber* RH (CGMCC No. 2380) is described in CN 101463358. Moreover, the accession number of the nitrile hydratase gene derived from *Nocardia* YS-2002 is "X86737," and the accession number of the nitrile hydratase gene derived from *Nocardia* sp. JBRs is "AY141130."

(b-1) Improved Nitrile Hydratase 0348)

Figures 1, 2:
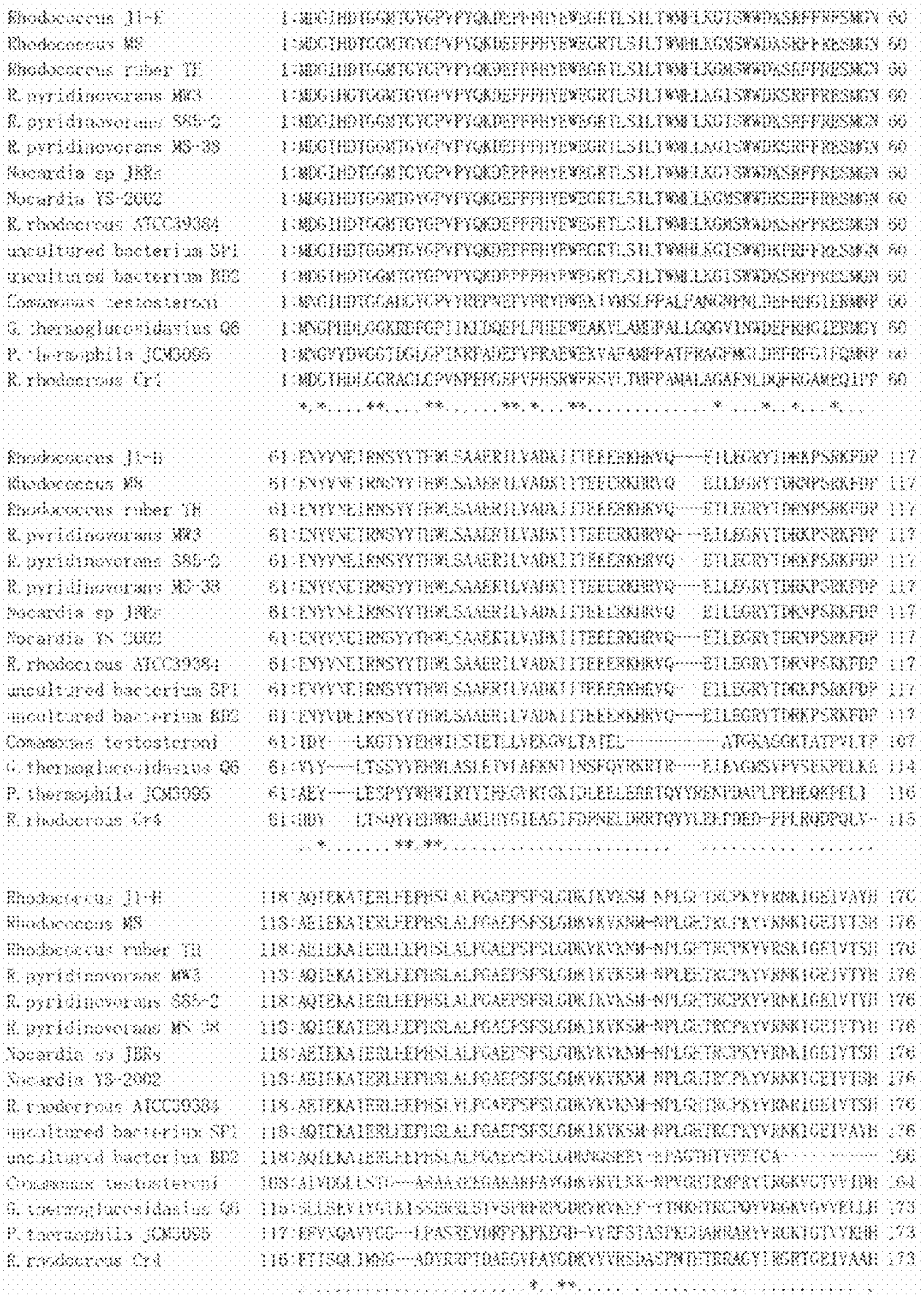

FIGS. 2-1 and 2-2 show the alignments of amino-acid sequences (in one-letter code) in β-subunits of known nitrile hydratases derived from various microorganisms. FIGS. 2-1 and 2-2 each show amino-acid sequences in sequence ID numbers 2, 5~12, and 42~47 of amino-acid sequences from the top.

Furthermore, the improved nitrile hydratase of the present invention includes examples in which one or more (for example, 1~10, preferred to be approximately 1~5) amino-acid residues are deleted, substituted and/or added in the amino-acid sequences of known nitrile hydratases, excluding the amino-acid sequence identified as SEQ ID NO: 50.

An example of the improved nitrile hydratase of the present invention has an amino-acid sequence identified as SEQ ID NO: 51 in the β subunit as shown in FIG. 3. Here, the amino-acid sequence shown as SEQ ID NO: 50 is located at positions 44~52 counted from the N-terminal.

According to an embodiment of the example above, in the improved nitrile hydratase that has the amino-acid sequence as shown in SEQ ID NO: 51, $X_1$, $X_2$, $X_3$, $X_5$, and $X_6$ each independently indicate any amino-acid residue, and $X_4$ is an amino acid selected from among cysteine, aspartic acid, glutamic acid, histidine, isoleucine, lysine, methionine, asparagine, proline, glutamine, serine and threonine.

In addition, according to another embodiment, in the improved nitrile hydratase that has the amino-acid sequence as shown in SEQ ID NO: 51, $X_1$, $X_3$, $X_5$, and $X_6$ each independently indicate any amino-acid residue, $X_2$ is S (serine), and $X_4$ is an amino acid selected from among cysteine, aspartic acid, glutamic acid, histidine, isoleucine, lysine, methionine, asparagine, proline, glutamine, serine and threonine.

Moreover, according to yet another embodiment, in the improved nitrile hydratase that has the amino-acid sequence as shown in SEQ ID NO: 51, $X_1$ is I (isoleucine), $X_2$ is S (serine), $X_3$ is W (tryptophan), and $X_5$ is K (lysine), $X_6$ is S (serine), and $X_4$ is an amino acid selected from among cysteine, aspartic acid, glutamic acid, histidine, isoleucine, lysine, methionine, asparagine, proline, glutamine, serine and threonine.

Another example of the improved nitrile hydratase of the present invention is as follows: in the amino-acid sequence of a known nitrile hydratase identified as SEQ ID NO: 2, the amino-acid residue (tryptophan) at position 48 of the β subunit is substituted with cysteine, aspartic acid, glutamic acid, histidine, isoleucine, lysine, methionine, asparagine, proline, glutamine, serine or threonine.

Modes of such amino-acid substitutions are denoted, for example, as Wβ48C, Wβ48D, Wβ48E, Wβ48H, Wβ48I, Wβ48K, Wβ48M, Wβ48N, Wβ48P, Wβ48Q, Wβ48S or Wβ48T. Amino acids are identified by a single-letter alphabetic code. The letter to the left of the numeral showing the number of amino-acid residues counted from the terminal to the substituted position (for example, "48") represents the amino acid in a one-letter code before substitution, and the letter to the right represents the amino acid in a one-letter code after substitution.

In particular, when the amino-acid sequence of the β subunit as shown in SEQ ID NO: 2 is denoted as "Wβ48C" in the improved nitrile hydratase, the abbreviation means that, in the amino-acid sequence of the β subunit (SEQ ID NO: 2), tryptophan (W) at position 48 counted from the N-terminal amino-acid residue (including the N-terminal amino-acid residue itself) is substituted with cysteine (C).

Modes of amino acid substitutions in more preferred embodiments of the improved nitrile hydratase according to the present invention are shown as the following 1~12:

1. Wβ48C,
2. Wβ48D,
3. Wβ48E,
4. Wβ48H,
5. Wβ48I,
6. Wβ48K,
7. Wβ48M,
8. Wβ48N,
9. Wβ48P,
10. Wβ48Q,
11. Wβ48S, and
12. Wβ48T.

Preferred embodiments of base substitutions to cause the above amino-acid substitutions are shown below.

Wβ48C: a base sequence TGG (at positions 142~144 in SEQ ID NO: 1) is preferred to be substituted with TGC (TGG→TGC).

Wβ48D: a base sequence TGG (at positions 142~144 in SEQ ID NO: 1) is preferred to be substituted with GAC (TGG→GAC).

Wβ48E: a base sequence TGG (at positions 142~144 in SEQ ID NO: 1) is preferred to be substituted with GAG (TGG→GAG).

Wβ48F: a base sequence TGG (at positions 142~144 in SEQ ID NO: 1) is preferred to be substituted with TTC (TGG→TTC).

Wβ48H: a base sequence TGG (at positions 142~144 in SEQ ID NO: 1) is preferred to be substituted with CAC (TGG→CAC).

Wβ48I: a base sequence TGG (at positions 142~144 in SEQ ID NO: 1) is preferred to be substituted with ATC (TGG→ATC).

Wβ48K: a base sequence TGG (at positions 142~144 in SEQ ID NO: 1) is preferred to be substituted with AAG (TGG→AAG).

Wβ48M: a base sequence TGG (at positions 142~144 in SEQ ID NO: 1) is preferred to be substituted with ATG (TGG→ATG).

Wβ48N: a base sequence TGG (at positions 142~144 in SEQ ID NO: 1) is preferred to be substituted with AAC (TGG→AAC).

Wβ48P: a base sequence TGG (at positions 142~144 in SEQ ID NO: 1) is preferred to be substituted with CCG (TGG→CCG).

Wβ48Q: a base sequence TGG (at positions 142~144 in SEQ ID NO: 1) is preferred to be substituted with CAG (TGG→CAG).

Wβ48S: a base sequence TGG (at positions 142~144 in SEQ ID NO: 1) is preferred to be substituted with TCC (TGG→TCC).

Wβ48T: a base sequence TGG (at positions 142~144 in SEQ ID NO: 1) is preferred to be substituted with ACC (TGG→ACC).

(b-2) Improved Nitrile Hydratase (β37)

FIGS. 6-1 and 6-2 show the alignments of amino-acid sequences (in the one-letter code) in β-subunits of known nitrile hydratases derived from various microorganisms. FIGS. 6-1 and 6-2 each show amino-acid sequences in sequence ID numbers 2, 5~12, and 42~49 of amino-acid sequences from the top.

Furthermore, the improved nitrile hydratase of the present invention includes examples in which one or more (for example, 1~10, preferred to be approximately 1~5) amino-acid residues are deleted, substituted and/or added in the amino-acid sequences of known nitrile hydratases, excluding the amino-acid sequence identified as SEQ ID NO: 81.

An example of the improved nitrile hydratase of the present invention has an amino-acid sequence identified as SEQ ID NO: 82 in the β subunit as shown in FIG. 7. Here, the amino-acid sequence shown in SEQ ID NO: 81 is located at positions 29~49 counted from the N-terminal.

According to an embodiment, in the improved nitrile hydratase that has the amino-acid sequence shown in SEQ ID NO: 82, $X_1$~$X_6$ and $X_8$~$X_{18}$ each independently indicate any amino-acid residue, and $X_7$ is an amino acid selected from among alanine, aspartic acid, threonine, phenylalanine, isoleucine and methionine.

According to another embodiment, in the improved nitrile hydratase that has the amino-acid sequence shown in SEQ ID NO: 82, $X_1$~$X_6$, $X_8$~$X_{13}$ and $X_{15}$~$X_{18}$, each independently indicate any amino-acid residue, $X_4$ is G (glycine), and $X_7$ is an amino acid selected from among alanine, valine, aspartic acid, threonine, phenylalanine, isoleucine and methionine.

According to yet another embodiment, in the improved nitrile hydratase that has the amino-acid sequence as shown in SEQ ID NO: 82, $X_{15}$~$X_{18}$ each independently indicate any amino-acid residue, $X_1$ is G (glycine), $X_2$ is R (arginine), $X_3$ is T (threonine), $X_4$ is L (leucine), $X_5$ is S (serine), $X_6$ is I (isoleucine), $X_8$ is T (threonine), $X_9$ is W (tryptophan), $X_{10}$ is M (methionine), $X_{11}$ is H (histidine), $X_{12}$ is L (leucine), $X_{13}$ is K (lysine), $X_{14}$ is G (glycine), $X_7$ is an amino acid selected from among alanine, valine, aspartic acid, threonine, phenylalanine, isoleucine and methionine.

Another example of the improved nitrile hydratase of the present invention is as follows: in the amino-acid sequence of a known nitrile hydratase identified as SEQ ID NO: 2, the amino-acid residue (leucine) at position 37 of the β subunit is substituted with alanine, valine, aspartic acid, threonine, phenylalanine, isoleucine or methionine.

Modes of such amino-acid substitutions are denoted, for example, as Lβ37A, Lβ37D, Lβ37F, Lβ37I, Lβ37M, Lβ37T or Lβ37V. Amino acids are identified by a single-letter alphabetic code. The letter to the left of the numeral showing the number of amino-acid residues counted from the terminal to the substituted position (for example, "37") is the amino acid in the one-letter code before substitution, and the letter to the right represents the amino acid in the one-letter code after substitution.

In particular, when the amino-acid sequence of the β subunit (SEQ ID NO: 2) identified as SEQ ID NO: 2 is denoted as "Lβ37A" in the improved nitrile hydratase, the abbreviation means that, in the amino-acid sequence of the β subunit (SEQ ID NO: 2), leucine (L) at position 37 counted from the N-terminal amino-acid residue (including the N-terminal amino-acid residue itself) is substituted with alanine (A).

Modes of amino acid substitutions in more preferred embodiments of the improved nitrile hydratase according to the present invention are shown as the following 1~7:

1. Lβ37A,
2. Lβ37D,
3. Lβ37F,
4. Lβ37I,
5. Lβ37M,
6. Lβ37T and
7. Lβ37V.

Preferred embodiments of base substitutions to cause the above amino-acid substitutions are shown in Table 1 below.

TABLE 1

| amino-acid substitution | base substitution |
|---|---|
| Lβ37A | Base sequence CTG (positions at 109~111 in SEQ ID NO: 1) is preferred to be substituted with GCA, GCC, GCG or GCT. Especially preferred to be substituted is C at position 109 with G, T at position 110 with C, and G at position 111 with C (CTG→GCC). |
| Lβ37D | Base sequence CTG (positions at 109~111 in SEQ ID NO: 1) is preferred to be substituted with GAC or GAT. Especially preferred to be substituted is C at position 109 with G, T at position 110 with A, and G at position 111 with C (CTG→GAC). |
| Lβ37F | Base sequence CTG (positions at 109~111 in SEQ ID NO: 1) is preferred to be substituted with TTC or TTT. Especially preferred to be substituted is C at position 109 with T and G at position 111 with C (CTG→TTC). |
| Lβ37I | Base sequence CTG (positions at 109~111 in SEQ ID NO: 1) is preferred to be substituted with ATT, ATC or ATA. Especially preferred to be substituted is C at position 109 with A and G at position 111 with C (CTG→ATC). |
| Lβ37M | Base sequence CTG (positions at 109~111 in SEQ ID NO: 1) is preferred to be substituted with ATG. Especially preferred to be substituted is C at position 109 with A (CTG→ATG). |
| Lβ37T | Base sequence CTG (positions at 109~111 in SEQ ID NO: 1) is preferred to be substituted with ACA, ACC, ACG or ACT. Especially preferred to be substituted is C at position 109 with A, T at position 110 with C and G at position 111 with C (CTG→ACC). |
| Lβ37V | Base sequence CTG (positions at 109~111 in SEQ ID NO: 1) is preferred to be substituted with GTA, GTC, GTG or GTT. Especially preferred to be substituted is C at position 109 with G and G at position 111 with C (CTG→GTC). |

(b-3) Improved Nitrile Hydratase (α83)

FIGS. 8-1 and 8-2 show amino-acid sequence alignments (in one-letter code) in α-subunits of known nitrile hydratases derived from various microorganisms. FIGS. 8-1 and 8-2 each show amino-acid sequences in sequence ID numbers 4, 105~108, 121, 109, 110, 112, 111, 122~124, 113, 114, 125 from the top.

Furthermore, the improved nitrile hydratase of the present invention includes examples in which one or more (for example, 1~10, preferred to be approximately 1~5) amino-acid residues are deleted, substituted and/or added in amino-acid sequences of known nitrile hydratases, excluding the amino-acid sequence identified as SEQ ID NO: 119. Examples of such a nitrile hydratase are described in patent publications 5~9 (the contents are incorporated by reference into the present application). Nitrile hydratases in patent publication 5~9 each exhibit heat resistance and acrylamide resistance. Moreover, as a result of amino-acid substitutions of the present invention, enhanced catalytic activity is further added to their properties.

An example of the improved nitrile hydratase of the present invention has an amino-acid sequence as shown in SEQ ID NO: 120 in the α subunit as shown in FIG. 9. Here, an amino-acid sequence shown in SEQ ID NO: 119 is located at positions 73~83 counted from the N-terminal.

According to an embodiment, in the improved nitrile hydratase that has the amino-acid sequence shown in SEQ ID NO: 120, $X_1$~$X_7$ each independently indicate any amino-acid residue, and $X_8$ is an amino acid selected from among alanine, leucine, methionine, asparagine, cysteine, aspartic acid, glutamic acid, phenylalanine, glycine, histidine, lysine, proline, arginine, serine, threonine, tyrosine and tryptophan.

According to another embodiment, in the improved nitrile hydratase that has the amino-acid sequence shown in SEQ ID NO: 120, $X_1$ is M (methionine), $X_7$ is A (alanine), $X_3$ is S (serine), $X_4$ is L (leucine), $X_5$ is Y (tyrosine), $X_6$ is A (alanine), $X_7$ is E (glutamic acid), and $X_8$ is an amino acid selected from among alanine, leucine, methionine, asparagine, cysteine, aspartic acid, glutamic acid, phenylalanine, glycine, histidine, lysine, proline, arginine, serine, threonine, tyrosine and tryptophan.

Another example of the improved nitrile hydratase of the present invention is as follows: in the amino-acid sequence of a known nitrile hydratase identified as SEQ ID NO: 4, the amino-acid residue at position 83 (glutamine) of the α subunit is substituted with alanine, leucine, methionine, asparagine, cysteine, aspartic acid, glutamic acid, phenylalanine, glycine, histidine, lysine, proline, arginine, serine, threonine, tyrosine or tryptophan.

Modes of such amino-acid substitutions are denoted, for example, as Qα83A, Qα83C, Qα83D, Qα83E, Qα83F, Qα83G, Qα83H, Qα83K, Qα83L, Qα83M, Qα83N, Qα83P, Qα83R, Qα83S, Qα83T, Qα83Y and Qα83W. Amino acids are identified by a single-letter alphabetic code. The letter to the left of the numeral showing the number of amino-acid residues counted from the terminal to the substituted position (for example, "83") represents the amino acid in a one-letter code before substitution, and the letter to the right represents the amino acid in a one-letter code after substitution.

In particular, when the amino-acid sequence of the α subunit in SEQ ID NO: 4 is denoted as "Qα83A" in the improved nitrile hydratase, the abbreviated notation means that, in the amino-acid sequence of the α subunit (SEQ ID NO: 4), glutamine (Q) at position 83 counted from the N-terminal amino-acid residue (including the N-terminal amino-acid residue itself) is substituted with alanine (A).

Modes of amino-acid substitutions in more preferred embodiments of the improved nitrile hydratase according to the present invention are shown as the following 1~17:

1. Qα83A,
2. Qα83C,
3. Qα83D,
4. Qα83E,
5. Qα83F,
6. Qα83G,
7. Qα83H,
8. Qα83K,
9. Qα83L,
10. Qα83M,
11. Qα83N,
12. Qα83P,
13. Qα83R,
14. Qα83S,
15. Qα83T,
16. Qα83Y and
17. Qα83W.

Preferred embodiments of base substitutions to cause the above amino-acid substitutions are shown below.

TABLE 2

| amino-acid substitution | base substitution |
|---|---|
| Qα83A | Base sequence CAG (positions at 247~249 in SEQ ID NO: 3) is preferred to be substituted with GCA, GCC, CCG, or GCT. Especially preferred to be substituted is C at position 247 with G, A at position 248 with C, and G at position 249 with C (CAG→GCC). |
| Qα83C | Base sequence CAG (positions at 247~249 in SEQ ID NO: 3) is preferred to be substituted with TGC or TGT. Especially preferred to be substituted is C at position 247 with T, A at position 248 with G, and G at position 249 with C (CAG→TGC). |
| Qα83D | Base sequence CAG (positions at 247~249 in SEQ ID NO: 3) is preferred to be substituted with CAC or GAT. Especially preferred to be substituted is C at position 247 with G, and G at position 249 with C (CAG→GAC). |
| Qα83E | Base sequence CAG (positions at 247~249 in SEQ ID NO: 3) is preferred to be substituted with GAG or GAA. Especially preferred to be substituted is C at position 247 with G (CAG→GAG). |
| Qα83F | Base sequence CAG (positions at 247~249 in SEQ ID NO: 3) is preferred to be substituted with TTC or TTT. Especially preferred to be substituted is C at position 247 with T, A at position 248 with T, and G at position 249 with C (CAG→TTC). |
| Qα83G | Base sequence CAG (positions at 247~249 in SEQ ID NO: 3) is preferred to be substituted with GGA, GGC, GGG or GGT. Especially preferred to be substituted is C at position 247 with G, A at position 248 with G, and G at position 249 with C (CAG→GGC). |
| Qα83H | Base sequence CAG (positions at 247~249 in SEQ ID NO: 3) is preferred to be substituted with CAC or CAT. Especially preferred to be substituted is G at position 249 with C (CAG→CAC). |
| Qα83K | Base sequence CAG (positions at 247~249 in SEQ ID NO: 3) is preferred to be substituted with AAA or AAG. Especially preferred to be substituted is C at position 247 with A (CAG→AAG). |
| Qα83L | Base sequence CAG (positions at 247~249 in SEQ ID NO: 3) is preferred to be substituted with CTA, CTC, CTG, CTT, TTA or TTG. Especially preferred to be substituted is A at position 248 with T, and G at position 249 with C (CAG→CTC). |
| Qα83M | Base sequence CAG (positions at 247~249 in SEQ ID NO: 3) is preferred to be substituted with ATG. Especially preferred to be substituted is C at position 247 with A, and A at position 248 with T (CAG→ATG). |
| Qα83N | Base sequence CAG (positions at 247~249 in SEQ ID NO: 3) is preferred to be substituted with AAC or AAT. Especially preferred to be substituted is C at position 247 with A, and G at position 249 with C (CAG→AAC). |
| Qα83P | Base sequence CAG (positions at 247~249 in SEQ ID NO: 3) is preferred to be substituted with CCA, CCC, CCG or CCT. Especially preferred to be substituted is A at position 248 with C (CAG→CCG). |
| Qα83R | Base sequence CAG (positions at 247~249 in SEQ ID NO: 3) is preferred to be substituted with CGA, CGC, CGG, CGT, AGA or AGG. Especially preferred to be substituted is A at position 248 with G (CAG→CGG). |

TABLE 2-continued

| amino-acid substitution | base substitution |
|---|---|
| Qα83S | Base sequence CAG (positions at 247~249 in SEQ ID NO: 3) is preferred to be substituted with TCA, TCC, TCG, TCT, AGC or ACT. Especially preferred to be substituted is C at position 247 with T, A at position 248 with C, and G at position 249 with C (CAG→TCC). |
| Qα83T | Base sequence CAG (positions at 247~249 in SEQ ID NO: 3) is preferred to be substituted with ACA, ACC, ACG or ACT. Especially preferred to be substituted is C at position 247 with A, A at position 248 with C, and G at position 249 with C (CAG→ACC). |
| Qα83Y | Base sequence CAG (positions at 247~249 in SEQ ID NO: 3) is preferred to be substituted with TAC or TAT. Especially preferred to be substituted is C at position 247 with T, and G at position 249 with C (CAG→TAC). |
| Qα83W | Base sequence CAG (positions at 247~249 in SEQ ID NO: 3) is preferred to be substituted with TGG. Especially preferred to be substituted is C at position 247 with T, and A at position 248 with G (CAG→TGG). |

(b-4) Improved Nitrile Hydratase (α82)

FIGS. 10-1 and 10-2 show amino-acid sequence alignments (in the one-letter code) in α-subunits of known nitrile hydratases derived from various microorganisms. FIGS. 10-1 and 10-2 each show amino-acid sequences in sequence ID numbers 4, 105~108, 121, 109, 110, 112, 111, 122~124, 113, 114, 125 from the top.

Furthermore, the improved nitrile hydratase of the present invention includes examples in which one or more (for example, 1~10, preferred to be approximately 1~5) amino-acid residues are deleted, substituted and/or added in the amino-acid sequences of known nitrile hydratases, excluding the amino-acid sequence identified as SEQ ID NO: 131. Examples of the improved nitrile hydratase are described in patent publications 5~9 (the contents are incorporated by reference into the present application). Nitrile hydratases in patent publication 5~9 each exhibit heat resistance and acrylamide resistance. Moreover, as a result of amino-acid substitutions of the present invention, enhanced catalytic activity is further added to their properties.

An example of the improved nitrile hydratase of the present invention has an amino-acid sequence as shown in SEQ ID NO: 131 in the α subunit as shown in FIG. 11. Here, an amino-acid sequence shown in SEQ ID NO: 132 is located at positions 73~83 counted from the N-terminal.

According to an embodiment of the present invention, in the improved nitrile hydratase that has the amino-acid sequence shown in SEQ ID NO: 131, $X_1$~$X_6$ each independently indicate any amino-acid residue, and $X_7$ is an amino acid selected from among cysteine, phenylalanine, histidine, isoleucine, lysine, methionine, glutamine, arginine, threonine and tyrosine.

According to another embodiment, in the improved nitrile hydratase that has the amino-acid sequence shown in SEQ ID NO: 131, $X_1$ is M (methionine), $X_2$ is A (alanine), $X_3$ is S (serine), $X_4$ is L (leucine), $X_5$ is Y (tyrosine), $X_6$ is A (alanine), and $X_7$ is an amino acid selected from among cysteine, phenylalanine, histidine, isoleucine, lysine, methionine, glutamine, arginine, threonine and tyrosine.

Another example of the improved nitrile hydratase of the present invention is as follows: in the amino-acid sequence of a known nitrile hydratase shown in SEQ ID NO: 4, the amino-acid residue at position 82 (glutamic acid) of the α subunit is substituted with cysteine, phenylalanine, histidine, isoleucine, lysine, methionine, glutamine, arginine, threonine or tyrosine.

Modes of such amino-acid substitutions are denoted, for example, as Eα82C, Eα82F, Eα82H, Eα82I, Eα82K, Eα82M, Eα82Q, Eα82R, Eα82T and Eα82Y. Amino acids are identified by a single-letter alphabetic code. The letter to the left of the numeral showing the number of amino-acid residues counted from the terminal to the substituted position (for example, "82") is the amino acid in a one-letter code before substitution, and the letter to the right represents the amino acid in a one-letter code after substitution.

In particular, when the amino-acid sequence of the α subunit in SEQ ID NO: 4 is denoted as "Eα82C" in the improved nitrile hydratase, the abbreviated notation means among the amino-acid sequence of the α subunit, glutamic acid (E) at position 82 counted from the N-terminal amino-acid residue (including the N-terminal amino-acid residue itself) is substituted with cysteine (C).

Modes of amino acid substitutions in more preferred embodiments of the improved nitrile hydratase according to the present invention are shown as the following 1~10:

1. Eα82C,
2. Eα82F,
3. Eα82H,
4. Eα82I,
5. Eα82K,
6. Eα82M,
7. Eα82Q,
8. Eα82R,
9. Eα82T and
10. Eα82Y.

Preferred embodiments of base substitutions to cause above amino-acid substitutions are shown below.

TABLE 3

| amino-acid substitution | base substitution |
|---|---|
| Eα82C | Base sequence GAG (positions at 244~246 in SEQ ID NO: 3) is preferred to be substituted with TGC or TGT. Especially preferred to be substituted is G at position 244 with T, A at position 245 with G, and G at position 246 with C (GAG→TGC). |
| Eα82F | Base sequence GAG (positions at 244~246 in SEQ ID NO: 3) is preferred to be substituted with TTC or TTT. Especially preferred to be substituted is G at position 244 with T, A at position 245 with T, and G at position 246 with C (GAG→TTC). |

TABLE 3-continued

| amino-acid substitution | base substitution |
|---|---|
| Eα82H | Base sequence GAG (positions at 244~246 in SEQ ID NO: 3) is preferred to be substituted with CAT or CAC. Especially preferred to be substituted is G at position 244 with C, and G at position 246 with C (GAG→CAC). |
| Eα82I | Base sequence GAG (positions at 244~246 in SEQ ID NO: 3) is preferred to be substituted with ATT, ATC or ATA. Especially preferred to be substituted is G at position 244 with A, A at position 245 with T, and G at position 246 with C (GAG→ATC). |
| Eα82K | Base sequence GAG (positions at 244~246 in SEQ ID NO: 3) is preferred to be substituted with AAA or AAG. Especially preferred to be substituted is G at position 244 with A (GAG→AAG). |
| Eα82M | Base sequence GAG (positions at 244~246 in SEQ ID NO: 3) is preferred to be substituted with ATG. Especially preferred to be substituted is G at position 244 with A, and A at position 245 with T (GAG→ATG). |
| Eα82Q | Base sequence GAG (positions at 244~246 in SEQ ID NO: 3) is preferred to be substituted with CAA or CAG. Especially preferred to be substituted is G at position 244 with C (GAG→CAG). |
| Eα82R | Base sequence GAG (positions at 244~246 in SEQ ID NO: 3) is preferred to be substituted with CGA, CGC, CGG, CGT, AGA or AGG. Especially preferred to be substituted is G at position 244 with C, and A at position 245 with G (GAG→CGG). |
| Eα82T | Base sequence GAG (positions at 244~246 in SEQ ID NO: 3) is preferred to be substituted with ACA, ACC, ACG or ACT. Especially preferred to be substituted is G at position 244 with A, A at position 245 with C, and G at position 246 with C (GAG→ACC). |
| Eα82Y | Base sequence GAG (positions at 244~246 in SEQ ID NO: 3) is preferred to be substituted with TAT or TAC. Especially preferred to be substituted is G at position 244 with T, and G at position 246 with G (GAG→TAC). |

(b-5) Improved Nitrile Hydratase (α85)

FIGS. 12-1 and 12-2 show the alignments of amino-acid sequences (in the one-letter code) in α-subunits of known nitrile hydratases derived from various microorganisms. FIGS. 12-1 and 12-2 each show amino-acid sequences in sequence ID numbers 4, 105~108, 121, 109, 110, 112, 111, 122~124, 113, 114, 125 from the top.

Furthermore, the improved nitrile hydratase of the present invention includes examples in which one or more (for example, 1~10, preferred to be approximately 1~5) amino-acid residues are deleted, substituted and/or added in the amino-acid sequences of known nitrile hydratases, excluding the amino-acid sequence identified as SEQ ID NO: 135. Examples of such a nitrile hydratase are described in patent publications 5~9 (the contents are incorporated by reference into the present application). Nitrile hydratases in patent publication 5~9 each exhibit heat resistance and acrylamide resistance. Moreover, as a result of amino-acid substitutions of the present invention, enhanced catalytic activity is further added to their properties.

An example of the improved nitrile hydratase of the present invention has an amino-acid sequence as shown in SEQ ID NO: 135 in the α subunit as shown in FIG. 13. Here, an amino-acid sequence shown in SEQ ID NO: 136 is located at positions 73~85 counted from the N-terminal.

According to an embodiment of the present invention, in the improved nitrile hydratase that has the amino-acid sequence shown in SEQ ID NO: 135, $X_1$~$X_8$ each independently indicate any amino-acid residue, and $X_9$ is an amino acid selected from among cysteine, glutamic acid, phenylalanine, isoleucine, asparagine, glutamine, serine and tyrosine.

According to another embodiment, in the improved nitrile hydratase that has the amino-acid sequence shown in SEQ ID NO: 135, $X_1$ is M (methionine), $X_2$ is A (alanine), $X_3$ is S (serine), $X_4$ is L (leucine), $X_5$ is Y (tyrosine), $X_6$ is A (alanine), $X_7$ is E (glutamic acid), $X_8$ is A (alanine), and $X_9$ is an amino acid selected from among cysteine, glutamic acid, phenylalanine, isoleucine, asparagine, glutamine, serine and tyrosine.

Another example of the improved nitrile hydratase of the present invention is as follows: in the amino-acid sequence of a known nitrile hydratase shown in SEQ ID NO: 4, the amino-acid residue at position 85 (histidine) of the α subunit is substituted with cysteine, glutamic acid, phenylalanine, isoleucine, asparagine, glutamine, serine or tyrosine.

Modes of such amino-acid substitutions are shown, for example, as Hα85C, Hα85E, Hα85F, Hα85I, Hα85N, Hα85Q, Hα85S and Hα85Y. Amino acids are identified by a single-letter alphabetic code. The letter to the left of the numeral showing the number of amino-acid residues counted from the terminal to the substituted position (for example, "85") is the amino acid in a one-letter code before substitution, and the letter to the right represents the amino acid in a one-letter code after substitution.

In particular, when the amino-acid sequence of the α subunit in SEQ ID NO: 4 is denoted as "Hα85C" in the improved nitrile hydratase, the abbreviated notation means that, in the amino-acid sequence of the α subunit (SEQ ID NO: 4), histidine (H) at position 85 counted from the N-terminal amino-acid residue (including the N-terminal amino-acid residue itself) is substituted with cysteine (C).

Modes of amino acid substitutions in more preferred embodiments of the improved nitrile hydratase according to the present invention are shown as the following 1~8:

1. Hα85C,
2. Hα85E,
3. Hα85F,
4. Hα85I,
5. Hα85N,
6. Hα85Q,
7. Hα85S and
8. Hα85Y.

Preferred embodiments of base substitutions to cause the above amino-acid substitutions are shown below.

TABLE 4

| amino-acid substitution | base substitution |
|---|---|
| Hα85C | Base sequence CAC (positions at 253~255 in SEQ ID NO: 3) is preferred to be substituted with TGC or TGT. Especially preferred to be substituted is C at position 253 with T, and A at position 254 with G (CAC→TGC). |
| Hα85E | Base sequence CAC (positions at 253~255 in SEQ ID NO: 3) is preferred to be substituted with GAG or GAA. Especially preferred to be substituted is C at position 253 with G, and C at position 255 with G (CAC→GAG). |
| Hα85F | Base sequence CAC (positions at 253~255 in SEQ ID NO: 3) is preferred to be substituted with TTC or TTT. Especially preferred to be substituted is C at position 253 with T, and A at position 254 with T (CAC→TTC). |
| Hα85I | Base sequence CAC (positions at 253~255 in SEQ ID NO: 3) is preferred to be substituted with ATT, ATC or ATA. Especially preferred to be substituted is C at position 253 with A, and A at position 254 with T (CAC→ATC). |
| Hα85N | Base sequence CAC (positions at 253~255 in SEQ ID NO: 3) is preferred to be substituted with AAC or AAT. Especially preferred to be substituted is C at position 253 with A (CAC→AAC). |
| Hα85Q | Base sequence CAC (positions at 253~255 in SEQ ID NO: 3) is preferred to be substituted with CAA or CAG. Especially preferred to be substituted is C at position 255 with G (CAC→CAG). |
| Hα85S | Base sequence CAC (positions at 253~255 in SEQ ID NO: 3) is preferred to be substituted with TCA, TCC, TCG, TCT, AGC or AGT. Especially preferred to be substituted is C at position 253 with T, and A at position 254 with C (CAC→TCC). |
| Hα85Y | Base sequence CAC (positions at 253~255 in SEQ ID NO: 3) is preferred to be substituted with TAT or TAC. Especially preferred to be substituted is C at position 253 with T (CAC→TAC). |

(b-6) Nitrile Hydratase Activity

Among the activity properties of the improved nitrile hydratase according to the present invention, catalytic activity is improved relative to that in a nitrile hydratase before a mutation is introduced.

Here, "nitrile hydratase activity" means an enzyme to catalyze the hydration for converting a nitrile compound to a corresponding amide compound ($RCN+H_2O \rightarrow RCONH_2$). Determining the activity is conducted by bringing a nitrile compound as a substrate into contact with a nitrile hydratase for conversion to a corresponding amide compound and by determining the resultant amide compound. Any nitrile compound may be used as a substrate as long as nitrile hydratase reacts with such a compound, but acrylonitrile is preferred.

Reaction conditions are a substrate concentration of 2.5%, reaction temperature of 10° C. to 30° C. and duration of 10~30 minutes. The enzymatic reactions are terminated by adding phosphoric acid. Then, using HPLC (high-performance liquid chromatography) or gas chromatography, the produced acrylamide is analyzed to measure the amount of the amide compound.

"Improved catalytic activity" means that when activity is measured in the culture of a transformant containing the improved nitrile hydratase or the improved nitrile hydratase isolated from the transformant, the catalytic activity of the improved nitrile hydratase is at least 10% higher than that of the parent strain measured under the same conditions. The parent strain in the present application means a transformant into which a template plasmid for mutation was introduced.

As for an amide compound, an amide compound represented by the general formula (1) below, for example, is preferred.

$$R\text{—}CONH_2 \quad (1)$$

(Here, R is an optionally substituted linear or branched alkyl or alkenyl group having 1~10 carbon atoms, an optionally substituted cycloalkyl or allyl group having 3~48 carbon atoms, or an optionally substituted saturated or unsaturated heterocyclic group.) Especially preferred is an acrylamide in which "R" in the formula is "$CH_2{=}CH$—."

The above improved nitrile hydratase is obtained by performing amino-acid substitution on a nitrile hydratase. For example, such an improved nitrile hydratase is obtained by modifying the amino-acid sequence (SEQ ID NO: 2) of a nitrile hydratase derived from *Rhodococcus rhodochrous* J1 strain, and by screening a nitrile hydratase with an improved catalytic activity.

*Rhodococcus rhodochrous* J1 strain is internationally registered under accession number "FERM BP-1478" at the International Patent Organism Depositary, National Institute of Advanced Industrial Science and Technology (Central 6, 1-1-1 Higashi, Tsukuba, Ibaraki), deposited Sep. 18, 1987.

Using a nitrile hydratase derived from bacteria other than the J1 strain, catalytic activity is thought to be improved as well when a mutation is introduced by modifying a position, type of amino acid or DNA sequence described above. Preferred strains are: *Rhodococcus rhodochrous* M8 (SU 1731814) (SEQ ID NO: 5), *Rhodococcus ruber* TH (SEQ ID NO: 6), *Rhodococcus rhodochrous* M33 (VKM Ac-1515D), *Rhodococcus pyridinivorans* MW3 (SEQ ID NO: 7), *Rhodococcus pyridinivorans* S85-2 (SEQ ID NO: 8), *Rhodococcus pyridinivorans* MS-38 (SEQ ID NO: 9), *Rhodococcus ruber* RH (CN 101463358) (SEQ ID NO: 52), *Nocardia* sp. JBRs (SEQ ID NO: 10), *Nocardia* sp. YS-2002 (SEQ ID NO: 11), *Rhodococcus rhodochrous* ATCC 39384 (SEQ ID NO: 12), uncultured bacterium SP1 (SEQ ID NO: 42), uncultured bacterium BD2 (SEQ ID NO: 43), Comamonas testosterone (SEQ ID NO: 44), *Geobacillus thermoglucosidasius* Q6 (SEQ ID NO: 45), *Pseudonocardia thermophila* JCM 3095 (SEQ ID NO: 46), *Rhodococcus rhodochrous* Cr 4 (SEQ ID NO: 47), or the like. Obtained through natural mutation from the M8 strain above (SU 1731814), *Rhodococcus rhodochrous* M33 (VKM Ac-1515D) was selected because it is capable of constitutive expression of a nitrile hydratase. The amino-acid or gene sequence of the nitrile hydratase itself is not mutated (U.S. Pat. No. 5,827,699). In the β subunit in a bacterium listed above, the amino-acid residue at position 48 from the N-terminal of the improved nitrile hydratase is substituted with cysteine, aspartic acid, glutamic acid, histidine, isoleucine, lysine, methionine, asparagine, proline, glutamine, serine or threonine.

Methods for conducting amino-acid substitution on a wild-type nitrile hydratase are as follows: a bacterium having nitrile hydratase activity is brought into contact for reactions with chemicals such as hydroxyl amine or nitrous acid as a mutation source; UV rays are irradiated to induce mutation; error-prone PCR or site-directed mutagenesis is employed to introduce a mutation at random into the gene that encodes a nitrile hydratase; and the like.

(b-7) Error-Prone PCR

To study functions and characteristics of proteins using a mutant, random mutagenesis is known. Random mutagenesis is a method to introduce a random mutation to the gene encoding a specific protein so that a mutant is produced. In random mutagenesis by PCR, stringency conditions are set low for the DNA amplification period so that a mutant base is introduced (error-prone PCR).

In such an error-prone PCR method, a mutation is introduced randomly into any position of the entire DNA site to be amplified. Then, by examining the function of the obtained mutant, which occurred through the mutation introduced at a random site, information of the amino acid or domain important for a specific function of a protein is obtained.

As a nitrile hydratase used for the template of error-prone PCR, the nitrile hydratase gene derived from a wild-type strain or DNA obtained as an amplified product by error-prone PCR is used.

As reaction conditions for error-prone PCR, for example, a composition ratio of any one, two or three among dNTP (dGTP, dCTP, dATP or dTTP) in the reaction mix is reduced relative to another dNTP. In so setting, during the DNA synthesis, at a position that requires a dNTP whose ratio is reduced, another dNTP is more likely to be used by error and that may lead to mutation. In addition, other preferred reaction conditions are a composition in which the amount of $MgCl_2$ and/or $MnCl_2$ in the reaction mix is increased.

(b-8) Improved Nitrile Hydratase Mutagenesis

Based on a known nitrile hydratase gene, DNA that encodes such an improved nitrile hydtratase is produced by site-directed mutagenesis methods described in Molecular Cloning, A Laboratory Manual, 2nd edition, Cold Spring Harbor Laboratory Press (1989), Current Protocols in Molecular Biology, John Wiley and Sons (1987-1997) and the like. To introduce a mutation into DNA by well-known methods such as the Kunkel method or Gapped Duplex method, mutagenesis kits applying site-directed mutagenesis methods such as follows are used: QuickChange™ XL Site-Directed Mutagenesis Kit (made by Stratagene), GeneTailor™ Site-Directed Mutagenesis System (made by Invitrogen Corporation), TaKaRa Site-Directed Mutagenesis System (Mutan-K, Mutan-Super Express Km and the like, made by Takara Bio Inc.) and the like.

Furthermore, the DNA related to the present invention includes DNA which is hybridized under stringent conditions with a DNA made up of a base sequence complementary to the base sequence of the DNA of the present invention, and which encodes a protein having nitrile hydratase activity.

Such an improved nitrile hydratase DNA is obtained by introducing a mutation into a wild-type gene as described above. Alternatively, using the DNA sequence or its complementary sequence or a DNA fragment as a probe, improved nitrile hydratase DNA may also be obtained from cDNA libraries and genomic libraries by employing well-known hybridization methods such as colony hybridization, plaque hybridization, Southern blot or the like. Libraries constructed by a well-known method may be used, or commercially available cDNA libraries and genomic libraries may also be used.

"Stringent conditions" are those for washing after hybridization; a salt concentration of 300~2000 mM and a temperature of 40~75° C., preferably a salt concentration of 600~900 mM and a temperature of 65° C. For example, conditions 2×SSC at 50° C. may be employed. In addition to such a salt concentration of the buffer, temperature and the like, a person skilled in the art may set conditions for obtaining DNA that encodes a nitrile hydratase of the present invention by adding various conditions such as probe concentration, probe length and reaction time.

For detailed procedures for hybridization, *Molecular Cloning, A Laboratory Manual, 2nd edition* (Cold Spring Harbor Laboratory Press (1989)) or the like may be referred to. DNA to be hybridized includes DNA or its fragment, containing a base sequence which is at least 40%, preferably 60%, more preferably 90% or greater, homologous to the genomic DNA of the present invention.

(c) Recombinant Vector, Transformant

It is necessary for a nitrile hydratase gene to be put into a vector so that nitrile hydratase is expressed in the host organism to be transformed. Examples of such vectors are plasmid DNA, bacteriophage DNA, retrotransposon DNA, artificial chromosome DNA and the like.

In addition, a host to be used in the present invention is not limited to any specific type as long as it can express the target nitrile hydratase after the recombinant vector is introduced into the host. Examples are bacteria such as *E. coli* and *Bacillus subtilis*, yeasts, animal cells, insect cells, plant cells and the like. When *E. coli* is used as a host, an expression vector with high expression efficiency, such as expression vector pkk 233-2 with a trc promoter (made by Amersham Biosciences Corp.), pTrc 99A (made by Amersham Biosciences Corp.) or the like, is preferred.

In addition to a nitrile hydratase gene, a vector may be coupled with a promoter, terminator, enhancer, splicing signal, poly A addition signal, selection marker, ribosome binding sequence (SD sequence) or the like. Examples of selection markers are kanamycin resistance gene, dihydrofolate reductase gene, ampicillin resistance gene, neomycin resistance gene and the like.

When a bacterium is used as a host, *Escherichia coli* may be used, for example, and a *Rhodococcus* strain such as *Rhodococcus rhodochrous* ATCC 12674, *Rhodococcus rhodochrous* ATCC 17895 and *Rhodococcus rhodochrous* ATCC 19140 may also be used. Those ATCC strains are obtained from the American type culture collection.

When *E. coli* is used as a host for producing a transformant to express a nitrile hydratase, since most of the expressed nitrile hydratase is formed as an inclusion body and is insoluble, a transformant with low catalytic activity is obtained. On the other hand, if a *Rhodococcus* strain is used as a host, nitrile hydratase is present in the soluble fraction, and a transformant with high activity is obtained. Those transformants may be selected based on purposes. However, when an improved enzyme is selected under stringent conditions, a transformant with high activity derived from a *Rhodococcus* strain is preferred.

Introducing a recombinant vector into a bacterium is not limited to any specific method as long as DNA is introduced into the bacterium. For example, a method using calcium ions, electroporation or the like may be employed.

When yeast is used as a host, examples are *Saccharomyces cerevisiae, Schizosaccharomyces pombe, Pichia pastoris* and the like. As a method for introducing a recombinant vector into yeast, it is not limited specifically as long as DNA is introduced into the yeast. For example, an electroporation method, spheroplast method, lithium acetate method or the like may be employed.

When animal cells are used as a host, monkey cells COS-7, Vero, CHO cells, mouse L cells, rat GH3 cells, human FL cells or the like may be employed. As a method for introducing a recombinant vector into animal cells, for example, an electroporation method, calcium phosphate method, lipofection method or the like may be used.

When insect cells are used as a host, Sf9 cells, Sf21 cells or the like may be used. A method for introducing a recombinant vector into insect cells, for example, a calcium phosphate method, lipofection method, electroporation method or the like may be used.

When plant cells are used as a host, tobacco BY-2 cells or the like may be used. However, that is not the only option. A method for introducing a recombinant vector into plant cells, for example, an *Agrobacterium* method, particle gun method, PEG method, electroporation method or the like may be used.

(d) Method for Producing Culture and Improved Nitrile Hydratase

An improved nitrile hydratase of the present invention is obtained by incubating the above transformant and by collecting from the obtained culture.

The present invention also relates to a method for producing an improved nitrile hydratase, and the method is characterized by collecting an improved nitrile hydratase from the culture above.

In the present invention, "culture" means any of culture supernatant, cell cultured cell, bacterial-cell culture, and cell homogenates or bacterial-cell homogenates. To incubate a transformant of the present invention, a generally used method for incubating a host is used. The target nitrile hydratase is accumulated in the culture.

As for a culture to incubate a transformant of the present invention, a natural or synthetic culture medium is used as long as it contains a carbon source, a nitrogen source, inorganic salts or the like for the host bacteria to assimilate, and incubation of a transformant is performed efficiently. Examples of a carbon source are carbohydrates such as glucose, galactose, fructose, sucrose, raffinose and starch; organic acids such as acetic acid and propionic acid; alcohols such as ethanol and propanol; and the like. Examples of a nitrogen source are inorganic acids such as ammonia, ammonium chloride, ammonium sulfate, ammonium acetate and ammonium phosphate; ammonium salts of organic acids; and other nitrogen-containing compounds.

In addition, peptone, yeast extract, meat extract, corn steep liquor, various amino acids or the like may also be used. Examples of minerals are monopotassium phosphate, potassium dihydrogenphosphate, magnesium phosphate, magnesium sulfate, sodium chloride, ferrous sulfate, manganese sulfate, zinc sulfate, copper sulfate, calcium carbonate and the like. Also, if necessary, a defoaming agent may be used to prevent foaming during the incubation process. Moreover, cobalt ions or iron ions as prosthetic molecules of a nitrile hydratase, or nitriles and amides as an inducer of the enzyme, may also be added to the culture.

Incubation may be conducted by adding selective pressure to prevent the vector and the target gene from being eliminated. Namely, if a selection marker is a drug-resistant gene, a corresponding chemical agent may be added; or if a selection marker is an auxotrophic complementary gene, corresponding nutrition factors may be removed.

Also, if a selection marker has a genetic assimilation trait, an equivalent assimilation factor may be added as a sole factor if necessary. For example, when *E. coli* transformed by a vector containing an ampicillin-resistant gene is incubated, ampicillin may be added as needed during the incubation process.

When incubating a transformant transformed by an expression vector containing an inducible promoter, such an inducer may be added to the culture if necessary. For example, when incubating a transformant transformed by an expression vector with a promoter inducible with isopropyl-β-D-thiogalactopyranoside (IPTG), IPTG or the like may be added to the culture. Likewise, when incubating a transformant transformed by an expression vector with a trp promoter inducible with indoleacetic acid (IAA), IAA or the like may be added to the culture.

Incubation conditions of a transformant are not limited specifically as long as the productivity of the target nitrile hydratase and growth of the host are not prohibited. Generally, conditions are preferred to be 10° C.~40° C., more preferably 20° C.~37° C., for 5~100 hours. The pH value is adjusted using inorganic or organic acid, alkaline solution or the like. If it is an *E. coli*, the pH is adjusted to be 6~9.

As for incubation methods, solid-state culture, static culture, shaking culture, aeration-agitation culture and the like may be used. When an *E. coli* transformant is incubated, it is especially preferred to use shaking culture or aeration-agitation culture (jar fermentation) under aerobic conditions.

When incubated in culture conditions above, the improved nitrile hydratase of the present invention is accumulated at a high yield in the above culture medium, namely, at least in any of culture supernatant, cell culture, bacterial-cell culture, cell homogenates or bacterial-cell homogenates.

When an improved nitrile hydratase is incubated and produced in a cell or bacterial cell, the target nitrile hydratase is collected by homogenizing the cells or bacterial cells. Cells or bacterial cells are homogenized by high-pressure treatment using a French press or homogenizer, supersonic treatment, grinding treatment using glass beads or the like, enzyme treatment using lysozyme, cellulose, pectinase and the like, freezing and thawing treatment, hypotonic solution treatment, bacteriolysis induction treatment by phage, and so on.

After the homogenization process, residues of cell homogenates or bacterial-cell homogenates (including insoluble fractions of the cell extract) are removed if necessary. To remove residues, centrifugal or filtration methods are employed. To increase the efficiency of removing residues, a coagulant or filter aid may be used. The supernatant obtained after the removal of residues is soluble fractions of the cell extract, which are used as a crudely purified improved nitrile hydratase solution.

Also, when an improved nitrile hydratase is produced in a bacterial cell or in cells, it is an option to collect the bacterial cell or the cells themselves by a centrifuge or membrane filtration and to use without homogenizing them.

When an improved nitrile hydratase is produced outside cells or bacterial cells, the culture may be used as is, or the cells or bacterial cells are removed using a centrifugal or filtration method. Then, the improved nitrile hydratase is collected from the culture by being extracted through ammonium sulfate precipitation, if necessary. Furthermore, dialysis or various chromatography techniques (gel filtration, ion exchange chromatography, affinity chromatography, etc.) may be used to isolate and purify the nitrile hydratase.

To check the production yield of a nitrile hydratase obtained by incubating a transformant is not limited to using any specific method, but SDS-PAGE (polyacrylamide gel electrophoresis), nitrile hydratase activity measurements or the like may be used to determine the yield per culture, per wet or dry weight in a bacterial cell, or per crude enzymatic protein. SDS-PAGE may be conducted by a method well known by a person skilled in the art. Also, the activity described above may be applied to nitrile hydratase activity.

Without using any living cells, an improved nitrile hydratase of the present invention may be produced using a cell-free protein synthesis system.

In a cell-free protein synthesis system, a protein is produced in an artificial vessel such as a test tube using a cell extract. A cell-free protein synthesis system used in the present application includes a cell-free transcription system that synthesizes RNA using DNA as a template.

In such a case, an organism corresponding to the above host is the organism from which the cell extract is derived. Here, for the cell extract, extracts of eukaryotic or prokaryotic origin, such as the extract from wheat germ, *E. coli* and the like, may be used. Such cell extracts may be concentrated or not.

The cell extract is obtained by ultrafiltration, dialysis, polyethylene glycol (PEG) precipitation or the like. In the present invention, a commercially available kit may also be used for cell-free protein synthesis. Examples of such a kit are a reagent kit PROTEIOS™ (Toyobo), TNT™ system (Promega KK), a synthesizer PG-Mate™ (Toyobo), RTS (Roche Diagnostics) and the like.

An improved nitrile hydratase obtained by cell-free protein synthesis as described above is also purified by properly selecting a chromatography type.

2. Method for Producing Amide Compound

The improved nitrile hydratase obtained above is used as an enzymatic catalyst for material production. For example, an amide compound is produced by bringing a nitrile compound into contact with the improved nitrile hydratase. Then, the amide compound produced upon contact is collected. Accordingly, an amide compound is produced.

The isolated and purified nitrile hydratase as described above is used as an enzymatic catalyst. In addition, a gene is introduced so as to express an improved nitrile hydratase in a proper host as described above and the culture after the host is incubated or the processed products of the culture may also be used. Processed products are, for example, incubated cells immobilized with acrylamide gel or the like, those processed by glutaraldehyde, those supported by inorganic carriers such as alumina, silica, zeolite, diatomaceous earth and the like.

Here, "contact" means that an improved nitrile hydratase and a nitrile compound are present in the same reaction system or incubation system: for example, an isolated and purified improved nitrile hydratase and a nitrile compound are mixed; a nitrile compound is added into a incubation vessel of a cell to express an improved nitrile hydratase gene; cells are incubated in the presence of a nitrile compound; a cell extract is mixed with a nitrile compound; and so on.

A nitrile compound as a substrate is selected by considering the substrate specificity of the enzyme, stability of the enzyme in the substrate and the like. As for a nitrile compound, acrylonitrile is preferred. The reaction method and the method for collecting an amide compound after the completion of reactions are properly selected depending on the characteristics of the substrate and the enzymatic catalyst.

The enzymatic catalyst is preferred to be recycled as long as its activity is not deactivated. From the viewpoint of preventing deactivation and of recycling ease, the enzymatic catalyst is preferred to be used as a processed product.

EXAMPLES

In the following, examples of the present invention are described in detail. However, the present invention is not limited to those. *Rhodococcus rhodochrous* J1 strain is registered under accession number "FERM BP-1478" at the International Patent Organism Depositary, National Institute of Advanced Industrial Science and Technology (Central 6, 1-1-1 Higashi, Tsukuba, Ibaraki), deposited Sep. 18, 1987.

Preparation Example 1

Preparation of Plasmid pSJ034

As a template to perform the amino-acid substitution of the present invention, plasmid pSJ034 (FIG. 1) having the nitrile hydratase gene of the J1 strain was produced by the following method.

Plasmid pSJ034 is capable of expressing nitrile hydratase in a *Rhodococcus* strain. Plasmid pSJ034 was produced from pSJ023 by the method disclosed in JP publication H10-337185. Namely, partially cleaved at the XbaI site and ligated with the Sse8387I linker, plasmid pSJ033 was prepared so that one XbaI site of plasmid pSJ023 was substituted with Sse8387I. Next, plasmid pSJ033 was partially cleaved at the Sse8387I site, and a Klenow fragment was used to blunt the ends so as to cause self ligation. Accordingly, plasmid pSJ034 was obtained. Here, pSJ023 is a transformant "*R. rhodochrous* ATCC 12674/pSJ023," and is internationally registered under accession number "FERM BP-6232" at the International Patent Organism Depositary, National Institute of Advanced Industrial Science and Technology (Central 6, 1-1-1 Higashi, Tsukuba, Ibaraki), deposited Mar. 4, 1997.

Preparation Example 2

Preparation of Plasmid pFR005

(1) Construction of Mutant Gene Library

Figure 5:
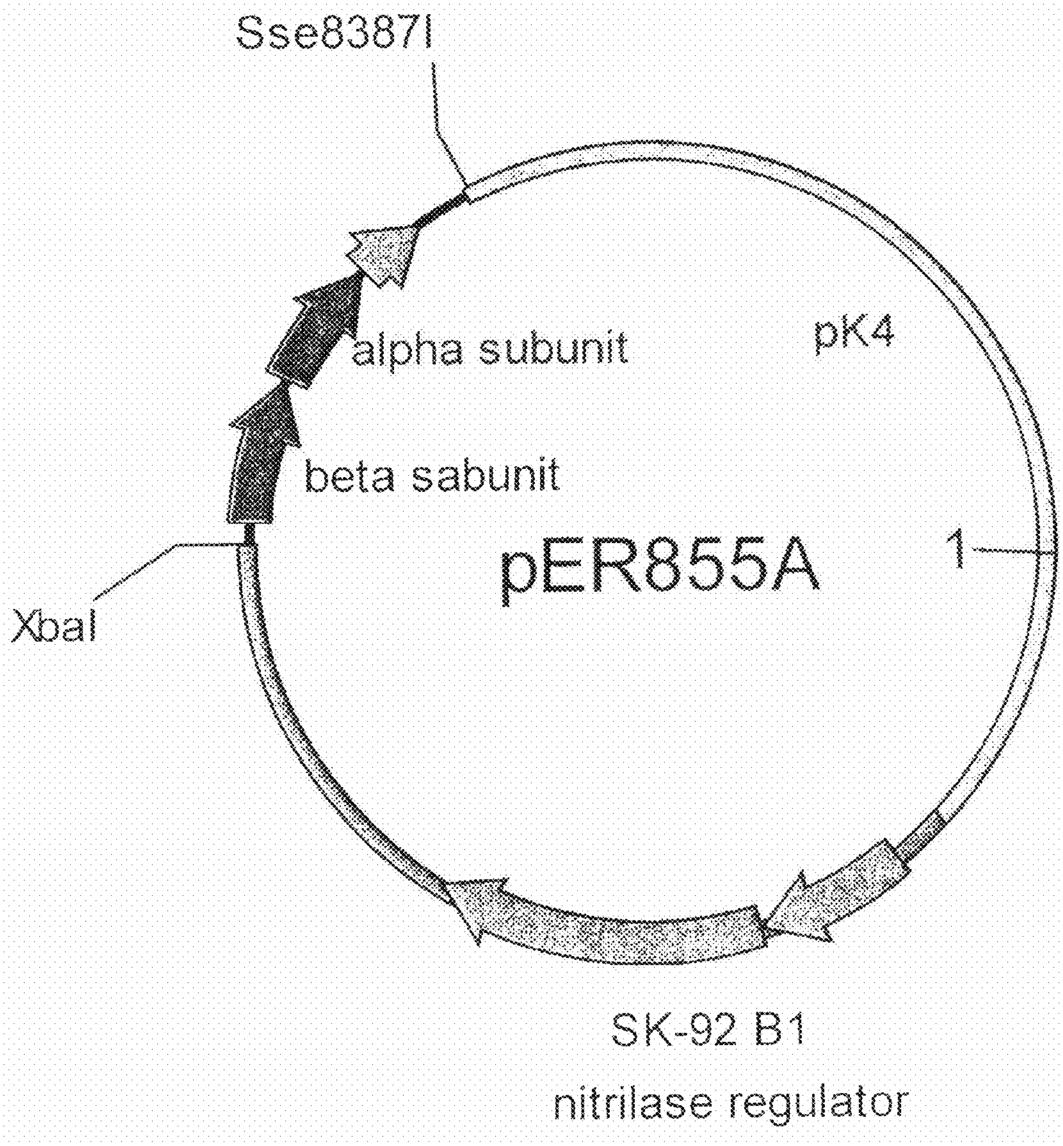
FIG. 5 is a view showing the structure of plasmid pER855A.

As for a template plasmid, pER855A (FIG. 5) was used, prepared by modifying plasmid pER855 (see JP publication 2010-172295) as follows: counted downstream from the N-terminal amino-acid residue of the amino-acid sequence (SEQ ID NO: 2) in the β subunit, an amino-acid residue at position 167 was mutated from asparagine (N) to serine (S); an amino-acid residue at position 219 was mutated from valine (V) to alanine (A); an amino-acid residue at position 57 was mutated from serine (S) to methionine (M); an amino-acid residue at position 114 was mutated from lysine (K) to tyrosine (Y); and an amino-acid residue at position 107 was mutated from threonine (T) to lysine (K).

First, introduction of a mutation into the nitrile hydratase gene was conducted as follows:

<Composition of PCR Reaction Mixture>

| | |
|---|---|
| sterile water | 20 μL |
| pER855A (1 ng/mL) | 1 μL |
| Forward primer (10 mM) | 2 μL |
| Reverse primer (10 mM) | 2 μL |
| PrimeSTAR MAX (2x) | 25 μL |
| total | 50 μL |

<PCR Reaction Conditions>

(98° C. for 10 sec, 55° C. for 5 sec, 72° C. for 90 sec)×30 cycles

<Primers> Primers for Saturation Mutagenesis at β17

```
β17RM-F:
                                    (SEQ ID NO: 63)
ggatacggaccggtcNNStatcagaaggacgag

β17RM-R:
                                    (SEQ ID NO: 64)
ctcgtccttctgataSNNgaccggtccgtatcc
```

<Reaction Conditions>

(94° C. for 30 sec, 65° C. for 30 sec, 72° C. for 3 min)×30 cycles

After the completion of PCR, 5 μL of the reaction mixture was provided for 0.7% agarose gel electrophoresis, an amplified fragment of 11 kb was confirmed, and 1 μL DpnI (provided with the kit) was added to the PCR reaction mixture, which was then reacted at 37° C. for an hour. Accordingly, the template plasmid was removed. After that, the reaction mixture was purified using Wizard SV Gel and PCR Clean-Up System (Promega KK), and transformation was introduced into JM109 using the purified PCR reaction product. A few thousand obtained colonies were collected from the plate, and plasmid DNA was extracted using QIAprep Spin Miniprep Kit (Qiagen) to construct a mutant gene library.

(2) Producing *Rhodococcus* Transformant

The cells of *Rhodococcus rhodochrous* strain ATCC 12674 at a logarithmic growth phase were collected by a centrifugal separator, washed with ice-cooled sterile water three times and suspended in the sterile water. Then, 1 μL of plasmid prepared in (2) above and 10 μL of the bacterial-cell suspension were mixed and ice-cooled. The plasmid DNA and the bacterial-cell suspension were supplied into a cuvette, and electric pulse treatment was conducted at 2.0 KV and 200Ω using an electroporation device, Gene Pulser II (Bio-Rad Laboratories, Inc.).

The cuvette with the mixture processed by electric pulse was let stand for 10 minutes under ice-cold conditions, and a heat-shock treatment was conducted at 37° C. for 10 minutes. Then, 500 μL of an MYK culture medium (0.5% polypeptone, 0.3% Bacto yeast extract, 0.3% Bacto malt extract, 0.2% $K_2HPO_4$, 0.2% $KH_2PO_4$) was added and let stand at 30° C. for 5 hours, and the strain was then applied on an MYK agar medium containing 50 μg/mL kanamycin. The colony obtained after being incubated at 30° C. for 3 days was used as a transformant. In the same manner, transformant pER 855A was prepared as a comparative strain.

(3) Amide Treatment on *Rhodococcus* Strain Transformant

The *Rhodococcus* transformant containing nitrile hydratase gene, obtained in (2) above and ATCC 12674/pER855A as a comparative strain were used for screening. In a 96-hole deep-well plate, 1 mL each of a GGPK culture medium (1.5% glucose, 1% sodium glutamate, 0.1% yeast extract, 0.05% $K_2HPO_4$, 0.05% $KH_2P$ $O_4$, 0.05% $MgSO_4.7H_2O$, 1% $CoCl_2$, 0.1% urea, 50 μg/mL kanamycin, pH 7.2) was supplied. In each culture medium, the above strain was inoculated, and subjected to liquid culture at 30° C. for 3 days.

Next, 30 μL of the liquid culture obtained above was dispensed in a 96-hole plate and the culture medium was removed by centrifugation. Lastly, 40 μL of a 50% acrylamide solution was added to suspend the bacteria. The transformant suspended in a high-concentration acrylamide solution was put in an incubator to completely deactivate the comparative strain through heat treatment conducted at 50° C. for 30 minutes. The remaining nitrile hydratase activity was measured as follows.

First, after the acrylamide treatment, a transformant was washed with a 50 mM phosphate buffer (pH 7.0) and the activity was measured by the following method. The washed transformant and 50 mM phosphate buffer (pH 7.0) were supplied to a test tube and preincubated at 30° C. for 10 minutes, and an equivalent volume of a 5% acrylonitrile solution (pH 7.0) was added and reacted for 10 minutes. Then, one tenth volume of 1 M phosphoric acid was added to terminate the reaction. Next, the transformant was removed from the terminated reaction mixture by centrifugation, and the mixture was diluted to a proper concentration for analysis by HPLC (WAKOSIL 5C8 (Wako Pure Chemical Industries) 250 mm long, 10% acetonitrile containing 5 mM phosphoric acid, flow rate of mobile phase at 1 mL/min, wavelength of a UV absorption detector 260 nm). Using untreated cells for which acrylamide treatment was not conducted, activity was measured for comparison. Then, based on the obtained activity values, the remaining activity after acrylamide treatment was determined.

Among hundreds of transformants containing a mutant nitrile hydratase gene obtained above, mutant enzyme pFR005 showing resistance to a high-concentration acrylamide was selected.

(4) Confirming Base Sequence

To confirm the base sequence of the nitrile hydratase gene, plasmid was recovered from the selected strains. *Rhodococcus* transformants were inoculated in 10 mL of an MYK culture medium (0.5% polypeptone, 0.3% Bacto yeast extract, 0.3% malt extract, 1% glucose, 50 μg/mL kanamycin) and incubated for 24 hours, and a 20% sterile glycine solution was added to make the final concentration of 2%, and further incubated for another 24 hours. Then, the bacterial cells were recovered by centrifugation, washed with a TES buffer (10 mM Tris-HCl (pH 8)-10 mM NaCl-1 mM EDTA), suspended in 2 mL of 50 mM Tris-HCl (pH8)-12.5% sucrose-100 mM NaCl-1 mg/mL lysozyme, and subjected to shaking culture at 37° C. for 3 hours. Then, 0.4 mL of 10% SDS was added and the mixture was shaken gently for an hour at room temperature, to which 2.1 mL of 5 M sodium acetate buffer (pH 5.2) was added and let stand in ice for an hour. Next, the mixture was centrifuged for an hour at 10,000×g at 4° C. to obtain a supernatant, to which a 5-times volume ethanol was added and let stand at −20° C. for 30 minutes. Then, the mixture was centrifuged at 10,000×g for 20 minutes. The precipitate was washed with 10 mL of 70% ethanol and dissolved in 100 μL of a TE buffer. Accordingly, a DNA solution was obtained.

Next, the sequence including nitrile hydratase was amplified by a PCR method.

<Composition of PCR Reaction Mixture>

| | |
|---|---|
| template plasmid | 1 μL |
| 10x PCR buffer (made by NEB) | 10 μL |
| primer NH-19 (50 μM) | 1 μL |
| primer NH-20 (50 μM) | 1 μL |
| 2.5 mM dNTPmix | 8 μL |
| sterile water | 79 μL |
| Taq DNA polymerase (made by NEB) | 1 μL |

<Primers>

NH-19: (SEQ ID NO: 65)
GCCTCTAGATATCGCCATTCCGTTGCCGG

NH-20: (SEQ ID NO: 66)
ACCCTGCAGGCTCGGCGCACCGGATGCCCAC

<Reaction Conditions>
(94° C. for 30 sec, 65° C. for 30 sec, 72° C. for 3 min)×30 cycles After completion of PCR, 5 μL of the reaction mixture was subjected to 0.7% agarose gel electrophoresis to detect a 2.5 kb PCR amplified product. After Exo-SAP treatment (Amersham Pharmacia Biotech) on the PCR reaction mixture, samples for alignment analysis were prepared by a cycle sequencing method, and were analyzed using CEQ-2000XL (Beckman Coulter). As a result, the mutation positions of pFR005 were confirmed to be Nβ167S, Vβ219A, Sβ57M, Kβ114Y, Tβ107K and Pβ17G. Namely, in plasmid pFR005, proline at position 17 in the β subunit was mutated to glycine, serine at position 57 in the β subunit was mutated to lysine, tyrosine at position 107 in the β subunit was mutated to lysine, lysine at position 114 in the β subunit was mutated to tyrosine, asparagine at position 167 in the β subunit was mutated to serine, and valine at position 219 in the β subunit was mutated to alanine.

Example 1

Preparation of Improved Nitrile Hydratase

Using pSJ034 formed in preparation example 1, amino-acid substitution was conducted. The following composition of a reaction mixture, reaction conditions and primers were used for the PCR.

<Composition of PCR Reaction Mixture>

| | |
|---|---|
| sterile water | 20 μL |
| pSJ034 (1 ng/mL) | 1 μL |
| Forward primer (10 mM) | 2 μL |
| Reverse primer (10 mM) | 2 μL |
| PrimeSTAR MAX (2x) | 25 μL |
| total | 50 μL |

<PCR Reaction Conditions>
(98° C. for 10 sec, 55° C. for 5 sec, 72° C. for 90 sec)×30 cycles <Primers>

TABLE 5

| substituted amino acid | name of primer | sequence | SEQ ID NO |
|---|---|---|---|
| C | β48C-F | TCGTGGTGCGACAAGTCGCGGTTCTTC | 13 |
| | β48C-R | CTTGTCGCACCACGATATGCCCTTGAG | 14 |
| D | β48D-F | TCGTGGGACGACAAGTCGCGGTTCTTC | 15 |
| | β48D-R | CTTGTCGTCCCACGATATGCCCTTGAG | 16 |
| E | β48E-F | TCGTGGGAGGACAAGTCGCGGTTCTTC | 17 |
| | β48E-R | CTTGTCCTCCCACGATATGCCCTTGAG | 18 |
| H | β48H-F | TCGTGGCACGACAAGTCGCGGTTCTTC | 19 |
| | β48H-R | CTTGTCGTGCCACGATATGCCCTTGAG | 20 |

TABLE 5-continued

| substituted amino acid | name of primer | sequence | SEQ ID NO |
|---|---|---|---|
| I | β48I-F | TCGTGGATCGACAAGTCGCGGTTCTTC | 21 |
| | β48I-R | CTTGTCGATCCACGATATGCCCTTGAG | 22 |
| K | β48K-F | TCGTGGAAGGACAAGTCGCGGTTCTTC | 23 |
| | β48K-R | CTTGTCCTTCCACGATATGCCCTTGAG | 24 |
| M | β48M-F | TCGTGGATGGACAAGTCGCGGTTCTTC | 25 |
| | β48M-R | CTTGTCCATCCACGATATGCCCTTGAG | 26 |
| N | β48N-F | TCGTGGAACGACAAGTCGCGGTTCTTC | 27 |
| | β48N-R | CTTGTCGTTCCACGATATGCCCTTGAG | 28 |
| P | β48P-F | TCGTGGCCGGACAAGTCGCGGTTCTTC | 29 |
| | β48P-R | CTTGTCCGGCCACGATATGCCCTTGAG | 30 |
| Q | β48Q-F | TCGTGGCAGGACAAGTCGCGGTTCTTC | 31 |
| | β48Q-R | CTTGTCCTGCCACGATATGCCCTTGAG | 32 |
| S | β48S-F | TCGTGGTCCGACAAGTCGCGGTTCTTC | 33 |
| | β48S-R | CTTGTCGGACCACGATATGCCCTTGAG | 34 |
| T | β48T-F | TCGTGGACCGACAAGTCGCGGTTCTTC | 35 |
| | β48T-R | CTTGTCGGTCCACGATATGCCCTTGAG | 36 |

After the completion of PCR, 5 μL of the reaction mixture was subjected to 0.7% agarose gel electrophoresis and an 11-kb PCR amplified product was detected. Then, 1 μL of DpnI (provided in the kit) was added to the PCR reaction mixture and reacted at 37° C. for an hour to remove the template plasmid. After the reaction was completed, the reaction mixture was purified using Wizard SV Gel and PCR Clean-Up System (made by Promega KK), and the purified PCR product was used to transform JM109. From the obtained culture, plasmid DNA was extracted using QIAprep Spin Miniprep Kit (made by Qiagen), and the base sequence of the nitrile hydratase was confirmed using automated sequencer CEQ 8000 (made by Beckman Coulter, Inc.). Obtained plasmids were named as follows.

TABLE 6

| name of plasmid | amino-acid substitution |
|---|---|
| pSJ102 | Wβ48C |
| pSJ103 | Wβ48D |
| pSJ104 | Wβ48E |
| pSJ107 | Wβ48H |
| pSJ108 | Wβ48I |
| pSJ109 | Wβ48K |
| pSJ111 | Wβ48M |
| pSJ112 | Wβ48N |
| pSJ113 | Wβ48P |
| pSJ114 | Wβ48Q |
| pSJ116 | Wβ48S |
| pSJ117 | Wβ48T |

Example 2

Preparation of *Rhodococcus* Transformant

Cells of *Rhodococcus rhodochrous* strain ATCC 12674 in a logarithmic growth phase were collected using a centrifuge, washed three times with ice-cold sterile water, and suspended in the sterile water. Then, 1 μL of plasmid prepared in example 1 and 10 μL of the bacterial-cell suspension were mixed and ice-cooled. The DNA and the bacterial-cell suspension were supplied in a cuvette, and electric pulse treatment was conducted using an electroporation device, Gene Pulser (Bio-Rad Laboratories), under conditions of 2.0 kV and 200Ω. The electric-pulse processed mixture was let stand in an ice-cold condition for 10 minutes, and subjected to heat shock at 37° C. for 10 minutes. After 500 μL of an MYK culture medium (0.5% polypeptone, 0.3% Bacto yeast extract, 0.3% Bacto malt extract, 0.2% $K_2HPO_4$, 0.2% $KH_2PO_4$) was added and let stand at 30° C. for 5 hours, the strain was applied onto an MYK agar culture medium containing 50 μg/mL kanamycin and incubated at 30° C. for 3 days. The obtained colony after incubating at 30° C. for 3 days was used as a transformant.

Each transformant obtained above was inoculated into an MYK culture medium (50 μg/mL kanamycin), and subjected to shaking culture at 30° C. for 2 days. Then, 1% culture was inoculated into a GGPK culture medium (1.5% glucose, 1% sodium glutamate, 0.1% yeast extract, 0.05% $K_2HPO_4$, 0.05% $KH_2P\ O_4$, 0.05% $Mg_2O_4.7H_2O$, 1% $CoCl_2$, 0.1% urea, 50 μg/mL kanamycin, pH 7.2), and subjected to shaking culture at 30° C. for 3 days. Bacterial cells were collected by using a centrifuge, and were washed with a 100 mM phosphate buffer (pH 7.0) to prepare a bacterial-cell suspension.

Example 3

Improved Nitrile Hydratase Activity

The nitrile hydratase activity in the obtained bacterial-cell suspension was measured by the following method: 0.2 mL of the bacterial-cell mixture and 4.8 mL of a 50 mM phosphate buffer (pH 7.0) were mixed, to which 5 mL of a 50 mM phosphate buffer (pH 7.0) containing 5.0% (w/v) acrylonitrile was further added. Next, the mixture was reacted while being shaken at 10° C. for 10 minutes. Then, bacterial cells were filtered and the amount of produced acrylamide was determined using gas chromatography.

<Analysis Conditions> analysis instrument: gas chromatograph GC-14B (Shimadzu Corporation)

detector: FID (detection at 200° C.)

column: 1 m glass column filled with PoraPak PS (column filler made by Waters Corp.)

column temperature: 190° C.

Nitrile hydratase activity was determined by conversion from the amount of acrylamide. Here, regarding nitrile hydratase activity, the amount of enzyme to produce 1 μmol of acrylamide per 1 minute is set as 1 U. Table 7 shows relative activities when the parent strain activity without amino-acid substitution was set at 1.0.

TABLE 7

Measurement results of catalytic activity

| amino-acid substitution | name of plasmid | catalytic activity (relative value) |
|---|---|---|
| none (parent strain) | pSJ034 | 1.0 (comp. example) |
| Wβ48D | pSJ103 | 1.2 |
| Wβ48E | pSJ104 | 1.6 |
| Wβ48K | pSJ109 | 1.1 |
| Wβ48M | pSJ111 | 3.1 |
| Wβ48N | pSJ112 | 1.8 |
| Wβ48P | pSJ113 | 2.0 |
| Wβ48S | pSJ116 | 1.1 |
| Wβ48T | pSJ117 | 1.3 |

From the results above, enhanced enzymatic activity was confirmed in the improved nitrile hydratase in which an amino acid at position 48 in the β subunit was substituted with aspartic acid, lysine, asparagine, proline, serine or threonine.

Example 4

Preparation and Evaluation of Improved Nitrile Hydratase

Plasmid pFR005 formed in preparation example 2 as a template plasmid was used to substitute an amino acid at position 48 of the β subunit.

Namely, using the method in example 1, each of the improved nitrile hydratases with a substituted amino acid were prepared, and a transformant was obtained by the method in example 2. Further, the enzymatic activity was measured by the same method in example 3. The results are shown in Table 8.

TABLE 8

Measurement results of catalytic activity

| name of plasmid | amino-acid substitution | catalytic activity (relative value) |
|---|---|---|
| pFR005 | Pβ17G, Sβ57K, Tβ107K, Kβ114Y, Nβ167S, Vβ219A | 1.0 (comp. example) |
| pER1102 | Pβ17G, Sβ57K, Tβ107K, Kβ114Y, Nβ167S, Vβ219A, Wβ48C | 1.6 |
| pER1103 | Pβ17G, Sβ57K, Tβ107K, Kβ114Y, Nβ167S, Vβ219A, Wβ48D | 1.7 |
| pER1104 | Pβ17G, Sβ57K, Tβ107K, Kβ114Y, Nβ167S, Vβ219A, Wβ48E | 1.3 |
| pER1107 | Pβ17G, Sβ57K, Tβ107K, Kβ114Y, Nβ167S, Vβ219A, Wβ48H | 1.2 |
| pER1108 | Pβ17G, Sβ57K, Tβ107K, Kβ114Y, Nβ167S, Vβ219A, Wβ48I | 1.6 |
| pER1109 | Pβ17G, Sβ57K, Tβ107K, Kβ114Y, Nβ167S, Vβ219A, Wβ48K | 1.4 |
| pER1112 | Pβ17G, Sβ57K, Tβ107K, Kβ114Y, Nβ167S, Vβ219A, Wβ48M | 3.7 |
| pER1113 | Pβ17G, Sβ57K, Tβ107K, Kβ114Y, Nβ167S, Vβ219A, Wβ48N | 1.7 |
| pER1114 | Pβ17G, Sβ57K, Tβ107K, Kβ114Y, Nβ167S, Vβ219A, Wβ48P | 1.7 |
| pER1116 | Pβ17G, Sβ57K, Tβ107K, Kβ114Y, Nβ167S, Vβ219A, Wβ48Q | 1.9 |
| pER1117 | Pβ17G, Sβ57K, Tβ107K, Kβ114Y, Nβ167S, Vβ219A, Wβ48S | 1.8 |
| pER1119 | Pβ17G, Sβ57K, Tβ107K, Kβ114Y, Nβ167S, Vβ219A, Wβ48T | 1.1 |

From the results above, the same enzymatic activity was confirmed in the mutant nitrile hydratase when the amino acid at $X_4$ (corresponding to an amino acid at position 48 in the β subunit) in the amino-acid sequence shown in SEQ ID NO: 50 was substituted with an amino acid selected from among cysteine, glutamic acid, aspartic acid, histidine, isoleucine, lysine, methionine, asparagine, proline, glutamine, serine and threonine.

Example 5

SDS-Polyacrylamide Gel Electrophoresis

Figure 4:
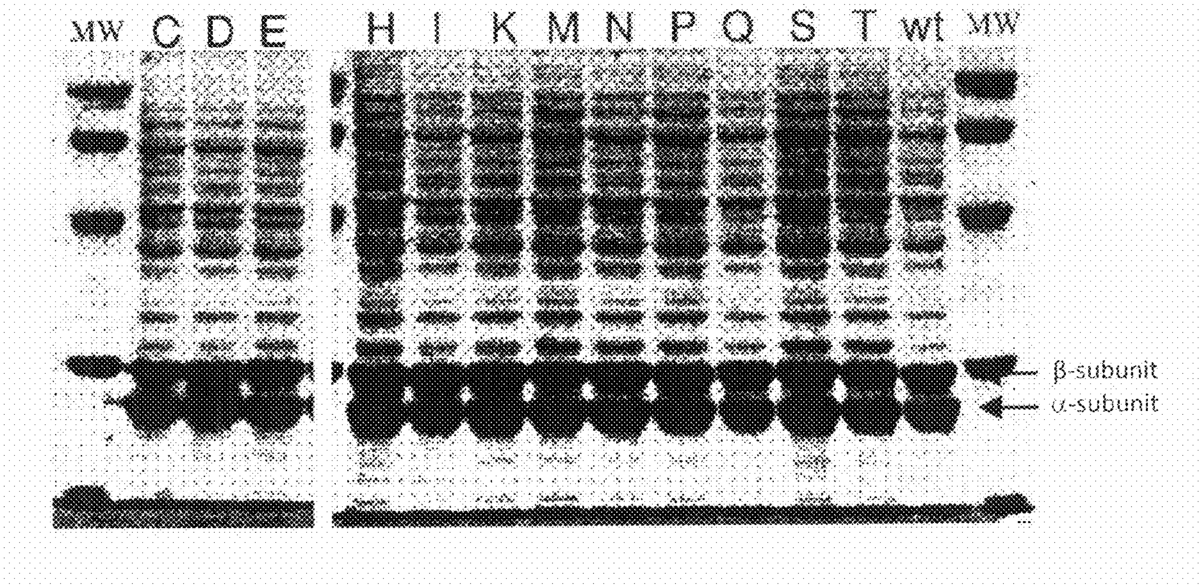
FIG. 4 is a photograph showing results of SDS-PAGE.

Using a sonicator VP-300 (TAITEC Corporation), the bacterial-cell suspension prepared in example 2 was homogenized for 10 minutes while being ice-cooled. Next, the bacterial-cell homogenate was centrifuged at 13500 rpm for 30 minutes and a cell-free extract was obtained from the supernatant. After the protein content of the cell extract was measured using a Bio-Rad protein assay kit, the cell extract was mixed with a polyacrylamide gel electrophoresis sample buffer (0.1 M Tris-HCl (pH 6.8), 4% w/v SDS, 12% v/v β mercaptoethanol, 20% v/v glycerol, and a trace of bromophenol blue), and boiled for 5 minutes for denaturation. A 10% acrylamide gel was prepared and denatured samples were applied to have an equivalent protein mass per one lane to conduct electrophoresis analysis (FIG. 4).

As a result, since hardly any difference was observed in the band strength of nitrile hydratase in all the samples, the expressed amount of nitrile hydratase was found to be the same. Accordingly, the enzymatic specific activity was found to be attributed to the improved enzymatic activity.

Example 6

Preparation of Transformant Containing Nitrile Hydratase Derived from *Rhodococcus Rhodochrous* M8 Strain (Hereinafter Referred to as M8 Strain)

(1) Preparation of Chromosomal DNA from M8 Strain

The M8 strain (SU 1731814) is obtained from the Russian Institute of Microorganism Biochemistry and Physiology (VKPM S-926). In 100 mL of an MYK culture medium (0.5% polypeptone, 0.3% Bacto yeast extract, 0.3% Bacto malt extract, 0.2% $K_2HPO_4$, 0.2% $KH_2PO_4$, pH 7.0), the M8 strain was subjected to shaking culture at 30° C. for 72 hours. The culture mixture was centrifuged, and the collected bacterial cells were suspended in 4 mL of a Saline-EDTA solution (0.1 M EDTA, 0.15 M NaCl, pH 8.0). Then, 8 mg of lysozyme was added to the suspension, which was shaken at 37° C. for 1~2 hours and was frozen at −20° C.

Next, 10 mL of Tris-SDS solution (1% SDS, 0.1M NaCl, 0.1 M Tris-HCl (pH 9.0)) was added to the suspension while the suspension was gently shaken. Proteinase K (Merck KGaA) was further added (final concentration of 0.1 mg) and shaken at 37° C. for 1 hour. Next, an equivalent volume of TE saturated phenol was added, agitated (TE: 10 mM Tris-HCl, 1 mM EDTA (pH 8.0)) and then centrifuged. The supernatant was collected and a double volume of ethanol was added and DNA strands were wrapped around a glass rod. Then, the phenol was removed through centrifugation by successively adding 90%, 80%, and 70% ethanol.

Next, the DNA was dissolved in a 3 mL TE buffer, to which a Ribonuclease A solution (processed at 100° C. for 15 minutes) was added to have a 10 μg/mL concentration and shaken at 37° C. for 30 minutes. Proteinase K (Merck KGaA) was further added and shaken at 37° C. for 30 minutes. After an equivalent volume of TE saturated phenol was added and centrifuged, the mixture was separated into upper and lower layers.

An equivalent volume of TE saturated phenol was further added to the upper layer and centrifuged to separate into upper and lower layers. Such a process was repeated. Then, an equivalent volume of chloroform (containing 4% isoamyl alcohol) was added, centrifuged and the upper layer was collected. Then, a double volume of ethanol was added to the upper layer and the DNA strands were collected by wrapping them around a glass rod. Accordingly, chromosomal DNA was obtained.

(2) Using PCR, Preparation of Improved Nitrile Hydratase from Chromosomal DNA Derived from M8 Strain The nitrile hydratase derived from the M8 strain is described in a non-patent publication (Veiko, V. P. et al., "Cloning, Nucleotide Sequence of Nitrile Hydratase Gene from *Rhodococcus rhodochrous* M8," Russian Biotechnology (Mosc.) 5, 3~5 (1995)). The sequences of β subunit, α subunit and activator are respectively identified in SEQ ID NOs: 37, 38 and 39. Based on the sequence information, primers of SEQ ID numbers 40 and 41 in the sequence listing were synthesized and PCR was performed using the chromosomal DNA prepared in step (1) above as a template.

<Composition of PCR Reaction Mixture>

| | |
|---|---|
| sterile water | 20 μL |
| template DNA (chromosomal DNA) | 1 μL |
| primer M8-1 (10 mM) | 2 μL |
| primer M8-2 (10 mM) | 2 μL |
| PrimeSTAR MAX (2x) | 25 μL |
| total | 50 μL |

<Primers>

```
M8-1:
                                    (SEQ ID NO: 40)
GGTCTAGAATGGATGGTATCCACGACACAGGC

M8-2:
                                    (SEQ ID NO: 41)
cccctgcaggtcagtcgatgatggccatcgattc
```

<Reaction Conditions>

(98° C. for 10 sec, 55° C. for 5 sec, 72° C. for 30 sec)×30 cycles

After the completion of PCR, 5 μL of the reaction mixture was subjected to 0.7% agarose gel electrophoresis (0.7 wt. % Agarose I, made by Doj in Chemical Co., Ltd.) and an amplified fragment of 1.6 kb was detected. The reacted mixture was purified using Wizard SV gel and PCR Clean-Up System (Promega KK).

Next, the collected PCR product was coupled with a vector (pUC118/Hinc II site) using a ligation kit (made by Takara Shuzo Co., Ltd.) so that competent cells of *E. coli* JM109 were transformed using the reaction mixture. A few clones from the obtained transformant colony were inoculated into 1.5 mL of an LB-Amp culture medium, and incubated at 37° C. for 12 hours while being shaken. After incubation was finished, the bacterial cells were collected from the culture through centrifugation. Plasmid DNA was extracted from the collected bacterial cells using QIAprep Spin Miniprep Kit (Qiagen). The base sequence of nitrile hydratase in the obtained plasmid DNA was confirmed using a sequencing kit and automated sequencer CEQ 8000 (Beckman Coulter, Inc.) (SEQ ID NO: 62).

Next, the obtained plasmid DNA was cleaved with restriction enzymes XbaI and Sse8387I, and subjected to 0.7% agarose gel electrophoresis so as to collect a nitrile hydratase gene fragment (1.6 kb), which was then inserted into XbaI-Sse8387I site of plasmid pSJ042. The obtained plasmid was named pSJ-NO1A. Here, pSJ042 as a plasmid capable of expressing nitrile hydratase in *Rhodococcus* J1 strain was prepared by a method described in JP publication 2008-154552 (the content is incorporated in this application by reference). Plasmid pSJ023 used for preparation of pSJ042 is registered as transformant ATCC 12674/pSJ023 (FERM BP-6232) at the International Patent Organism Depositary, National Institute of Advanced Industrial Science and Technology (Central 6, 1-1-1 Higashi, Tsukuba, Ibaraki), deposited Mar. 4, 1997.

Example 7

Preparation and Evaluation of Improved Nitrile Hydratase

Using plasmid pSJ-NO1A obtained in example 6, the amino acid at position 48 of the β subunit was substituted. The same method in example 1 was employed for amino-acid substitution to prepare an improved nitrile hydratase. Next, using the same method in example 3, a transformant of *Rhodococcus rhodochrous* ATCC 12674 strain and its bacterial-cell suspension were prepared. Then, the enzymatic activity was measured by the same method as in example 4. The results are shown in Table 9.

TABLE 9

Measurement results of catalytic activity

| name of plasmid | amino-acid substitution | catalytic activity (relative value) |
|---|---|---|
| pSJ-N01A | none (parent strain) | 1.0 (comp. example) |
| pSJR13 | Wβ48M | 2.4 |
| pSJR21 | Wβ48N | 2.3 |

From the results in table 9, when the amino acid at position 48 of the β subunit was substituted, the enzymatic activity of the improved nitrile hydratase was confirmed to be enhanced the same as in example 3.

Example 8

Preparation of Improved Nitrile Hydratase

Using plasmid pSJ034 formed in preparation example 1, amino-acid substitution was conducted. The following composition of reaction mixture, reaction conditions and primers shown in table 2 were used for the PCR.

<Composition of PCR Reaction Mixture>

| | |
|---|---|
| sterile water | 20 μL |
| pSJ034 (1 ng/mL) | 1 μL |
| Forward primer (10 mM) | 2 μL |
| Reverse primer (10 mM) | 2 μL |
| PrimeSTAR MAX (2x) | 25 μL |
| total | 50 μL |

<PCR Reaction Conditions>

(98° C. for 10 sec, 55° C. for 5 sec, 72° C. for 90 sec)×30 cycles

<Primers>

TABLE 10

| substituted amino acid | name of primer | sequence | SEQ ID NO |
|---|---|---|---|
| A | β37A-F | GTCAATTGCGACTTGGATGCATCTCAAG | 67 |
| | β37A-R | CCAAGTCGCAATTGACAGGGTCCGACC | 68 |
| D | β37D-F | GTCAATTGACACTTGGATGCATCTCAAG | 69 |
| | β37D-R | CCAAGTGTCAATTGACAGGGTCCGACC | 70 |
| F | β37F-F | GTCAATTTTCACTTGGATGCATCTCAAG | 71 |
| | β37F-R | CCAAGTGAAAATTGACAGGGTCCGACC | 72 |
| I | β37I-F | GTCAATTATCACTTGGATGCATCTCAAG | 73 |
| | β37I-R | CCAAGTGATAATTGACAGGGTCCGACC | 74 |

TABLE 10-continued

| substituted amino acid | name of primer | sequence | SEQ ID NO |
|---|---|---|---|
| M | β37M-F | GTCAATTATGACTTGGATGCATCTCAAG | 75 |
| | β37M-R | CCAAGTCATAATTGACAGGGTCCGACC | 76 |
| T | β37T-F | GTCAATTACCACTTGGATGCATCTCAAG | 77 |
| | β37T-R | CCAAGTGGTAATTGACAGGGTCCGACC | 78 |
| V | β37V-F | GTCAATTGTCACTTGGATGCATCTCAAG | 79 |
| | β37V-R | CCAAGTGACAATTGACAGGGTCCGACC | 80 |

After the completion of PCR, 5 μL of the reaction mixture was subjected to 0.7% agarose gel electrophoresis and an amplified fragment of 1 kb was confirmed. Then, 1 μL of DpnI (provided with a kit) was added to the PCR reaction mixture and reacted at 37° C. for an hour to remove the template plasmid. The reacted mixture was purified using Wizard SV gel and PCR Clean-Up System (Promega), and JM109 was transformed using the purified PCR reaction product. Then, a plasmid DNA was extracted from the obtained culture using QIAprep Spin Miniprep Kit (Qiagen), and the base sequence of the nitrile hydratase was confirmed using an automated sequencer CEQ 8000 (Beckman Coulter, Inc.) Obtained plasmids were named as shown in Table 11.

TABLE 11

| name of plasmid | amino-acid substitution |
|---|---|
| pSJ120 | Lβ37A |
| pSJ122 | Lβ37D |
| pSJ124 | Lβ37F |
| pSJ127 | Lβ37I |
| pSJ129 | Lβ37L |
| pSJ130 | Lβ37M |
| pSJ136 | Lβ37T |
| pSJ137 | Lβ37V |

Example 9

Preparation of *Rhodococcus* Transformant

Cells of *Rhodococcus rhodochrous* ATCC 12674 strain in a logarithmic growth phase were collected using a centrifuge, washed three times with ice-cold sterile water, and suspended in the sterile water. Then, 1 μL of plasmid prepared in example 1 and 10 μL of the bacterial-cell suspension were mixed and ice-cooled. The DNA and the bacterial-cell suspension were supplied in a cuvette, and electric pulse treatment was conducted using an electroporation device, Gene Pulser (Bio-Rad Laboratories), under conditions of 2.0 kV and 200Ω. The electric-pulse processed mixture was let stand in an ice-cold condition for 10 minutes, and subjected to heat shock at 37° C. for 10 minutes. After 500 μL of an MYK culture medium (0.5% polypeptone, 0.3% Bacto yeast extract, 0.3% Bacto malt extract, 0.2% $K_2HPO_4$, 0.2% $KH_2PO_4$) was added and let stand at 30° C. for 5 hours, and applied onto an MYK agar culture medium containing 50 μg/mL kanamycin and incubated at 30° C. for 3 days. The obtained colony after incubating at 30° C. for 3 days was used as a transformant.

Each transformant obtained above was inoculated into an MYK culture medium (50 μg/mL kanamycin), and subjected to shaking culture at 30° C. for 2 days. Then, 1% culture was each inoculated into a GGPK culture medium (1.5% glucose, 1% sodium glutamate, 0.1% yeast extract, 0.05% $K_2HPO_4$, 0.05% $KH_2PO_4$, 0.05% $Mg_2O_4.7H_2O$, 1% $CoCl_2$, 0.1% urea, 50 μg/mL kanamycin, pH 7.2), and shaking culture was performed at 30° C. for 3 days. Bacterial cells were collected by using a centrifuge and were washed with a 100 mM phosphate buffer (pH 7.0) to prepare a bacterial-cell suspension.

Example 10

Improved Nitrile Hydratase Activity

The nitrile hydratase activity in the obtained bacterial-cell suspension was measured by the following method: 0.2 mL of the bacterial-cell mixture and 4.8 mL of a 50 mM phosphate buffer (pH 7.0) were mixed, to which 5 mL of a 50 mM phosphate buffer (pH 7.0) containing 5.0% (w/v) acrylonitrile was further added. Next, the mixture was reacted while being shaken at 10° C. for 10 minutes. Then, bacterial cells were filtered and the amount of produced acrylamide was determined using gas chromatography.

<Analysis Conditions> analysis instrument: gas chromatograph GC-14D (Shimadzu Corporation)

detector: FID (detection at 200° C.)

column: 1 m glass column filled with PoraPak PS (column filler made by Waters Corp.)

column temperature: 190° C.

Nitrile hydratase activity was determined by conversion from the amount of acrylamide. Here, regarding nitrile hydratase activity, the amount of enzyme to produce 1 μmol of acrylamide per 1 minute is set as 1 U. Table 12 shows relative activities when the parent strain activity without amino-acid substitution was set at 1.0.

TABLE 12

| amino-acid substitution | name of plasmid | catalytic activity (relative value) |
|---|---|---|
| none (parent strain) | pSJ034 | 1.0 (comp. example) |
| Lβ37A | pSJ120 | 1.3 |
| Lβ37D | pSJ122 | 1.5 |
| Lβ37F | pSJ124 | 1.2 |
| Lβ37I | pSJ127 | 1.2 |
| Lβ37M | pSJ130 | 1.2 |
| Lβ37T | pSJ136 | 1.2 |
| Lβ37V | pSJ137 | 1.3 |

From the results above, enhanced enzymatic activity was confirmed in the enzyme in which an amino acid at position 37 in the β subunit was substituted with an amino acid selected from among alanine, valine, asparagine, threonine, phenylalanine, isoleucine and methionine.

Example 11

SDS-Polyacrylamide Gel Electrophoresis

Using a sonicator VP-300 (TAITEC Corporation), the bacterial-cell suspension prepared in example 2 was homogenized for 10 minutes while it was ice-cooled. Next, the bacterial-cell homogenate was centrifuged at 13500 rpm for 30 minutes and a cell-free extract was obtained from the supernatant. After the protein content of the cell extract was measured using a Bio-Rad protein assay kit, the cell extract was mixed with a polyacrylamide gel electrophoresis sample buffer (0.1 M Tris-HCl (pH 6.8), 4% w/v of SDS, 12% v/v of β mercaptoethanol, 20% v/v of glycerol, and a trace of bromophenol blue), and boiled for 5 minutes for denaturation. A 10% acrylamide gel was prepared, and denatured samples were applied to have an equivalent protein mass per one lane to conduct electrophoresis analysis.

As a result, since hardly any difference was observed in the band strength of nitrile hydratase in all the samples, the expressed amount of nitrile hydratase was found the same. Accordingly, enzymatic specific activity was found to be attributed to be the improved enzymatic activity.

Example 12

Preparation and Evaluation of Improved Nitrile Hydratase

Plasmid pFR005 below was used as a template plasmid substitute an amino acid at position 37 of the β subunit.

Namely, using the method in example 1, an improved nitrile hydratase with a substituted amino acid was prepared, and a transformant of *Rhodococcus rhodochrous* ATCC 12674 strain and its bacterial-cell suspension were obtained by the method in example 2. Further, the enzymatic activity was measured by the same method in example 3. The results are shown in Table 13.

TABLE 13

| name of plasmid | amino-acid substitution | catalytic activity (relative value) |
|---|---|---|
| pFR005 | Pβ17G, Sβ57K, Nβ167S, Tβ107K, Kβ114Y, Vβ219A | 1.0 (comp. example) |
| pER1121 | Pβ17G, Sβ57K, Nβ167S, Tβ107K, Kβ114Y, Vβ219A, Lβ37A | 1.6 |
| pER1140 | Pβ17G, Sβ57K, Nβ167S, Tβ107K, Kβ114Y, Vβ219A, Lβ37D | 1.3 |

From the results above, the amino-acid substitution according to the present invention applies not only to a wild-type nitrile hydratase but to a mutant nitrile hydratase to exhibit the same effects.

Example 13

Preparation of Improved Nitrile Hydratase

Using pSJ034 formed in preparation example 1, amino-acid substitution was conducted. The following composition of a reaction mixture, reaction conditions and primers shown in Table 14 were used for the PCR.

<Composition of PCR Reaction Mixture>

| | |
|---|---|
| sterile water | 20 μL |
| pSJ034 (1 ng/mL) | 1 μL |
| Forward primer (10 mM) | 2 μL |
| Reverse primer (10 mM) | 2 μL |
| PrimeSTAR MAX (2×) | 25 μL |
| total | 50 μL |

<PCR Reaction Conditions>

(98° C. for 10 sec, 55° C. for 5 sec, 72° C. for 90 sec)×30 cycles

<Primers>

TABLE 14

| substituted amino acid | name of primer | Sequence | SEQ ID NO |
|---|---|---|---|
| A | α83A-F | GGTGAGGCGGCACACCAAATTTCGGCG | 83 |
| | α83A-R | GTGTGCCGCCTCACCGGCATAGCCC | 84 |
| C | α83C-F | GGTGAGTGCGCACACCAAATTTCGGCG | 85 |
| | α83C-R | GTGTGCGCACTCACCGGCATAGCCC | 86 |
| D | α83D-F | GGTGAGGACGCACACCAAATTTCGGCG | 87 |
| | α83D-R | GTGTGCGTCCTCACCGGCATAGCCC | 88 |
| E | α83E-F | GGTGAGGAGGCACACCAAATTTCGGCG | 89 |
| | α83E-R | GTGTGCCTCCTCACCGGCATAGCCC | 90 |
| F | α83F-F | GGTGAGTTCGCACACCAAATTTCGGCG | 91 |
| | α83F-R | GTGTGCGAACTCACCGGCATAGCCC | 92 |
| G | α83G-F | GGTGAGGACGCACACCAAATTTCGGCG | 93 |
| | α83G-R | GTGTGCGCCCTCACCGGCATAGCCC | 94 |
| H | α83H-F | GGTGAGCACGCACACCAAATTTCGGCG | 95 |
| | α83H-R | GTGTGCGTGCTCACCGGCATAGCCC | 96 |
| M | α83M-F | GGTGAGATGGCACACCAAATTTCGGCG | 97 |
| | α83M-R | GTGTGCCATCTCACCGGCATAGCCC | 98 |
| P | α83P-F | GGTGAGCCGGCACACCAAATTTCGGCG | 99 |
| | α83P-R | GTGTGCCGGCTCACCGGCATAGCCC | 100 |
| S | α83S-F | GGTGAGTCCGCACACCAAATTTCGGCG | 101 |
| | α83S-R | GTGTGCGGACTCACCGGCATAGCCC | 102 |
| T | α83T-F | GGTGAGACCGCACACCAAATTTCGGCG | 103 |
| | α83T-R | GTGTGCGGTCTCACCGGCATAGCCC | 104 |

After the completion of PCR, 5 μL of the reaction mixture was subjected to 0.7% agarose gel electrophoresis and an amplified fragment of 11 kb was confirmed. Then, 1 μL of DpnI (provided with a kit) was added to the PCR reaction mixture and reacted at 37° C. for an hour to remove the template plasmid. The reacted mixture was purified using Wizard SV gel and PCR Clean-Up System (Promega), and JM109 was transformed using the purified PCR reaction product. Then, a plasmid DNA was extracted from the obtained culture using QIAprep Spin Miniprep Kit (Qiagen), and the base sequence of the nitrile hydratase was confirmed using an automated sequencer CEQ 8000 (Beckman Coulter, Inc.) Obtained plasmids were named as shown in Table 15.

TABLE 15

| name of plasmid | amino-acid substitution |
|---|---|
| pSJ127 | Qα83A |
| pSJ152 | Qα83C |
| pSJ153 | Qα83D |
| pSJ154 | Qα83E |
| pSJ155 | Qα83F |
| pSJ156 | Qα83G |
| pSJ157 | Qα83H |
| pSJ130 | Qα83M |
| pSJ132 | Qα83N |
| pSJ159 | Qα83P |
| pSJ161 | Qα83S |
| pSJ162 | Qα83T |

Example 14

Preparation of *Rhodococcus* Transformant

Cells of *Rhodococcus rhodochrous* strain ATCC 12674 in a logarithmic growth phase were collected using a centrifuge, washed three times with ice-cold sterile water, and suspended in the sterile water. Then, 1 μL of plasmid prepared in example 1 and 10 μL of the bacterial-cell suspension were mixed and ice-cooled. The DNA and the bacterial-cell suspension were supplied in a cuvette, and electric pulse treatment was conducted using an electroporation device, Gene Pulser (Bio-Rad Laboratories), under conditions of 2.0 kV and 200Ω. The electric-pulse processed mixture was let stand in an ice-cold condition for 10 minutes, and subjected to heat shock at 37° C. for 10 minutes. After 500 μL of an MYK culture medium (0.5% polypeptone, 0.3% Bacto yeast extract, 0.3% Bacto malt extract, 0.2% $K_2HPO_4$, 0.2% $KH_2PO_4$) was added and let stand at 30° C. for 5 hours, and applied onto an MYK agar culture medium containing 50 μg/mL kanamycin and incubated at 30° C. for 3 days. The obtained colony after incubating at 30° C. for 3 days was used as a transformant.

Each transformant obtained above were inoculated into an MYK culture medium (50 μg/mL kanamycin), and subjected to shaking culture at 30° C. for 2 days. Then, 1% culture was inoculated into a GGPK culture medium (1.5% glucose, 1% sodium glutamate, 0.1% yeast extract, 0.05% $K_2HPO_4$, 0.05% $KH_2P\ O_4$, 0.05% $Mg_2O_4.7H_2O$, 1% $CoCl_2$, 0.1% urea, 50 μg/mL kanamycin, pH 7.2), and shaking culture was performed at 30° C. for 3 days. Then, bacterial cells were collected by using a centrifuge and were washed with a 100 mM phosphate buffer (pH 7.0) to prepare a bacterial-cell suspension.

Example 15

Improved Nitrile Hydratase Activity

The nitrile hydratase activity in the obtained bacterial-cell suspension was measured by the following method: 0.2 mL of the bacterial-cell mixture and 4.8 mL of a 50 mM phosphate buffer (pH 7.0) were mixed, to which 5 mL of a 50 mM phosphate buffer (pH 7.0) containing 5.0% (w/v) acrylonitrile was further added. Next, the mixture was reacted while being shaken at 10° C. for 10 minutes. Then, bacterial cells were filtered and the amount of produced acrylamide was determined using gas chromatography.

<Analysis Conditions> analysis instrument: gas chromatograph GC-14B (Shimadzu Corporation)

detector: FID (detection at 200° C.)

column: 1 m glass column filled with PoraPak PS (column filler made by Waters Corp.)

column temperature: 190° C.

Nitrile hydratase activity was determined by conversion from the amount of acrylamide. Here, regarding nitrile hydratase activity, the amount of enzyme to produce 1 μmol of acrylamide per 1 minute is set as 1 U. Table 16 shows relative activities when the parent strain activity without amino-acid substitution was set at 1.0.

TABLE 16

| name of plasmid | amino-acid substitution | catalytic activity (relative value) |
|---|---|---|
| pSJ034 | none (parent strain) | 1.0 (comp. example) |
| pSJ127 | Qα83A | 5.3 |
| pSJ152 | Qα83C | 3.7 |
| pSJ153 | Qα83D | 1.9 |
| pSJ154 | Qα83E | 1.2 |
| pSJ155 | Qα83F | 1.8 |
| pSJ156 | Qα83G | 4.4 |
| pSJ157 | Qα83H | 1.9 |
| pSJ130 | Qα83M | 2.3 |
| pSJ132 | Qα83N | 5.7 |
| pSJ159 | Qα83P | 1.5 |
| pSJ161 | Qα83S | 5.8 |
| pSJ162 | Qα83T | 3.8 |

From the results above, enhanced enzymatic activity was confirmed in the enzyme in which an amino acid at position 83 in the α subunit was substituted with an amino acid selected from among alanine, aspartic acid, phenylalanine, histidine, methionine and asparagine.

Example 16

Preparation and Evaluation of Improved Nitrile Hydratase

Plasmid pFR005 formed below was used as a template plasmid to substitute an amino acid at position 83 of the α subunit.

Namely, using the method in example 1, an improved nitrile hydratase with a substituted amino acid was prepared, and a transformant of *Rhodococcus rhodochrous* strain ATCC 12674 and its bacterial-cell suspension were obtained by the method in example 2. Further, the enzymatic activity was measured by the same method in example 3. The results are shown in Table 17.

TABLE 17

| name of plasmid | amino-acid substitution | catalytic activity (relative value) |
|---|---|---|
| pFR005 | Pβ17G, Sβ57K, Tβ107K, Kβ114Y, Nβ167S, Vβ219A | 1.0 (comp. example) |
| pER1127 | Pβ17G, Sβ57K, Tβ107K, Kβ114Y, Nβ167S, Vβ219A, Qα83A | 5.1 |
| pER1129 | Pβ17G, Sβ57K, Tβ107K, Kβ114Y, Nβ167S, Vβ219A, Qα37L | 1.9 |
| pER1130 | Pβ17G, Sβ57K, Tβ107K, Kβ114Y, Nβ167S, Vβ219A, Qα83M | 2.7 |
| pER1132 | Pβ17G, Sβ57K, Tβ107K, Kβ114Y, Nβ167S, Vβ219A, Qα37N | 4.8 |

From the results above, the amino-acid substitution according to the present invention applies not only to a wild-type nitrie hydratase but to a mutant nitrile hydratase to exhibit the same effects.

Example 17

Preparation of Transformant Containing Nitrile Hydratase Derived from *Rhodococcus Rhodochrous* M8 Strain (Hereinafter Referred to as M8 Strain)

(1) Preparation of Chromosomal DNA from M8 Strain

The M8 strain (SU 1731814) is obtained from Russian Institute of Microorganism Biochemistry and Physiology (VKPM S-926). In a 100 mL MYK culture medium (0.5% polypeptone, 0.3% Bacto yeast extract, 0.3% Bacto malt extract, 0.2% $K_2HPO_4$, 0.2% $KH_2PO_4$, pH 7.0), the M8 strain was subjected to shaking culture at 30° C. for 72 hours. The culture mixture was centrifuged, and the collected bacterial cells were suspended in 4 mL of Saline-EDTA solution (0.1 M EDTA, 0.15 M NaCl, pH 8.0). Then, 8 mg of lysozyme was added to the suspension, which was shaken at 37° C. for 1~2 hours and was frozen at −20° C.

Next, 10 mL of Tris-SDS solution (1% SDS, 0.1M NaCl, 0.1 M Tris-HCl (pH 9.0)) was added to the suspension while the suspension was gently shaken. Proteinase K (Merck KGaA) was further added (final concentration of 0.1 mg) and shaken at 37° C. for 1 hour. Next, an equivalent volume of TE saturated phenol was added, agitated (TE: 10 mM Tris-HCl, 1 mM EDTA (pH 8.0)) and then centrifuged. The supernatant was collected, a double volume of ethanol was added and DNA strands were wrapped around a glass rod. Then, the phenol was removed through centrifugation by successively adding 90%, 80%, and 70% ethanol.

Next, the DNA was dissolved in a 3 mL TE buffer, to which a Ribonuclease A solution (processed at 100° C. for 15 minutes) was added to have a 10 μg/mL concentration and shaken at 37° C. for 30 minutes. Proteinase K (Merck KGaA) was further added and shaken at 37° C. for 30 minutes. After an equivalent volume of TE saturated phenol was added and centrifuged, the mixture was separated into upper and lower layers.

An equivalent volume of TE saturated phenol was further added to the upper layer and centrifuged to separate into upper and lower layers. Such a process was repeated. Then, an equivalent volume of chloroform (containing 4% isoamyl alcohol) was added, centrifuged and the upper layer was collected. Then, a double volume of ethanol was added and the DNA strands were collected by wrapping them around a glass rod. Accordingly, chromosomal DNA was obtained.

(2) Using PCR, Preparation of Improved Nitrile Hydratase from Chromosomal DNA Derived from the M8 Strain The nitrile hydratase derived from the M8 strain is described in a non-patent publication (Veiko, V. P. et al., "Cloning, Nucleotide Sequence of Nitrile Hydratase Gene from *Rhodococcus rhodochrous* M8," Russian Biotechnology (Mosc.) 5, 3-5 (1995)). The sequences of β subunit and α subunit are respectively identified as SEQ ID NOs: 17 and 18. Based on the sequence information, primers of SEQ ID NOs: 115 and 116 in the sequence listing were synthesized and PCR was performed using the chromosomal DNA prepared in step (1) above as a template.

<Composition of PCR Reaction Mixture>

| | |
|---|---|
| sterile water | 20 μL |
| template DNA (chromosomal DNA) | 1 μL |
| primer M8-1 (10 mM) | 2 μL |
| primer M8-2 (10 mM) | 2 μL |
| PrimeSTAR MAX (2×) | 25 μL |
| total | 50 μL |

<Primers>

```
M8-1:
                                    (SEQ ID NO: 115)
GGTCTAGAATGGATGGTATCCACGACACAGGC

M8-2:
                                    (SEQ ID NO: 116)
CCCCTGCAGGTCAGTCGATGATGGCCATCGATTC
```

<PCR Reaction Conditions>

(98° C. for 10 sec, 55° C. for 5 sec, 72° C. for 30 sec)×30 cycles

After completion of PCR, 5 μL of the reaction mixture was subjected to 0.7% agarose gel electrophoresis (0.7 wt. % Agarose I, made by Dojin Chemical Co., Ltd.) and an amplified fragment of 1.6 kb was detected. The reacted mixture was purified using Wizard SV gel and PCR Clean-Up System (Promega KK).

Next, the collected PCR product was coupled with a vector (pUC118/Hinc II site) using a ligation kit (made by Takara Shuzo Co., Ltd.) so that competent cells of *E. coli* JM109 were transformed using the reaction mixture. A few clones from the obtained transformant colonies were inoculated into 1.5 mL of an LB-Amp culture medium, and subjected to shaking culture at 37° C. for 12 hours. After incubation was finished, the bacterial cells were collected from the culture through centrifugation. A plasmid DNA was extracted from the collected bacterial cells using QIAprep Spin Miniprep Kit (Qiagen). The base sequence of nitrile hydratase in the obtained plasmid DNA was confirmed using a sequencing kit and automated sequencer CEQ 8000 (Beckman Coulter, Inc.).

Next, the obtained plasmid DNA was cleaved at restriction enzyme XbaI and Sse8387I, and subjected to 0.7% agarose gel electrophoresis so as to collect nitrile hydratase gene fragments (1.6 kb), which were then introduced into XbaI-Sse8387I site of plasmid pSJ042. The obtained plasmid was named pSJ-NO1A. Here, pSJ042 as a plasmid capable of expressing nitrile hydratase in *Rhodococcus* J1 strain was prepared by a method described in JP publication 2008~154552. Plasmid pSJ023 used for preparation of pSJ042 is registered as transformant ATCC 12674/pSJ023 (FERM BP-6232) at the International Patent Organism Depositary, National Institute of Advanced Industrial Science and Technology (Central 6, 1-1-1 Higashi, Tsukuba, Ibaraki), deposited Mar. 4, 1997.

Example 18

Preparation and Evaluation of Improved Nitrile Hydratase

Using plasmid pSJ-NO1A obtained in example 5, the amino acid at position 83 of the α subunit was substituted. The same method as in example 1 was employed for amino-acid substitution to prepare an improved nitrile hydratase. Next, using the same method as in example 2, a transformant of *Rhodococcus rhodochrous* ATCC 12674 strain and its bacterial-cell suspension were prepared. Then, the enzymatic activity was measured by the same method as in example 4. The results are shown in Table 18.

TABLE 18

| name of plasmid | amino-acid substitution | catalytic activity (relative value) |
|---|---|---|
| pSJ-N01A | none (parent strain) | 1.0 (comp. example) |
| pSJR17 | Qα83M | 6.9 |

From the results above, pSJR17 in which the amino acid at position 83 of the α subunit was substituted with methionine was found to have an enhanced enzymatic activity the same as in example 4.

Example 19

Preparation of Improved Nitrile Hydratase

Using plasmid pSJ034 formed in preparation example 1, amino-acid substitution was conducted. The following composition of a reaction mixture, reaction conditions and primers were used for the PCR.

<Composition of PCR Reaction Mixture>

| | |
|---|---|
| sterile water | 20 μL |
| pSJ034 (1 ng/mL) | 1 μL |
| Forward primer (10 mM) | 2 μL |
| Reverse primer (10 mM) | 2 μL |
| PrimeSTAR MAX (2×) | 25 μL |
| total | 50 μL |

<PCR Reaction Conditions>

(98° C. for 10 sec, 55° C. for 5 sec, 72° C. for 90 sec)×30 cycles

<Primers> Saturation Mutagenesis for α82

```
α82RM-F:
                                  (SEQ ID NO: 129)
ATGCCGGTNNSCAGGCACACCAAATTT

α82RM-R:
                                  (SEQ ID NO: 130)
TGTGCCTGSNNACCGGCATAGCCCAAT
```

After the completion of PCR, 5 μL of the reaction mixture was subjected to 0.7% agarose gel electrophoresis and an amplified fragment of 1 kb was confirmed. Then, 1 μL of DpnI (provided with a kit) was added to the PCR reaction mixture and reacted at 37° C. for an hour to remove the template plasmid. The reacted mixture was purified using Wizard SV gel and PCR Clean-Up System (Promega), and JM109 was transformed using the purified PCR reaction product. Then, a plasmid DNA was extracted from the obtained culture using QIAprep Spin Miniprep Kit (Qiagen), and the base sequence of the nitrile hydratase was confirmed using an automated sequencer CEQ 8000 (Beckman Coulter, Inc.) Obtained plasmids were named as shown in Table 19.

TABLE 19

| name of plasmid | amino-acid substitution |
|---|---|
| pSJ173 | Eα82C |
| pSJ174 | Eα82F |
| pSJ175 | Eα82H |
| pSJ176 | Eα82I |
| pSJ177 | Eα82K |
| pSJ178 | Eα82M |
| pSJ179 | Eα82Q |
| pSJ180 | Eα82R |
| pSJ181 | Eα82T |
| pSJ182 | Eα82Y |

Example 20

Preparation of *Rhodococcus* Transformant

Cells of *Rhodococcus rhodochrous* ATCC 12674 strain in a logarithmic growth phase were collected using a centrifuge, washed three times with ice-cold sterile water, and suspended in the sterile water. Then, 1 μL of plasmid prepared in example 2 and 10 μL of the bacterial-cell suspension were mixed and ice-cooled. The DNA and the bacterial-cell suspension were supplied in a cuvette, and electric pulse treatment was conducted using an electroporation device, Gene Pulser (Bio-Rad Laboratories), under conditions of 2.0 kV and 200). The electric-pulse processed mixture was let stand in an ice-cold condition for 10 minutes, and subjected to heat shock at 37° C. for 10 minutes. After 500 μL of an MYK culture medium (0.5% polypeptone, 0.3% Bacto yeast extract, 0.3% Bacto malt extract, 0.2% $K_2HPO_4$, 0.2% $KH_2PO_4$) was added and let stand at 30° C. for 5 hours, and applied onto an MYK agar culture medium containing 50 μg/mL kanamycin and incubated at 30° C. for 3 days. The obtained colony after incubating at 30° C. for 3 days was used as a transformant.

Each transformant obtained above was inoculated into an MYK culture medium (50 kanamycin), subjected to shaking culture at 30° C. for 2 days. Then, 1% culture was inoculated into a GGPK culture medium (1.5% glucose, 1% sodium glutamate, 0.1% yeast extract, 0.05% $K_2HPO_4$, 0.05% $KH_2PO_4$, 0.05% $Mg_2O_4$'$7H_2O$, 1% $CoCl_2$, 0.1% urea, 50 μg/mL kanamycin, pH 7.2), and subjected to shaking culture at 30° C. for 3 days. Then, bacterial cells were collected by using a centrifuge and were washed with a 100 mM phosphate buffer (pH 7.0) to prepare a bacterial-cell suspension.

Example 21

Improved Nitrile Hydratase Activity

The nitrile hydratase activity in the obtained bacterial-cell suspension was measured by the following method.

After 0.2 mL of the bacterial-cell mixture and 4.8 mL of a 50 mM phosphate buffer (pH 7.0) were mixed, 5 mL of a 50 mM phosphate buffer (pH 7.0) containing 5.0% (w/v) acrylonitrile was further added, and the mixture was reacted while being shaken at 10° C. for 10 minutes. Then, bacterial cells were filtered and the amount of produced acrylamide was determined by gas chromatography.

<Analysis Conditions> analysis instrument: gas chromatograph GC2014 (Shimadzu Corporation)

detector: FID (detection at 200° C.)

column: 1 m glass column filled with PoraPak PS (column filler made by Waters Corp.)

column temperature: 190° C.

Nitrile hydratase activity was determined by conversion from the amount of acrylamide. Here, regarding nitrile hydratase activity, the amount of enzyme to produce 1 μmol of acrylamide per 1 minute is set as 1 U. Table 20 shows relative activities when the parent strain activity without amino-acid substitution was set at 1.0.

TABLE 20

| name of plasmid | amino-acid substitution | catalytic activity (relative value) |
|---|---|---|
| pSJ042 | none (parent strain) | 1.0 (comp. example) |
| pSJ173 | Eα82C | 2.6 |
| pSJ174 | Eα82F | 4.3 |
| pSJ175 | Eα82H | 1.3 |
| pSJ176 | Eα82I | 3.6 |
| pSJ177 | Eα82K | 4.2 |
| pSJ178 | Eα82M | 3.6 |
| pSJ179 | Eα82Q | 2.3 |
| pSJ180 | Eα82R | 4.2 |
| pSJ181 | Eα82T | 1.2 |
| pSJ182 | Eα82Y | 2.1 |

From the results above, enhanced enzymatic activity was confirmed in the enzyme in which an amino acid at position 82 in the α subunit was substituted with an amino acid selected from among cysteine, phenylalanine, histidine, isoleucine, lysine, methionine, glutamine, arginine, threonine and tyrosine.

Example 22

SDS-Polyacrylamide Gel Electrophoresis

Using a sonicator VP-300 (TAITEC Corporation), the bacterial-cell suspension prepared in example 3 was homogenized for 10 minutes while being ice-cooled. Next, the bacterial-cell homogenate was centrifuged at 13500 rpm for 30 minutes and a cell-free extract was obtained from the supernatant. After the protein content of the cell extract was measured using a Bio-Rad protein assay kit, the cell extract was mixed with a polyacrylamide gel electrophoresis sample buffer (0.1 M Tris-HCl (pH 6.8), 4% w/v SDS, 12% v/v β mercaptoethanol, 20% v/v glycerol, and a trace of bromophenol blue), and boiled for 5 minutes for denaturation. A 10% acrylamide gel was prepared, and denatured samples were applied to have an equivalent protein mass per one lane to conduct electrophoresis analysis.

As a result, since hardly any difference was observed in the band strength of nitrile hydratase in all the samples, the expressed amount of nitrile hydratase was found the same. Accordingly, enzymatic specific activity was found to be attributed to the improved enzymatic activity.

Example 23

Preparation of Improved Nitrile Hydratase

Using plasmid pSJ034 formed in preparation example 1, amino-acid substitution was conducted. The following composition of a reaction mixture, reaction conditions and primers were used for the PCR.

<Composition of PCR Reaction Mixture>

| | |
|---|---|
| sterile water | 20 μL |
| pSJ034 (1 ng/mL) | 1 μL |
| Forward primer (10 mM) | 2 μL |
| Reverse primer (10 mM) | 2 μL |
| PrimeSTAR MAX (2×) | 25 μL |
| total | 50 μL |

<PCR Reaction Conditions>

(98° C. for 10 sec, 55° C. for 5 sec, 72° C. for 90 sec)×30 cycles

<Primers> saturation mutagenesis primer for α85

```
α85RM-F:
                                    (SEQ ID NO: 133)
CAGGCANNSCAAATTTCGGCGGTCTTC

α85RM-R:
                                    (SEQ ID NO: 134)
AATTTGSNNTGCCTGCTCACCGGCATA
```

After the completion of PCR, 5 μL of the reaction mixture was subjected to 0.7% agarose gel electrophoresis and an amplified fragment of 1 kb was confirmed. Then, 1 μL of DpnI (provided with a kit) was added to the PCR reaction mixture and reacted at 37° C. for an hour to remove the template plasmid. The reacted mixture was purified using Wizard SV gel and PCR Clean-Up System (Promega), and JM109 was transformed using the purified PCR reaction product. Then, a plasmid DNA was extracted from the obtained culture using QIAprep Spin Miniprep Kit (Qiagen), and the base sequence of the nitrile hydratase was confirmed using an automated sequencer CEQ 8000 (Beckman Coulter, Inc.) Obtained plasmids were named as shown in Table 21.

TABLE 21

| name of plasmid | amino-acid substitution |
|---|---|
| pSJ165 | Hα85C |
| pSJ166 | Hα85E |
| pSJ167 | Hα85F |
| pSJ168 | Hα85I |
| pSJ169 | Hα85N |
| pSJ170 | Hα85Q |
| pSJ171 | Hα85S |
| pSJ172 | Hα85Y |

Example 24

Preparation of *Rhodococcus* Transformant

Cells of *Rhodococcus rhodochrous* ATCC 12674 strain in a logarithmic growth phase were collected using a centrifuge, washed three times with ice-cold sterile water, and suspended in the sterile water. Then, 1 μL of plasmid prepared in example 2 and 10 μL of the bacterial-cell suspension were mixed and ice-cooled. The DNA and the bacterial-cell suspension were supplied in a cuvette, and electric pulse treatment was conducted using an electroporation device, Gene Pulser (Bio-Rad Laboratories), under conditions of 2.0 kV and 200Ω. The electric-pulse processed mixture was let stand in an ice-cold condition for 10 minutes, and subjected to heat shock at 37° C. for 10 minutes. After 500 μL of an MYK culture medium (0.5% polypeptone, 0.3% Bacto yeast extract, 0.3% Bacto malt extract, 0.2% $K_2HPO_4$, 0.2% $KH_2PO_4$) was added and let stand at 30° C. for 5 hours, and applied onto an MYK agar culture medium containing 50 μg/mL kanamycin and incubated at 30° C. for 3 days. The obtained colony after incubating at 30° C. for 3 days was used as a transformant.

Each transformant obtained above was inoculated into an MYK culture medium (50 μg/mL kanamycin), and subjected to shaking culture at 30° C. for 2 days. Then, 1% culture was each inoculated into a GGPK culture medium (1.5% glucose, 1% sodium glutamate, 0.1% yeast extract, 0.05% $K_2HPO_4$, 0.05% $KH_2PO_4$, 0.05% $Mg_2O_4.7H_2O$, 1% $CoCl_2$, 0.1% urea, 50 μg/mL kanamycin, pH 7.2), and shaking culture was performed at 30° C. for 3 days. Bacterial cells were collected by using a centrifuge and were washed with a 100 mM phosphate buffer (pH 7.0) to prepare a bacterial-cell suspension.

Example 25

Improved Nitrile Hydratase Activity

The nitrile hydratase activity of the bacterial-cell suspension was measure as follows.

After 0.2 mL of the bacterial-cell mixture and 4.8 mL of a 50 mM phosphate buffer (pH 7.0) were mixed, 5 mL of a 50 mM phosphate buffer (pH 7.0) containing 5.0% (w/v) acrylonitrile was further added, and the mixture was reacted while being shaken at 10° C. for 10 minutes. Then, bacterial cells were filtered and the amount of produced acrylamide was determined by gas chromatography.

<Analysis Conditions> analysis instrument: gas chromatograph GC2014 (Shimadzu Corporation)

detector: FID (detection at 200° C.)

column: 1 m glass column filled with PoraPak PS (column filler made by Waters Corp.)

column temperature: 190° C.

Nitrile hydratase activity was determined by conversion from the amount of acrylamide. Here, regarding nitrile hydratase activity, the amount of enzyme to produce 1 μmol of acrylamide per 1 minute is set as 1 U. Table 22 shows relative activities when the parent strain activity without amino-acid substitution was set at 1.0.

TABLE 22

| name of plasmid | amino-acid substitution | catalytic activity (relative value) |
|---|---|---|
| pSJ042 | none (parent strain) | 1.0 (comp. example) |
| pSJ165 | Hα85C | 1.5 |
| pSJ166 | Hα85E | 1.9 |
| pSJ167 | Hα85F | 1.8 |
| pSJ168 | Hα85I | 2.1 |
| pSJ169 | Hα85N | 2.3 |
| pSJ170 | Hα85Q | 2.1 |
| pSJ171 | Hα85S | 2.5 |
| pSJ172 | Hα85Y | 1.5 |

From the results above, enhanced enzymatic activity was confirmed in the enzyme in which an amino acid at position 85 in the α subunit was substituted with an amino acid selected from among cysteine, glutamic acid, phenylalanine, isoleucine, asparagine, glutamine, serine and tyrosine.

Example 26

SDS-Polyacrylamide Gel Electrophoresis

Using a sonicator VP-300 (TAITEC Corporation), the bacterial-cell suspension prepared in example 3 was homogenized for 10 minutes while being ice-cooled. Next, the bacterial-cell homogenate was centrifuged at 13500 rpm for 30 minutes and a cell-free extract was obtained from the supernatant. After the protein content of the cell extract was measured using a Bio-Rad protein assay kit, the cell extract was mixed with a polyacrylamide gel electrophoresis sample buffer (0.1 M Tris-HCl (pH 6.8), 4% w/v SDS, 12% v/v β mercaptoethanol, 20% v/v glycerol, and a trace of bromophenol blue), and boiled for 5 minutes for denaturation. A 10% acrylamide gel was prepared, and denatured samples were applied to have an equivalent protein mass per one lane to conduct electrophoresis analysis.

As a result, since hardly any difference was observed in the band strength of nitrile hydratase in all the samples, the expressed amount of nitrile hydratase was found to be the same. Accordingly, the enzymatic specific activity was found to be attributed to the improved enzymatic activity.

POTENTIAL INDUSTRIAL APPLICABILITY

According to the present invention, a novel improved (mutant) nitrile hydratase is provided with enhanced catalytic activity. Such an improved nitrile hydratase with enhanced catalytic activity is very useful to produce amide compounds.

According to the present invention, a nitrile hydratase is obtained from DNA encoding the improved nitrile hydratase above, a recombinant vector containing the DNA, a transformant containing the recombinant vector, and a culture of the transformant, and a method for producing such a nitrile hydratase is also provided. Moreover, a method for producing an amide compound using the protein (improved nitrile hydratase), the culture or the processed product of the culture is provided according to the present invention.

According to the present invention, a novel improved (mutant) nitrile hydratase is provided with enhanced catalytic activity. Such an improved nitrile hydratase with enhanced catalytic activity is very useful to produce amide compounds.

According to the present invention, a nitrile hydratase is obtained from genomic DNA encoding the improved nitrile hydratase above, a recombinant vector containing the genomic DNA, a transformant containing the recombinant vector, and a culture of the transformant, and a method for producing such a nitrile hydratase is also provided. Moreover, a method for producing an amide compound using the protein (improved nitrile hydratase), the culture or the processed product of the culture is provided according to the present invention.

Accession Numbers

*Rhodococcus rhodochrous* J1 strain is internationally registered under accession number "FERM BP-1478" at the International Patent Organism Depositary, National Institute of Advanced Industrial Science and Technology, (Central 6, 1-1-1 Higashi, Tsukuba, Ibaraki), deposited Sep. 18, 1987.

In addition, pSJ023 is a transformant "*R. rhodochrous* ATCC 12674/pSJ023," and is internationally registered under accession number FERM BP-6232 at the International Patent Organism Depositary, National Institute of Advanced Industrial Science (Central 6, 1-1-1 Higashi, Tsukuba, Ibaraki), deposited Mar. 4, 1997.

DESCRIPTION OF SEQUENCE LISTING

SEQ ID NO: 1 base sequence of β subunit derived from *Rhodococcus rhodochrous* J1 strain (FERM BP-1478)
SEQ ID NO: 2 amino-acid sequence of β subunit derived from *Rhodococcus rhodochrous* J1 strain (FERM BP-1478)
SEQ ID NO: 3 base sequence of α subunit derived from *Rhodococcus rhodochrous* J1 strain (FERM BP-1478)
SEQ ID NO: 4 amino-acid sequence of α subunit derived from *Rhodococcus rhodochrous* J1 strain (FERM BP-1478)
SEQ ID NO: 5 amino-acid sequence of β subunit in *Rhodococcus rhodochrous* M8 (SU 1731814)
SEQ ID NO: 6 amino-acid sequence of β subunit in *Rhodococcus ruber* TH
SEQ ID NO: 7 amino-acid sequence of β subunit in *Rhodococcus pyridinivorans* MW33 (VKM Ac-1515D)
SEQ ID NO: 8 amino-acid sequence of β subunit in *Rhodococcus pyridinivorans* S85-2
SEQ ID NO: 9 amino-acid sequence of β subunit in *Rhodococcus pyridinivorans* MS-38
SEQ ID NO: 10 amino-acid sequence of β subunit in *Nocardia* sp. JBRs
SEQ ID NO: 11 amino-acid sequence of β subunit in *Nocardia* sp. YS-2002
SEQ ID NO: 12 amino-acid sequence of β subunit in *Rhodococcus rhodochrous* ATCC 39384
SEQ ID NO: 13 β48C-F primer
SEQ ID NO: 14 β48C-R primer
SEQ ID NO: 15 β48D-F primer
SEQ ID NO: 16 β48D-R primer
SEQ ID NO: 17 β48E-F primer
SEQ ID NO: 18 β48E-R primer
SEQ ID NO: 19 β48H-F primer
SEQ ID NO: 20 β48H-R primer
SEQ ID NO: 21 β48I-F primer
SEQ ID NO: 22 β48I-R primer
SEQ ID NO: 23 β48K-F primer
SEQ ID NO: 24 β48K-R primer
SEQ ID NO: 25 β48M-F primer
SEQ ID NO: 26 β48M-R primer
SEQ ID NO: 27 β48N-F primer
SEQ ID NO: 28 β48N-R primer
SEQ ID NO: 29 β48P-F primer
SEQ ID NO: 30 β48P-R primer
SEQ ID NO: 31 β48Q-F primer
SEQ ID NO: 32 β48Q-R primer
SEQ ID NO: 33 β48S-F primer
SEQ ID NO: 34 β48S-R primer
SEQ ID NO: 35 β48T-F primer
SEQ ID NO: 36 β48T-R primer
SEQ ID NO: 37 amino-acid sequence of β subunit in nitrile hydratase derived from M8 strain
SEQ ID NO: 38 amino-acid sequence of α subunit in nitrile hydratase derived from M8 strain
SEQ ID NO: 39 amino-acid sequence of activator in nitrile hydratase derived from M8 strain
SEQ ID NO: 40 M8-1 primer
SEQ ID NO: 41 M8-2 primer
SEQ ID NO: 42 amino-acid sequence of β subunit in uncultured bacterium SP1
SEQ ID NO: 43 amino-acid sequence of β subunit in uncultured bacterium BD2
SEQ ID NO: 44 amino-acid sequence of β subunit in Comamonas testosterone
SEQ ID NO: 45 amino-acid sequence of β subunit in *Geobacillus thermoglucosidasius* Q6
SEQ ID NO: 46 amino-acid sequence of β subunit in *Pseudonocardia thermophila* JCM 3095
SEQ ID NO: 47 amino-acid sequence of β subunit in *Rhodococcus rhodochrous* Cr4
SEQ ID NO: 48 amino-acid sequence of cysteine cluster of α subunit in iron-containing nitrile hydratase
SEQ ID NO: 49 amino-acid sequence in cysteine cluster of α subunit in cobalt-containing nitrile hydratase
SEQ ID NO: 50 predetermined amino-acid sequence to be used in the present invention
SEQ ID NO: 51 amino-acid sequence of β subunit related to the present invention
SEQ ID NO: 52 amino-acid sequence of β subunit in *Rhodococcus ruber* RH (CN 101463358)
SEQ ID NO: 53 base sequence of nitrile hydratase J1D
SEQ ID NO: 54 base sequence of nitrile hydratase 203
SEQ ID NO: 55 base sequence of nitrile hydratase 414
SEQ ID NO: 56 base sequence of nitrile hydratase 855
SEQ ID NO: 57 base sequence of the α subunit in nitrile hydratase D2
SEQ ID NO: 58 base sequence of nitrile hydratase 005
SEQ ID NO: 59 base sequence of nitrile hydratase 108A
SEQ ID NO: 60 base sequence of nitrile hydratase 211
SEQ ID NO: 61 base sequence of nitrile hydratase 306A
SEQ ID NO: 62 base sequence of a PCR fragment containing a primer sequence at both terminal of *Rhodococcus rhodochrous* M8
SEQ ID NO: 63 β17RM-F primer
SEQ ID NO: 64 β17RM-R primer SEQ ID NO: 65 NH-19 primer
SEQ ID NO: 66 NH-20 primer
SEQ ID NO: 67 β37A-F primer
SEQ ID NO: 68 β37A-R primer
SEQ ID NO: 69 β37D-F primer
SEQ ID NO: 70 β37D-R primer
SEQ ID NO: 71 β37F-F primer
SEQ ID NO: 72 β37F-R primer
SEQ ID NO: 73 β37I-F primer
SEQ ID NO: 74 β37I-R primer
SEQ ID NO: 75 β37M-F primer
SEQ ID NO: 76 β37M-R primer
SEQ ID NO: 77 β37T-F primer
SEQ ID NO: 78 β37T-R primer
SEQ ID NO: 79 β37V-F primer
SEQ ID NO: 80 β37V-R primer
SEQ ID NO: 81 predetermined amino-acid sequence to be used in the present invention
SEQ ID NO: 82 amino-acid sequence of β subunit related to the present invention
SEQ ID NO: 83 α83A-F primer
SEQ ID NO: 84 α83A-R primer
SEQ ID NO: 85 α83C-F primer
SEQ ID NO: 86 α83C-R primer
SEQ ID NO: 87 α83D-F primer
SEQ ID NO: 88 α83D-R primer
SEQ ID NO: 89 α83E-F primer
SEQ ID NO: 90 α83E-R primer
SEQ ID NO: 91 α83F-F primer
SEQ ID NO: 92 α83F-R primer
SEQ ID NO: 93 α83G-F primer
SEQ ID NO: 94 α83G-R primer
SEQ ID NO: 95 α83H-F primer
SEQ ID NO: 96 α83H-R primer
SEQ ID NO: 97 α83M-F primer
SEQ ID NO: 98 α83M-R primer
SEQ ID NO: 99 α83P-F primer
SEQ ID NO: 100 α83P-R primer
SEQ ID NO: 101 α83S-F primer
SEQ ID NO: 102 α83S-R primer
SEQ ID NO: 103 α83T-F primer
SEQ ID NO: 104 α83T-R primer
SEQ ID NO: 105 amino-acid sequence of α subunit in *Rhodococcus rhodochrous* M8 (SU 1731814)
SEQ ID NO: 106 amino-acid sequence of α subunit in *Rhodococcus ruber* TH
SEQ ID NO: 107 amino-acid sequence of α subunit in *Rhodococcus pyridinivorans* MW33 (VKM Ac-1515D)
SEQ ID NO: 108 amino-acid sequence of α subunit in *Rhodococcus pyridinivorans* S85-2
SEQ ID NO: 109 amino-acid sequence of α subunit in *Nocardia* sp. JBRs
SEQ ID NO: 110 amino-acid sequence of α subunit in *Nocardia* sp. YS-2002
SEQ ID NO: 111 amino-acid sequence of α subunit in uncultured bacterium BD2
SEQ ID NO: 112 amino-acid sequence of α subunit in uncultured bacterium SP1
SEQ ID NO: 113 amino-acid sequence of α subunit in *Pseudonocardia thermophila JCM* 3095
SEQ ID NO: 114 amino-acid sequence of α subunit in *Rhodococcus rhodochrous* Cr4
SEQ ID NO: 115 M8-1 primer
SEQ ID NO: 116 M8-2 primer
SEQ ID NO: 117 amino-acid sequence in a cysteine cluster of α subunit in iron-containing nitrile hydratase
SEQ ID NO: 118 amino-acid sequence in cysteine cluster of α subunit in cobalt-containing nitrile hydratase
SEQ ID NO: 119 predetermined amino-acid sequence to be used in the present invention
SEQ ID NO: 120 amino-acid sequence of α subunit related to the present invention
SEQ ID NO: 121 amino-acid sequence of α subunit in *Rhodococcus pyridinivorans* MS-38
SEQ ID NO: 122 amino-acid sequence of α subunit in *Rhodococcus rhodochrous* ATCC 39384
SEQ ID NO: 123 amino-acid sequence of α subunit in *Sinorhizobium medicae* WSM419
SEQ ID NO: 124 amino-acid sequence of α subunit in *Geobacillus thermoglucosidasius* Q6
SEQ ID NO: 125 amino-acid sequence of α subunit in Comamonas testosterone
SEQ ID NO: 126 amino-acid sequence of α subunit in *Rhodococcus ruber* RH (CN 101463358)
SEQ ID NO: 127 α83N-F primer
SEQ ID NO: 128 α83N-R primer
SEQ ID NO: 129 α82RM-F primer
SEQ ID NO: 130 α82RM-R primer
SEQ ID NO: 131 amino-acid sequence of α subunit related to the present invention
SEQ ID NO: 132 predetermined amino-acid sequence to be used in the present invention
SEQ ID NO: 133 α85RM-F primer
SEQ ID NO: 134 α85RM-R primer
SEQ ID NO: 135 amino-acid sequence of α subunit related to the present invention
SEQ ID NO: 136 predetermined amino-acid sequence to be used in the present invention

---

What is claimed is:

1. A modified *Rhodococcus* bacterial or *Nocardia* bacterial nitrile hydratase, comprising in the β subunit, an amino-acid sequence as shown in SEQ ID NO: 81:

$WEX_1X_2X_3X_4X_5X_6X_7X_8X_9X_{10}X_{11}X_{12}X_{13}X_{14}X_{15}X_{16}X_{17}X_{18}D$ (SEQ ID NO: 81), wherein W is tryptophan, E is glutamic acid, D is aspartic acid, $X_1$~$X_6$, $X_8$~$X_{13}$ and $X_{15}$~$X_{18}$ each independently indicate any amino-acid residue, $X_7$ is an amino acid selected from the group consisting of alanine, valine, aspartic acid, threonine, phenylalanine, isoleucine and methionine, and $X_{14}$ is glycine.

2. The modified *Rhodococcus* bacterial or *Nocardia* bacterial nitrile hydratase according to claim 1, wherein $X_1$ is G (glycine), $X_2$ is R (arginine), $X_3$ is T (threonine), $X_4$ is L (leucine), $X_5$ is S (serine), $X_6$ is I (isoleucine), $X_8$ is T (threonine), $X_9$ is W (tryptophan), $X_{10}$ is M (methionine), $X_{11}$ is H (histidine), $X_{12}$ is L (leucine), $X_{13}$ is K (lysine), and $X_{14}$ is G (glycine) in SEQ ID NO: 81.

3. The modified *Rhodococcus* bacterial or *Nocardia* bacterial nitrile hydratase according to claim 1, further comprising an amino-acid sequence in SEQ ID NO: 82 comprising the amino-acid sequence in SEQ ID NO: 81.

4. A DNA encoding the modified *Rhodococcus* bacterial or *Nocardia* bacterial nitrile hydratase according to claim 1.

5. A recombinant vector, comprising the DNA according to claim 4.

6. A transformant, comprising the recombinant vector according to claim 5.

7. A nitrile hydratase collected from a culture obtained by incubating the transformant according to claim 6.

8. A method for producing a nitrile hydratase, the method comprising:

incubating the transformant according to claim 6; and collecting the nitrile hydratase from the obtained culture.

9. A method for producing an amide compound, the method comprising contacting a nitrile compound with a culture, or a processed product of the culture, obtained by incubating the nitrile hydratase according to claim 1.

* * * * *